United States Patent [19]

Digenis et al.

[11] Patent Number: 5,008,245
[45] Date of Patent: Apr. 16, 1991

[54] NOVEL PEPTIDYL CARBAMATE INHIBITORS OF THE ENZYME ELASTASE

[75] Inventors: George A. Digenis, Lexington, Ky.; Bushra J. Agha, Nanuet, N.Y.

[73] Assignee: University of Kentucky Research Foundation, Lexington, Ky.

[21] Appl. No.: 263,385

[22] Filed: Oct. 27, 1988

[51] Int. Cl.[5] .................... A61K 37/64; C07K 5/08
[52] U.S. Cl. .................................. 514/18; 514/19; 514/381; 514/423; 548/251; 548/536
[58] Field of Search .................. 548/251, 536; 514/18, 514/19, 381, 423

[56] References Cited

U.S. PATENT DOCUMENTS 4,643,991 2/1987 Digenis et al. .................. 514/18

OTHER PUBLICATIONS

Digenis, George A., Agha, Bushra, J., Tsuji, Kiyoshi, Kato, Masayuki and Shinogi, Masaki; "Peptidyl Carbamates Incorporating Amino Acid Isosteres as Novel Elastase Inhibitors" Journal of Medicinal Chemistry, 1986, 29, 1468.

Zimmerman, Morris, Morman, Harriet, Mulvey Dennis, Jones, Howard, Frankshun, Robert and Ashe, Bonnie M.; "Inhibition of Elastase and Other Serine Proteases by Heterocyclic Acylating Agents", Journal Biol. Chemistry, vol. 255, No. 20, pp. 9848-9851, 1980.

Janoff, Aaron and Dearing, Rosemarie: "Prevention of Elastase-Induced Experimental Emphysema by Oral Administration of a Synthetic Elastase Inhibitor", American Review of Respiratory Disease, vol. 121, 1980.

Tsuji, K., Agha, B. J., Shinogi, M. and Digenis, G. A.: "Peptidyl Carbamate Esters: A New Class of Specific Elastase Inhibitors", Biochem. & Biophys. Comm., vol. 122, No. 2, 1984, pp. 571-576.

Scofield, Rolfe, E., Werner, P. and Wold, Finn: "p-Nitrophenyl Carbamates as Active-Site-Specific Reagents for Serine Proteases", Biochemistry 16 (11) (1977).

Ashe, Bonnie M., Clark, Robert L., Jones, Howard and Zimmerman, Morris: "Selective Inhibition of Human Leukocyte Elastase and Bovine a-Chymotrypsin by Novel Heterocycles", Journal of Biological Chemistry, No. 22, Issue of Nov. 25, pp. 11603-11606, 1981.

Dorn, Conrad P., Zimmerman, Morris, Yang, Shu Shu, Yurewicz, Edward C., Ashe, Bonnie M., Frankshun, Robert and Jones, Howard: "Proteinase Inhibitors. I. Inhibitors of Elastase", Journal of Medicinal Chemistry, 1977, vol. 20, No. 11.

Doyle, B. B., Traub, W., Lorenzi, G. P., Brown, III, F. R. and Blout, E. R.: "Synthesis and Structural Investigation of Poly(L-Alanyl-L-Alanyl-Glycine)", J. Mol. Biol. (1970) 51, 47 59.

(List continued on next page.)

Primary Examiner—Mary C. Lee
Assistant Examiner—Peter James Davis
Attorney, Agent, or Firm—Lowe, Price, LeBlance, Becker & Shur

[57] ABSTRACT

Compounds selected from the group consisting of a compound of the formula

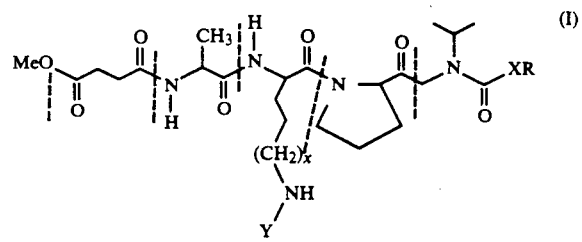

and compound of the formula

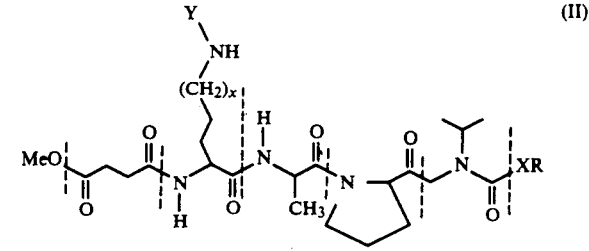

wherein
x is 1 or 2,
Y is carbobenzoxy or benzoyl, and
XR is

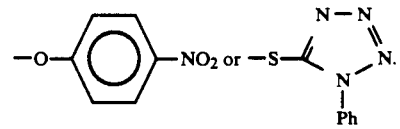

have use as elastase enzyme inhibitors. Particularly potent are the L-proline diastereomers.

Elastase Enzyme inhibitory compositions comprise a carrier and an elastase enzyme inhibiting amount of the compounds of the invention.

A method of selectively inhibiting the enzyme elastase in an animal or a human in need of such treatment comprises administering to the animal or human an enzyme elastase inhibiting amount of one of the compounds of the invention or a composition thereof.

19 Claims, No Drawings

OTHER PUBLICATIONS

Vlasak, J., Rypacek, F., Drobnik, J. and Saudek, V.: "Properties and Reactivity of Polysuccinimide" Institute of Macromolecular Chemistry, Czechoslovak Academy of Sciences, 162 06 Prague 6, Czechoslovakia, (1979).

Brown, Harold H.: "A Study of 2,4,6-Trinitrobenzenesulfonic Acid for Automated Amino Acid Chromatography", Clinical Chemistry, vol. 14, No. 10, 1968, pp. 967–978.

Neri, Paolo, Antoni, Guido, Benvenuti, Franco, Cocola, Francesco and Gazzei, Guido: "Synthesis of $\alpha,\beta$, -Poly [(2-Hydroxyethyl)-DL-Aspartamide], a New Plasma Expander", Journal of Medicinal Chemistry, 1973, vol. 16, No. 8.

Tsuji, K., Agha, B. J., Shinogi, M., Digenis, G. A.: "Peptidyl Carbamate Esters: A New Class of Specific Elastase Inhibitors", Biochemical and Biphysical Research Communications, vol. 122, No. 2, 1984, Jul. 31, 1984, pp. 571–576.

Tuhy, Peter M. and Powers, James C.: "Inhibition of Human Leukocyte Elastase by Peptide Chloromethyl Ketones", Feb. 1975.

Powers, James C., Gupton, B. Frank, Harley, A. Dale, Nishino, Norikazu and Whitley, Ronald J.: "Specificity of Porcine Pancreatic Elastase, Human Leukocyte Elastase and Cathepsin G", Inhibition with Peptide Chloromethyl Ketones, Biochemica et Biophysica Act. 485 (1977) 156–166.

Yoshimura, Toshiaki, Barker, Larry N. and Powers, James C.: "Specificity and Reactivity of Human Leukocyte Elastase, Porcine Pancreatic Elastase, Human Granulocyte Cathepsin G. and Bovine Pancreatic Chymotrypsin with Arylsulfonyl Fluorides" J. Biol. Chem. 257, 5077–5084 (1972).

Groutas, William C., Abrams, William R., Theodorakis, Michael C., Kasper, Annette M., Rude, Steven A.-Badger, Robert C., Ocain, Timothy D., Miller, Kevin E., Moi, Min K., Brubaker, Michael J., Davis, Kathy S. and Zandler, Melvin E.: "Amino Acid Derived Latent Isocyanates: Irreversible Inactivation of Porcine Pancreatic Elastase and Human Leuokocyte Elastase", J. Med. Chem. 1985 28, 204–209.

NOVEL PEPTIDYL CARBAMATE INHIBITORS OF THE ENZYME ELASTASE

TECHNICAL FIELD

This invention relates to novel peptidyl carbamate inhibitors of the enzyme elastase. This invention also relates to novel synthetic routes to synthesize the peptidyl carbamates of the invention and to methods of inhibiting the enzyme elastase with the compounds of the invention.

BACKGROUND ART

Proteinases from polymorphonuclear leukocytes and macrophages, especially elastases (human leukocyte elastase and cathepsin G), appear to be responsible for the chronic tissue destruction associated with inflammation, arthritis and emphysema. During infection or inflammation the normal lung is protected from proteolytic digestion by the protease inhibitor $a_1$-antiryspin. The protective mechanism appears to be non-operative in individuals with an $a_1$-antitrypsin elastase inhibitors capable of replacing $a_1$-antitrypsin therefore appear to be useful in the treatment of pulmonary emphysema and related diseases.

Several types of elastase inhibitors have been reported in the literature. These include peptide chloromethyl ketones as described in "Inhibition of Human Leukocyte Elastase by Peptide Chloromethyl Ketones", P. M. Tuhy and J. C. Powers, FEBS Letters, 50, 359-61 (1975); "Specificity of Porcine Pancreatic Elastase, Human Leukocyte Elastase and Cathepsin G. Inhibition with Peptide Chloromethyl Ketones", J. C. Powers, B. F. Gupton, A. D. Harley, N. Nishino and R. J. Whitley, Biochem. Biophys. Acta. 485, 156-66 (1977); azapeptides "Proteinase Inhibitors. 1. Inhibitors of Elastase", C. P. Dorn, M. Zimmerman, S. S. Yang, E. C. Yurewicz, B. M. Ashe, R. Frankshun and H. Jones, J. Med. Chem., 20: 1464-68 (1977); "Reaction of Serine Proteases with Aza-amino Acid and Aza-peptide Derivatives", J. C. Powers and B. F. Gupton, Meth. Enzymol., 46: 208-16 (1977); sulfonyl fluorides "Specificity and Reactivity of Human Leukocyte Elastase, Porcine Pancreatic Elastase, Human Granulocyte Cathepsin G, and Bovine Pancreatic Elastase, Human Granulocyte Cathepsin G, and Bovine Pancreatic Elastase, Human Granulocyte Cathepsin G, and Bovine Pancreatic Chymotrypsin with Arylsulfonyl Fluorides; "Discovery of a new series of potent and specific irreversible Elastase Inhibitors", T. Yoshimura, L. N. Barker and J. C. Powers, J. Biol. Chem., 257, 5077-84 (1982); heterocyclic acrylating agents "Inhibition of Elastase and Other Serine Proteases by Heterocyclic Acylating Agents", M. Zimmerman, H. Morman, D. Mulvey, H. Jones, R. Frankshun and B. M. Ashe, J. Biol. Chem., 255: 9848-51 (1980); "Selective Inhibition of Human Leukocyte Elastase and Bovine $a_1$-Chymotrypsin by Novel Heterocycles", B. M. Ashe, R. L. Clark, H. Jones and M. Zimmerman, J. Biol. Chem., 256: 11603-6 (1981); imidazole N-carboxamides, W. C. Groutas, R. C. Badger, T. D. Ocain, D. Felker, J. Frankson and M. Theodorakis, Biochem. Biophys. Res. Commun., 95: 1890 (1980); and p-nitrophenyl-N alkyl carbamates, "p-Nitrophenyl Carbamates as Active-Site-Specific Reagents for Serine Proteases", R. E. Scofield, R. P. Werner and F. Wold, Biochemistry, 16: 2492 (1977).

Although some peptide chloromethyl ketones have been shown to be effective in preventing elastase induced emphysema in animal models there is considerable question whether such reactive agents could be used for treating emphysema in humans. ("Prevention of Elastase Induced Experimental Emphysema by Oral Administration of a Synthetic Elastase Inhibitor," A. Janoff and R. Dearing, Am. J. Respir. Dis., 121: 1025-3 (1980)). This is not surprising since the alkylating moieties in these inhibitors might render them toxic when used on a continuous basis. To be suitable for human use, an enzyme inhibitor has to show a high degree of selectively and must have minimal toxic side effects. As a result, most drugs are molecules that reversibly bind to specific enzymes or receptor sites. Examples are the carbamate esters physostigmine and neostigmine which have been clinically used as inhibitors of acetyl choline esterases, A. G. Gilman, L. S. Goodman and A. Gilman, "The pharmacological Basis of Therapeutics", p. 101, MacMillan Publishing Co. (1980).

A series of peptide elastase inhibitors were disclosed in U.S. Pat. No. 4,643,991 to Digenis et al. Another group of polymer-bound elastase inhibitors was disclosed in U.S. application Ser. No. 242,294 by Digenis et al filed on Sept. 9, 1988.

There still remains a need in the art for compounds which are superior specific, active-site directed inhibitors of the enzyme elastase without the concommittant detrimental features of other prior art compounds.

SUMMARY OF THE INVENTION

This invention relates to a compound of the formula selected from the group consisting of
a compound of the formula

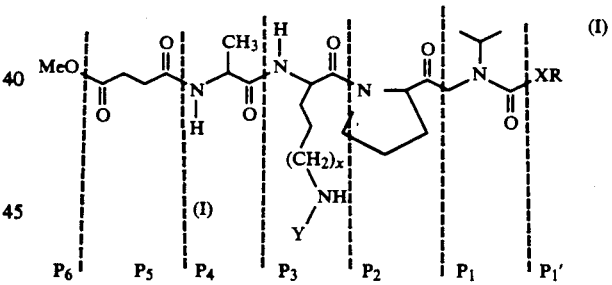

and
a compound of the formula

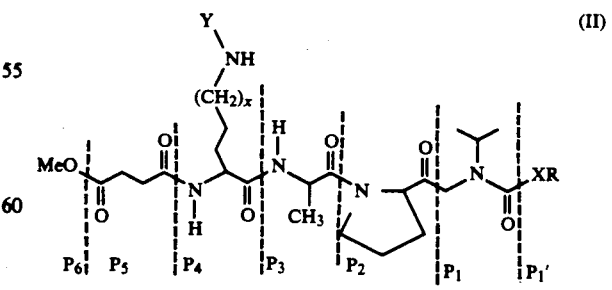

wherein
x is 1 or 2,
Y is carbobenzoxy or benzoyl, and
XR =

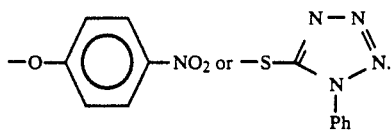

This invention also provides an enzyme elastase inhibitory composition comprising an enzyme elastase inhibitory amount of the compound of the invention, and a carrier.

Also part of the invention is a method of inhibiting the activity of the enzyme elastase comprising adding to an enzyme solution an enzyme elastase inhibitory amount of the compound of the invention.

This invention also relates to a method of selectively inhibiting the activity of the enzyme elastase in the presence of an enzyme selected from the group consisting of trypsin and chymotrypsin comprising adding to an elastase enzyme solution an enzyme elastase inhibitory amount of the compound of the invention.

Still part of this invention is a method of selectively inhibiting the enzyme elastase in an animal or human in need of such treatment comprising administering to said animal or human an enzyme elastase inhibiting amount of the compound of the invention.

Other objects, advantages and features of the present invention will become apparent to those skilled in the art from the following discussion.

BEST MODE FOR CARRYING OUT THE INVENTION

This invention arose from the desire of providing novel, more potent and selective peptidyl carbamate inhibitors of the enzyme elastase. Thus, the present genus of peptidyl carbamate inhibitors incorporates derivatized lysine and ornithine residues into the $P_3$ or $P_4$ positions of the dipeptides, i.e., the compounds of formulas I and II. The present compounds resemble the desmosine cross-linking units in mature elastin, which is the natural substrate of the human leukocyte elastase enzyme.

Thus, this invention provides certain novel substituted peptidyl carbamate compounds, pharmaceutical compositions containing these compounds, and methods for using these pharmaceutical compositions in the selective inhibition of the enzyme elastase without affecting similar serine dependent proteases, e.g., trypsin and chymotrypsin.

It is known from the art that proteases from polymorphonuclear leukocytes and macrophages, especially elastases (human leukocyte HL elastase and cathepsin G) appear to be responsible for the chronic tissue destruction associated with inflammation, arthritis and emphysema. During infection or inflammation, the normal lung is protected from proteolytic digestion by the protease inhibitor, $a_1$-antitrypsin. This protective mechanism appears to be non-operative in individuals with an $a_1$-antitrypsin deficiency due to genetic or other causes. Synthetic elastase inhibitors capable of replacing $a_1$-antitrypsin are therefore useful in the treatment of pulmonary emphysema and related diseases.

According to the present invention, a class of compounds containing the carbamate functionality and oligopeptides have been found to be superior activesite directed inhibitors of the enzyme elastase in animals and humans. This class of compounds, therefore, provides an opportunity to incorporate chemical moieties of increased affinity towards the enzyme, and greater capability for the transfer of the acylating moiety to the active site of the enzyme. The nature of the acylating moiety may be varied to optimize the duration of the enzymatic inactivation.

The mechanism of the invention appears to take advantage of the fact that these carbamate esters will react with proteases and esterases at the carbonyl carbon by losing the alkoxy portion and transferring the carbamylating moiety to the active site of the enzyme. Acylation will then lead to recovery of enzymatic activity.

The present invention provides a series of carbamate compounds which are active in accordance with the above proposals as elastase enzyme inhibitors. These novel compounds are carbamates substituted by oligopeptides which are selected from the group consisting of a compound of the formula

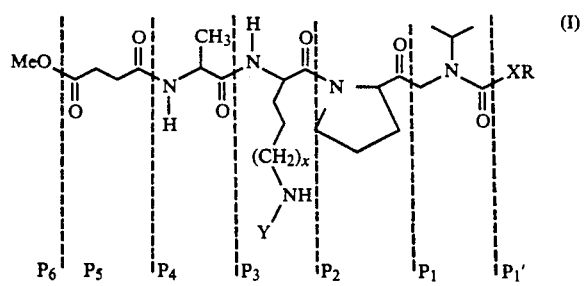

and a compound of the formula

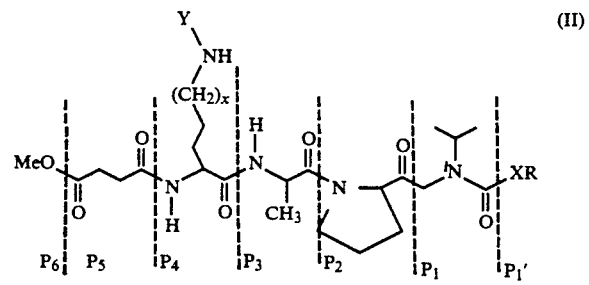

wherein x is 1 or 2;

Y is carbobenzoxy or benzoyl; and

XR =

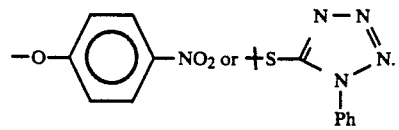

In a more preferred and detailed embodiment the compound of the invention is selected from the group consisting of 1. p-Nitrophenyl N-[(Methoxysuccinyl)-L-alanyl-L-alanyl-L-prolylmethyl]-N-isopropylcarbamate,
2. Methyl succinimide succinate
3. t-Butyl Methoxysuccinyl-L-alanine ester,
4. Methoxysuccinyl-L-alanine,
5. $N_\alpha$-Methoxysuccinyl-L-alanyl-$N_\epsilon$-benzoyl-L-lysine, 6. $N_\alpha$-Methoxysuccinyl-L-alanyl-$N_\epsilon$-carbobenzoxy-L-lysine phenacyl ester,
7. $N_\alpha$-Methoxysuccinyl-L-alanyl-$N_\epsilon$-carbobenzoxy-L-lysine,
8. $N_\alpha$-Methoxysuccinyl-L-alanyl-$N_\delta$-carbobenzoxy-L-ornithine phenacyl ester,
9. $N_\alpha$-Methoxysuccinyl-L-alanyl-$N_\delta$-carbobenzoxy-L-ornithine,
10. $N_\alpha$-Methoxysuccinyl-$N_\delta$-carbobenzoxy-L-ornithine,
11. $N_\alpha$-Methoxysuccinyl-$N_\delta$-carbobenzoxy-L-ornithyl-L-alanine t-butyl ester,
12. $N_\alpha$-Methoxysuccinyl-$N_\delta$-carbobenzoyl-L-ornithyl-L-alanine,
13. $N_\alpha$-Methoxysuccinyl-$N_\epsilon$-carbobenzoxy-L-lysine,
14. $N_\alpha$-Methoxysuccinyl-$N_\epsilon$-carbobenzoxy-L-lysyl-L-alanine t-butyl ester,
15. $N_\alpha$-Methoxysuccinyl-$N_\epsilon$-carbobenzoxy-L-lysyl-L-alanine,
16. $N_\alpha$-Methoxysuccinyl-$N_\epsilon$-benzoyl-L-lysine,
17. $N_\alpha$-Methoxysuccinyl-$N_\epsilon$-benzoyl-L-lysyl-L-alanine t-butyl ester,
18. $N_\alpha$-Methoxysuccinyl-$N_\epsilon$-benzoyl-L-lysyl-L-alanine,
19. N-Boc-L-prolyl chloromethyl ketone,
20. N-[(N-Boc-L-prolyl)methyl]isopropylamine,
21. N-[(N-Boc-L-prolyl)methyl]-N-isopropylcarbamate,
22. p-Nitrophenyl N-(L-prolylmethyl)-N-isopropyl-carbamate hydrochloride,
23. $N_\alpha$-Methoxysuccinyl-L-alanyl-$N_\epsilon$-carbobenzoxy-L-lysyl-D-proline phenacyl ester,
24. $N_\alpha$-Methoxysuccinyl-L-alanyl-$N_\epsilon$-carbobenzoxy-L-lysyl-L-proline phenacyl ester,
25. $N_\alpha$-Methoxysuccinyl-L-alanyl-$N_\epsilon$-carbobenzoxy-L-lysyl-D-proline,
26. $N_\alpha$-Methoxysuccinyl-L-alanyl-$N_\epsilon$-carbobenzoxy-L-lysyl-L-proline,
27. $N_\alpha$-Methoxysuccinyl-L-alanyl-$N_\epsilon$-carbobenzoxy-L-lysyl-D-prolyl chloromethyl ketone,
28. $N_\alpha$-Methoxysuccinyl-L-alanyl-$N_\epsilon$-carbobenzoxy-L-lysyl-L-prolylchloromethyl ketone,
29. N-[Methoxysuccinyl-L-alanyl-($N_\epsilon$-carbobenzoxy)-L-lysyl-D-proplylmethyl]-N-isopropylamine,
30. N-[Methoxysuccinyl-L-alanyl-($N_\epsilon$-carbobenzoxy)-L-lysyl-L-prolylmethyl]-N-isopropylamine,
31. $N_\alpha$-t-Boc-$N_\epsilon$carbobenzoxy-L-lysine,
32. $N_\alpha$-t-Boc-$N_\epsilon$-carbobenzoxy-L-lysine phenacyl ester,
33. $N_\epsilon$-Carbobenzoxy-L-lysine phenacyl ester hydrochloride,
34. $N_\alpha$-t-Boc-$N_\delta$-carbobenzoyl-L-ornithine,
35. $N_\alpha$-t-Boc-$N_\delta$-carbobenzoxy-L-ornithine phenacyl ester,
36. $N_\delta$-Carbobenzoxy-L-ornithine phenacyl ester hydrochloride,
37. N-t-Boc-D-proline,
38. N-t-Boc-L-proline,
39. N-t-Boc-D-proline phenacyl ester,
40. N-t-Boc-L-proline phenacyl ester,
41. D-Proline phenacyl ester hydrochloride,
42. L-Proline phenacyl ester hydrochloride,
43. $N_\epsilon$-Benzoyl-L-lysine,
44a. p-Nitrophenyl N-[Methoxysuccinyl-($N_\epsilon$-carbobenzoxy)-L-lysyl-L-alanyl-L-prolylmethyl]-N-isopropylcarbamate,
44b. p-Nitrophenyl-N-[Methoxysuccinyl-($N_\epsilon$-carbobenzoxy)-L-lysyl-L-alanyl-D-prolylmethyl]-N-isopropylcarbamate,
45a. p-Nitrophenyl-N-[Methoxysuccinyl-($N_\epsilon$-benzoyl)-L-lysyl-L-alanyl-L-prolylmethyl]-N-isopropylcarbamate,
45b. p-Nitrophenyl-N-[Methoxysuccinyl-($N_\epsilon$-benzoyl)-L-lysyl-L-alanyl-D-prolylmethyl]-N-isopropylcarbamate,
46a. p-Nitrophenyl-N-[Methoxysuccinyl-($N_\delta$-carbobenzoxy)-L-ornithy-L-alanyl-L-prolylmethyl]-N-isopropylcarbamate,
46b. p-Nitrophenyl-($N_\delta$-carbobenzoxy)-L-ornithyl-L-alanyl-D-prolylmethyl]-N-isopropylcarbamate,
47a. p-Nitrophenyl-N-[Methoxysuccinyl-($N_\delta$-benzoyl)-L-ornithyl-L-alanyl-L-prolylmethyl]-N-isopropylcarbamate,
47b. p-Nitrophenyl-N-[Methoxysuccinyl-($N_\delta$-benzoyl)-L-ornithyl-L-alanyl-D-prolylmethyl]-N-isopropylcarbamate,
48a. p-Nitrophenyl-N-[Methoxysuccinyl-L-alanyl-($N_\epsilon$-carbobenzoxy)-L-lysyl-L-prolylmethyl]-N-isopropylcarbamate,
48b. p-Nitrophenyl N-[Methoxysuccinyl-L-alanyl-($N_\epsilon$-carbobenzoxy)-L-lysyl-D-prolylmethyl]-N-isopropylcarbamate,
49a. p-Nitrophenyl N-[Methoxysuccinyl-L-alanyl-($N_\epsilon$-benzoyl)-L-lysyl-L-prolylmethyl]-N-isopropylcarbamate,
49b. p-Nitrophenyl N-[Methoxysuccinyl-L-alanyl-($N_\epsilon$-benzoyl)-L-lysyl-D-prolylmethyl]-N-isoproplcarbamate,
50a. p-Nitrophenyl N-[Methoxysuccinyl-L-alanyl-($N_\delta$-carbobenzoxy)-L-ornithyl-L-prolymethyl]-N-isopropylcarbamate,
50b. p-Nitrophenyl N-[Methoxysuccinyl-L-alanyl-($N_\delta$-carbobenzoxy)-L-ornithyl-D-prolylmethyl]-N-isopropylcarbamate,
51a. p-Nitrophenyl N-[Methoxysuccinyl-L-alanyl-($N_\delta$-benzoyl)-L-ornithyl-L-prolylmethyl]-N-isopropylcarbamate,
51b. p-Nitrophenyl N-[Methoxysuccinyl-L-alanyl-($N_\delta$-benzoyl)-L-ornithyl-D-prolymethyl]-N-isopropylcarbamate,
52. S-(1-phenyl-5-tetrazol) chloroformate,
53. S-(1-phenyl-5-tetrazoyl)-N-[(N-Boc-L-prolyl)methyl]-N-isopropyl-thiocarbamate,
54. S-(1-phenyl-5-tetrazoyl-N-prolymethyl)-N-isopropyl-thio carbamate hydrochloride,
PC5. S-(1-phenyl-5-tetrazoyl)-N-[methoxysuccinyl-alanyl-($N_\epsilon$-Carbobenzoxyl) lysyl prolyl methyl]-N-isopropyl-thio carbamate, and
PC6. S-(1-phenyl-5-tetrazoyl)-N-[methoxysuccinyl-(N-carbobenzoyl)ornithylalanyl(prolylmethyl)-N-isopropylthio carbamate.

In another particularly preferred embodiment of the invention the elastase enzyme inhibitors of this invention are selected from the group consisting of
1. p-Nitrophenyl N-[(Methoxysuccinyl)-L-alanyl-L-alanyl-L-prolylmethyl]-N-isopropylcarbamate,
2. Methyl succinimide succinate
3. t-Butyl Methoxysuccinyl-L-alanine ester,
4. Methoxysuccinyl-L-alanine,
5. $N_\alpha$-Methoxysuccinyl-L-alanyl-$N_\epsilon$-benzoyl-L-lysine,
6. $N_\alpha$-Methoxysuccinyl-L-alanyl-$N_\epsilon$-carbobenzoxy-L-lysine phenacyl ester,
7. $N_\alpha$-Methoxysuccinyl-L-alanyl-$N_\epsilon$-carbobenzoxy-L-lysine,
8. $N_\alpha$-Methoxysuccinyl-L-alanyl-$N_\delta$-carbobenzoxy-L-ornithine phenacyl ester, 9. $N_\alpha$-Methoxysuccinyl-L-alanyl-$N_\delta$-carbobenzoxy-L-ornithine,
10. $N_\alpha$-Methoxysuccinyl-$N_\delta$-carbobenzoxy-L-ornithine,
11. $N_\alpha$-Methoxysuccinyl-$N_\delta$-carbobenzoxy-L-ornithyl-L-alanine t-butyl ester,
12. $N_\alpha$-Methoxysuccinyl-$N_\delta$-carbobenzoyl-L-ornithyl-L-alanine,
13. $N_\alpha$-Methoxysuccinyl-$N_\epsilon$-carbobenzoxy-L-lysine,
14. $N_\alpha$-Methoxysuccinyl-$N_\epsilon$-carbobenzoxy-L-lysyl-L-alanine t-butyl ester,
15. $N_\alpha$-Methoxysuccinyl-$N_\epsilon$-carbobenzoxy-L-lysyl-L-alanine,
16. $N_\alpha$-Methoxysuccinyl-$N_\epsilon$-benzoyl-L-lysine,
17. $N_\alpha$-Methoxysuccinyl-$N_\epsilon$-benzoyl-L-lysyl-L-alanine t-butyl ester,
18. $N_\alpha$-Methoxysuccinyl-$N_\epsilon$-benzoyl-L-lysyl-L-alanine,
19. N-Boc-L-prolyl chloromethyl ketone,
20. N-[(N-Boc-L-prolyl)methyl]isopropylamine,
21. N-[(N-Boc-L-prolyl)methyl]-N-isopropylcarbamate,
22. p-Nitrophenyl N-(L-prolylmethyl)-N-isopropyl-carbamate hydrochloride,
23. $N_\alpha$-Methoxysuccinyl-L-alanyl-$N_\epsilon$-carbobenzoxy-L-lysyl-D-proline phenacyl ester,
24. $N_\alpha$-Methoxysuccinyl-L-alanyl-$N_\epsilon$-carbobenzoxy-L-lysyl-L-proline phenacyl ester,
25. $N_\alpha$-Methoxysuccinyl-L-alanyl-$N_\epsilon$-carbobenzoxy-L-lysyl-D-proline,
26. $N_\alpha$-Methoxysuccinyl-L-alanyl-$N_\epsilon$-carbobenzoxy-L-lysyl-L-proline, and
27. $N_\alpha$-Methoxysuccinyl-L-alanyl-$N_\epsilon$-carbobenzoxy-L-lysyl-D-prolyl chloromethyl ketone.

In yet another preferred embodiment the enzyme elastase inhibitors of this invention are selected from the group consisting of
28. $N_\alpha$-Methoxysuccinyl-L-alanyl-$N_\epsilon$-carbobenzoxy-L-lysyl-L-prolyl chloromethyl ketone,
29. N-[Methoxysuccinyl-L-alanyl-($N_\epsilon$-carbobenzoxy)-L-lysyl-D-prolylmethyl]-N-isopropylamine,
30. N-[Methoxysuccinyl-L-alanyl-($N_\epsilon$-carbobenzoxy)-L-lysyl-L-prolylmethyl]-N-isopropylamine,
31. $N_\alpha$-t-Boc-$N_\epsilon$-carbobenzoxy-L-lysine,
32. $N_\alpha$-t-Boc-$N_\epsilon$-carbobenzoxy-L-lysine phenacyl ester,
33. $N_\epsilon$-Carbobenzoxy-L-lysine phenacyl ester hydrochloride,
34. $N_\alpha$-t-Boc-$N_\delta$-carbobenzoyl-l-ornithine,
35. $N_\alpha$-t-Boc-$N_\delta$-carbobenzoxy-L-ornithine phenacyl ester,
36. $N_\delta$-Carbobenzoxy-L-ornithine phenacyl ester hydrochloride,
37. N-t-Boc-D-proline,
38. N-t-Boc-L-proline,
39. N-t-Boc-D-proline phenacyl ester,
40. N-t-Boc-L-proline phenacyl ester,
41. D-Proline phenacyl ester hydrochloride,
42. L-Proline phenacyl ester hydrochloride,
43. $N_\epsilon$-Benzoyl-L-lysine,
44a. p-Nitrophenyl N-[Methoxysuccinyl-($N_\epsilon$-carbobenzoxy)-L-lysyl-L-alanyl-L-prolylmethyl]-N-isopropylcarbarmate,
44b. p-Nitrophenyl N-[Methoxysuccinyl-($N_\epsilon$-carbobenzoxy)-L-lysyl-L-alanyl-D-prolylmethyl]-N-isopropylcarbarmate,
45a. p-Nitrophenyl N-[Methoxysuccinyl-($N_\epsilon$-benzoyl)-L-lysyl-L-alanyl-L-prolylmethyl]-N-isopropylcarbarmate,
45b. p-Nitrophenyl N-[Methoxysuccinyl-($N_\epsilon$-benzoyl)-L-lysyl-L-alanyl-D-prolylmethyl]-N-isopropylcarbarmate,
46a. p-Nitrophenyl N-[Methoxysuccinyl-($N_\delta$-carbobenzoxy)-L-ornithyl-L-alanyl-L-prolylmethyl]-N-isopropylcarbarmate,
46b. p-Nitrophenyl-($N_\delta$-carbobenzoxy)-L-ornithyl-L-alanyl-D-prolylmethyl]-N-isopropylcarbarmate,
47a. p-Nitrophenyl N-[Methoxysuccinyl-($N_\delta$-benzoyl)-L-ornithyl-L-alanyl-L-prolylmethyl]-N-isopropyl-carbarmate,
47b. p-Nitrophenyl N-[Methoxysuccinyl-($N_\delta$-benzoyl)-L-ornithyl-L-alanyl-D-prolylmethyl]-N-isopropyl-carbarmate, and
48a. p-Nitrophenyl N-[Methoxysuccinyl-L-alanyl-($N_\epsilon$-carbobenzoxy)-L-lysyl-L-prolylmethyl]-N-isopropylcarbarmate.

In still another preferred embodiment of the invention the elastase enzyme inhibitor is selected from the group consisting of
48b. p-Nitrophenyl N-[Methoxysuccinyl-L-alanyl-($N_\epsilon$-carbobenzoxy)-L-lysyl-d-prplylmethyl]-N-isopropylcarbamate,
49a. p-Nitrophenyl N-[Methoxysuccinyl-L-alanyl-($N_\epsilon$-benzoyl)-L-lysyl-L-prolylmethyl]-N-isopropylcarbamate,
49b. p-Nitrophenyl N-[Methoxysuccinyl-L-alanyl-($N_\epsilon$-benzoyl)-L-lysyl-D-prolylmethyl]-N-isopropylcarbamate,
50a. p-Nitrophenyl N-[Methoxysuccinyl-L-alanyl-($N_\delta$-carbobenzoxy)-L-ornithyl-L-prolylmethyl]-N-isopropylcarbamate,
50b. p-Nitrophenyl N-[Methoxysuccinyl-L-alanyl-($N_\delta$-carbobenzoxy)-L-ornithyl-d-prolylmethyl]-N-isopropylcarbamate,
51a. p-Nitrophenyl N-[Methoxysuccinyl-L-alanyl-($N_\delta$-benzoyl)-L-ornithyl-L-prolylmethyl]-N-isopropyl-carbamate,
51b. p-Nitrophenyl N-[Methoxysuccinyl-L-alanyl-($N_\delta$-benzoyl)-L-ornithyl-D-prolylmethyl]-N-isopropyl-carbamate,
52. S-(1-phenyl-5-tetrazol)chloroformate,
53. S-(1-phenyl-5-tetrazoyl)-N-[(N-Boc-L-prolyl)methyl]-N-isopropyl-thiocarbamate,
54. S-(1-phenyl-5-tetrazoyl-N-prolymethyl)-N-isopropyl-thio carbamate hydrochloride,
PC5. S-(1-phenyl-5-tetrazoyl)-N-[methoxysuccinyl-alanyl-($N_\epsilon$-Carbobenzoxyl) lysyl prolyl methyl]-N-isopropyl-thio carbamate, and
PC6. S-(1-phenyl-5-tetrazoyl)-N-[methoxysuccinyl(N-carbobenzoyl)ornithylalanyl(prolylmethyl)N-isopropylthio carbamate.

Of the above compounds still more preferred are those having the formula

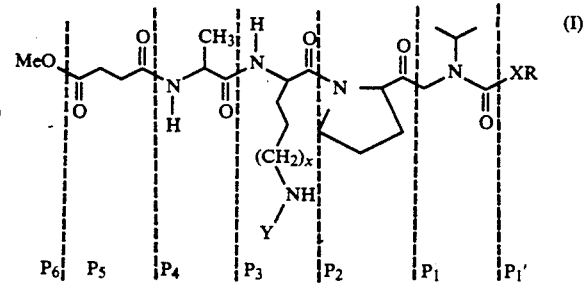

wherein x is 1 or 2;
Y is carbobenzoxy or benzoyl; and
XR is

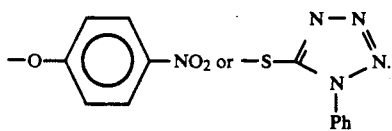

Also a more preferred group of compounds of the invention are those having the formula

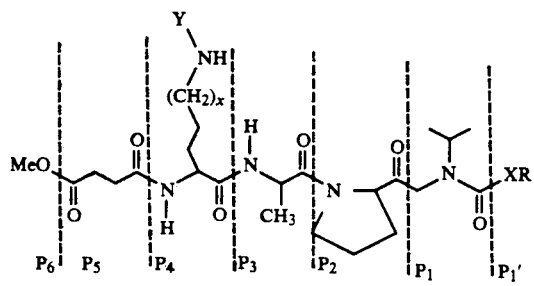

wherein
x is 1 or 2;
X is carbobenzoxy or benzoyl; and
XR is

Two synthetic routes are provided herein to produce the p-nitrophenyl peptidyl carbamates of the invention. One of the synthetic routes is designed to incorporate D or L proline into the $P_2$ position of the molecule in a stereospecific manner. Derivatives incorporating D-proline, however, possess reduced elastase enzyme inhibitory properties when compared to their diastereomers which incorporate L-proline at the $P_2$ position.

The peptidyl carbamate inhibitors of the invention selectively inhibit the enzyme elastase, e.g., human leukocyte elastase (HLE) and porcine pancreatic elastase (PPE), with inhibitor dissociation constants ranging from $3 \times 10^{-6}M$ to $2 \times 10^{-9}M$.

All the peptidyl carbamate inhibitors of the invention have been found to selectively inhibit the enzyme elastase without inhibiting other enzymes such as trypsin or chymotrypsin, amont other enzymes.

The peptidyl carbamate inhibitors of the invention are desmosine-like derivatives incorporating L-lysine or L-ornithine residues at the $P_3$ or $P_4$ regions of their structures. These features simulate the protruding chains of desmosine cross-linking units in mature elastin.

The present compounds are synthesized in general by methods which are improvements over the method described in U.S. Pat. No. 4,643,991 to Digenis et al, the entire content of which is incorporated herein by reference. The synthetic approach of this invention involves the coupling of the $P_6$-$P_3$ moieties of the inhibitor molecules with the $P_2$-$P_1$ moieties as depicted in Scheme 1 herebelow.

Scheme 1
General synthesis of desmosine-like peptidyl carbamates. Coupling of $P_6$-$P_3$ moiety with the $P_2$-$P_1'$ moiety

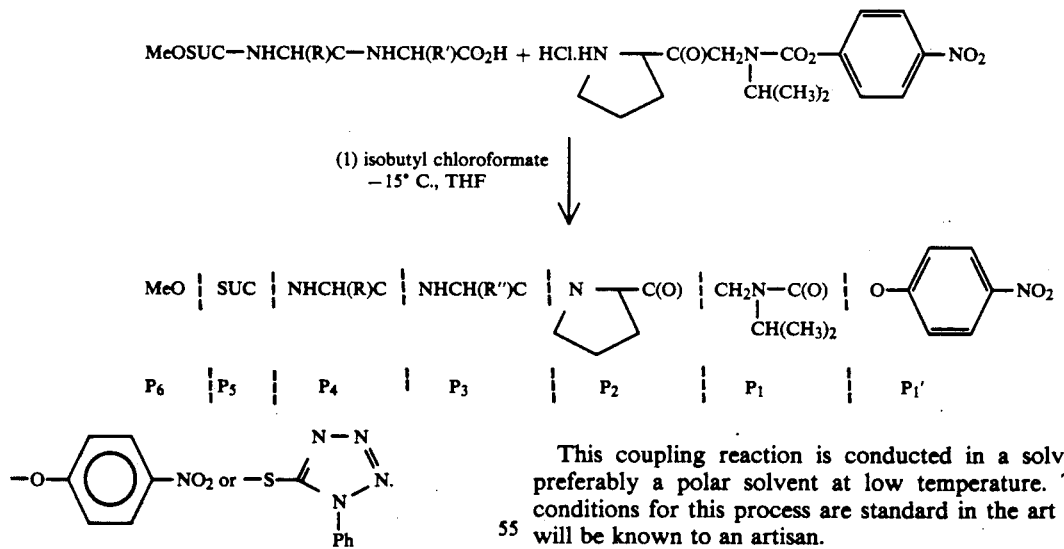

This coupling reaction is conducted in a solvent, preferably a polar solvent at low temperature. The conditions for this process are standard in the art and will be known to an artisan.

The synthesis of methoxysuccinyl-alanine aminoacid dipeptides of the invention is depicted in Scheme 2 herebelow Scheme 2
Synthesis of the MeOSUC-Ala-Amino acid dipeptides.

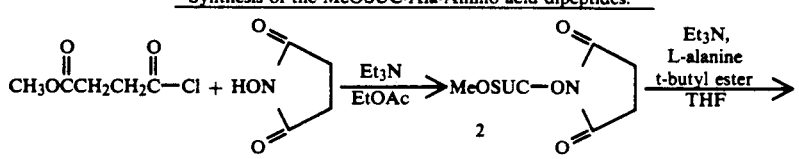

Scheme 2
Synthesis of the MeOSUC-Ala-Amino acid dipeptides.

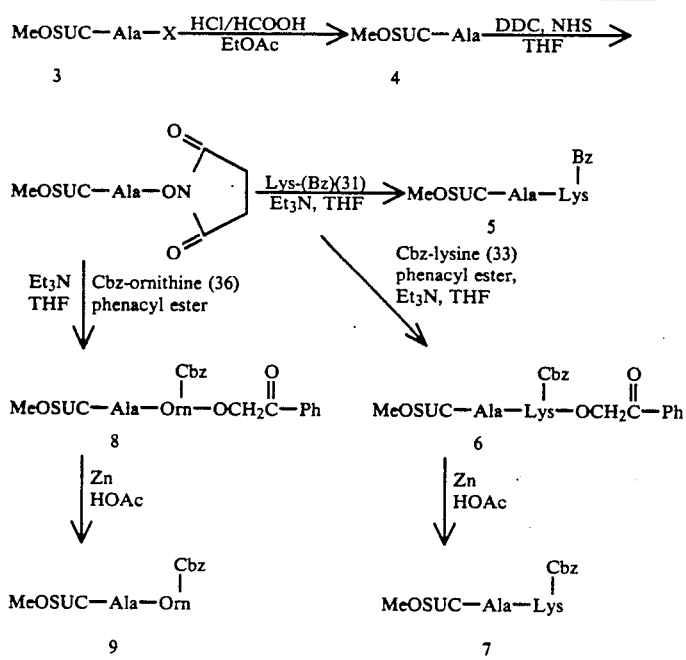

The synthesis of methoxysuccinyl-alanine aminoacid dipeptides in which the aminoacid residue can be ornithine (residue 9) or lysine (residue 7) with carbobenzoxy (Cbz) or benzoyl (Bz) groups at their terminal amine function ($N_\epsilon$) is shown in Scheme 2. These reactions are conducted under standard conditions which are known to an artisan.

The synthesis of methoxysuccinyl-aminoacid-alanine dipeptides is depicted in Scheme 3 herebelow.

Scheme 3
Synthesis of the MeOSUC-Amino acid-Ala dipeptides

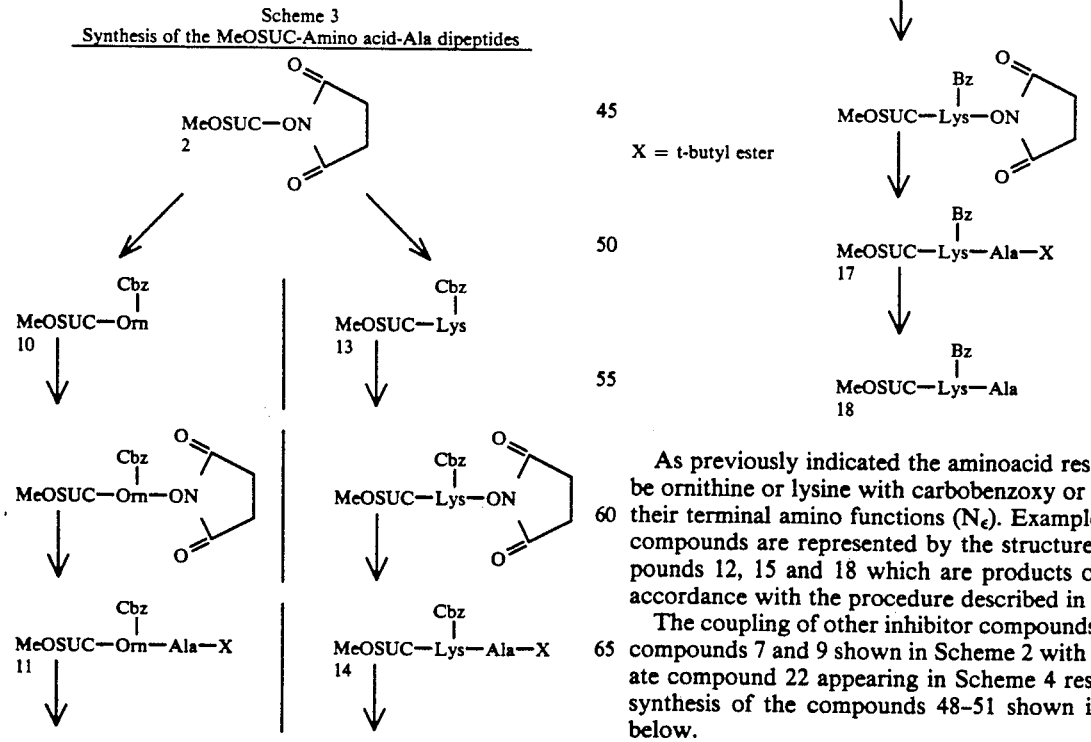

X = t-butyl ester

As previously indicated the aminoacid residue could be ornithine or lysine with carbobenzoxy or benzoyl at their terminal amino functions ($N_\epsilon$). Examples of these compounds are represented by the structures of Compounds 12, 15 and 18 which are products obtained in accordance with the procedure described in Scheme 3.

The coupling of other inhibitor compounds similar to compounds 7 and 9 shown in Scheme 2 with intermediate compound 22 appearing in Scheme 4 results in the synthesis of the compounds 48–51 shown in Table 2 below.

TABLE 2

Inhibition of HLE by Desmosine-like Peptidyl Carbamates; Variations in $P_3$

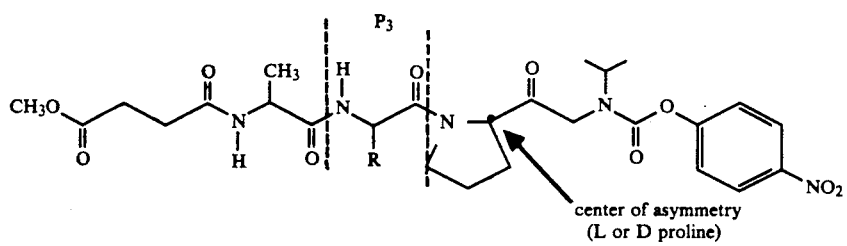

center of asymmetry
(L or D proline)

| Cpd. | $P_3{}^a$ | Isomer[b] | $K_i$ values ($\mu M$) Dixon[c] | Replot[d] |
|---|---|---|---|---|
| 48 | $N_\epsilon$—Cbz—Lys | (a) L | 1.10 | 0.22 |
|  |  | (b) D | 20.40 | 11.33 |
| 49 | $N_\epsilon$—Bz—Lys | (a) L | 1.60 | 0.31 |
|  |  | (b) D | 34.00 | 38.50 |
| 50 | $N_\delta$—Cbz—Orn | (a) L | 0.75 | 1.05 |
|  |  | (b) D | 22.20 | 19.25 |
| 51 | $N_\delta$—Bz—Orn | (a) L | 5.33 | 2.14 |
|  |  | (b) D | 104.00 | 100.00 |

[a]Cbz = carbobenzoxy; Bz = benzoyl; Lys = L-lysine; Orn = L-ornithine.
[b]L & D refer to the configuration at the prolyl α-carbon.
[c]Lines contained linear regression analysis correlations of >0.950.
[d]$K_i$ values determined from Lineweaver-Burk slope replots. Slopes were obtained from lines with linear regression analysis correlations of >0.990.

Table 2 provides $K_i$ values for 2 diastereomers of each compound (a and b). In all cases the diastereomers incorporate L proline, where L or D refers to the configuration at the propylα-carbon, exhibit greater inhibitory activity against the enzyme elastase than their corresponding diastereomers derived from D-proline.

The coupling of the intermediate compounds such as compounds 12, 15 and 18 shown in Scheme 3 with compound 22 shown in Scheme 4 herebelow results in the synthesis of compounds 44–47 shown in Table 1 herebelow.

Scheme 4

Synthesis of $P_3$-$P_1'$ moiety as the stable hydrochloride salt (22).

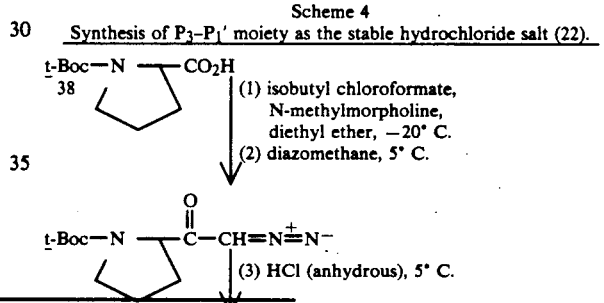

TABLE 1

Inhibition of HLE by Desmosine-like Peptidyl Carbamates; Variations in $P_4$

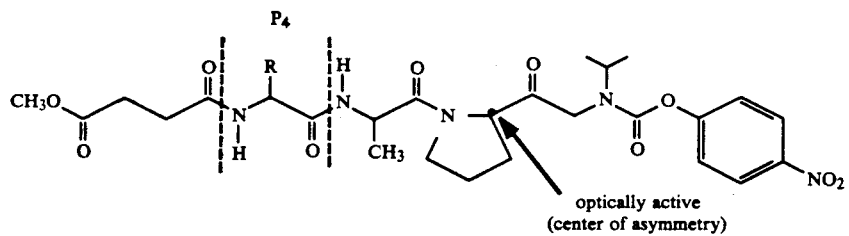

optically active
(center of asymmetry)

| Cpd. | $P_4{}^a$ | Isomer | $K_i$ value ($\mu M$) Dixon[c] | Replot[d] |
|---|---|---|---|---|
| 44 | $N_\epsilon$—Cbz—Lys | (a) L | 0.56 | 0.47 |
|  |  | (b) D | 7.30 | 7.63 |
| 45 | $N_\epsilon$—Bz—Lys | (a) L | 0.73 | 0.38 |
|  |  | (b) D | 3.70 | 3.13 |
| 46 | $N_\delta$—Cbz—Orn | (a) L | 0.43 | 0.36 |
|  |  | (b) D | 8.80 | 7.95 |
| 47 | $N_\delta$—Bz—Orn | (a) L | 0.65 | 0.19 |
|  |  | (b) D | 10.00 | 17.70 |

[a]Cbz = carbobenzoxy; Bz = benzoyl; Lys = L-lysine; Orn = L-ornithine.
[b]L & D refer to the configuration at the prolyl α-carbon.
[c]Lines contained linear regression analysis correlations of >0.950.
[d]$K_i$ values determined from Lineweaver-Burk slope replots. Slopes were obtained from lines with linear regression analysis correlations of >0.990.

Scheme 4 is shown herebelow and provides the synthesis of $P_3$-$P_1$ moieties as their stable hydrochloride salts (compound 22).

-continued
Scheme 4
Synthesis of P$_3$-P$_1$' moiety as the stable hydrochloride salt (22).

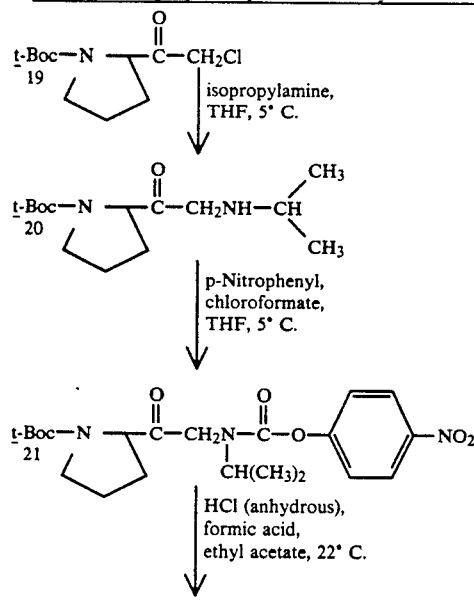

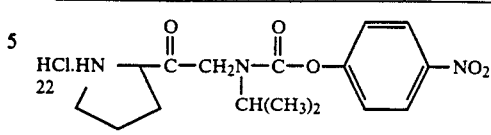

These reactions are also conducted under conditions which are standard in the art and would be known to an artisan.

As already indicated above here also the diastereomers incorporating L proline designated as a) are shown to have a greater inhibitory capacity against the enzyme elastase, e.g. HLE, than those compounds derived from D-proline as shown in Table 1 above.

In all cases compound 22 is synthesized from compound 38 by a synthetic route which is shown in Scheme 4 hereabove.

The stereo specific synthesis of compounds 44–51 follows a synthetic procedure which is depicted in Scheme 5 herebelow.

Scheme 5
Stereospecific synthesis of desmosine-like peptidyl carbamates.

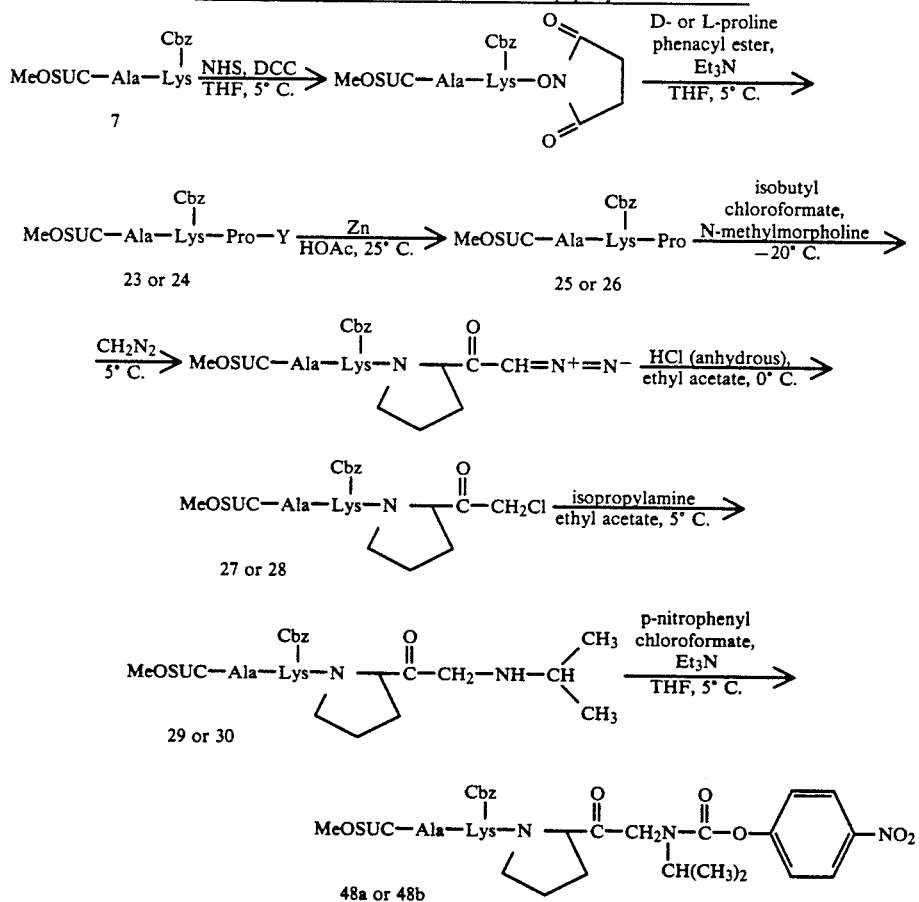

Y = phenacyl ester

As in the previous cases the conditions for conducting the various steps in this method are standard in the art and would be known to an artisan.

The peptidyl carbamate inhibitor of Formula 46 may be synthesized from all L aminoacids (L-L isomer).

When tested against human leukocyte elastase enzyme it is evidenced that its inhibitory activity may be enhanced by utilizing a 50:50 mixture of the two diastereomers which result from the incorporation of D or L proline into the structure of compound 46.

Table 3 below shows the effect of the stereo chemistry at $P_2$ on the elastase enzyme inhibitory activity of compound 46 of this invention.

functionality at $P_1$ of Formulas I and II by N-phenylthiotetrazole. This results in compounds PC5 and PC6 which were shown to have Ki values of $2.0 \times 10^{-8}$M to $3 \times 10^{-9}$M respectively.

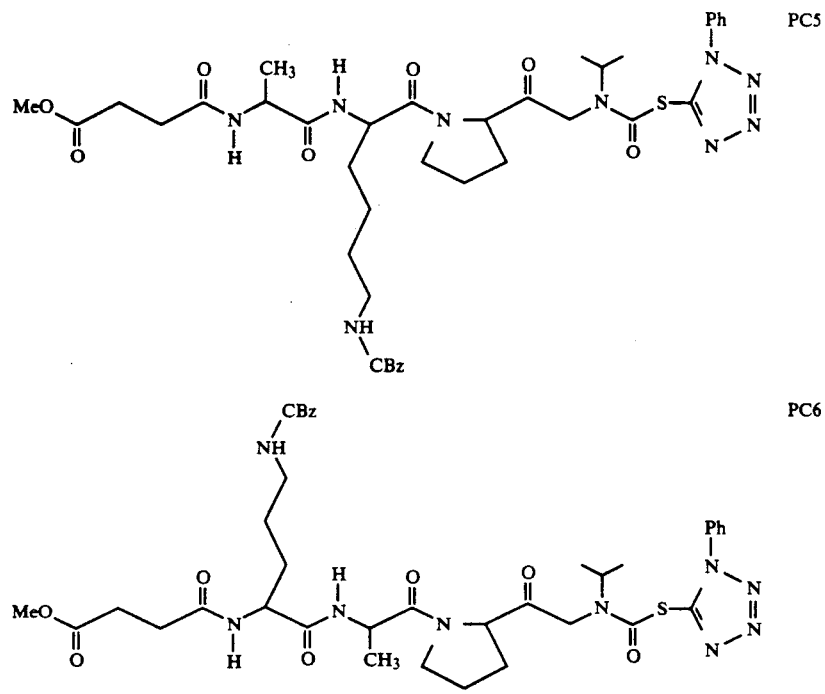

The coupling of the intermediate 7 with the compound 54 results in the elastase enzyme inhibitory compound PC5. The coupling of compound 12 with compound 54 results in the elastase enzyme inhibitory com-

TABLE 3
Effect of Stereochemistry at $P_2$ on the HLE Inhibitory Activity

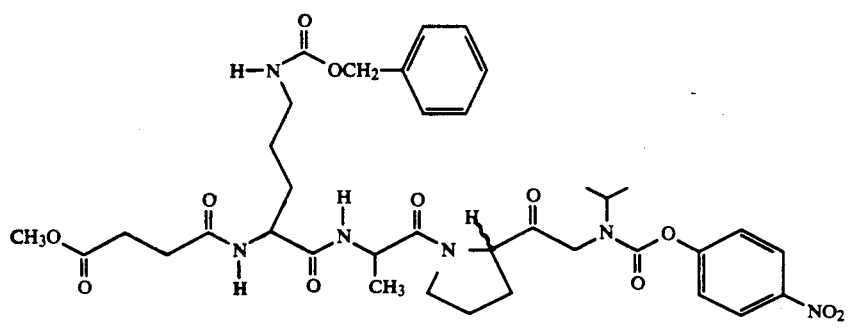

| Compound (46) | $K_i$ value[a] (μM) | $k_{obs}$[b,c] (s$^{-1}$) | (M$^{-1}$s$^{-1}$) | $k_{obs}$/[I][c] |
|---|---|---|---|---|
| L-L-L | 0.65 | 0.376 | | 8237 |
| L-L-D-proline | 7.95 | 0.021 | | 461 |
| L-L-DL[d] | 0.42 | 0.437 | | 9587 |

[a]$K_i$ value was determined by steady state kinetics.
[b][I] = 7.6 × 10$^{-7}$ M, [E] = 7.6 × 10$^{-8}$ M.
[c]First and second order rate constants were determined by pre-steady state inhibition kinetics.
[d]50:50 mixture of two inhibitors, each contributing 3.8 × 10$^{-7}$ M.

Extremely highly potent inhibitors of the enzyme elastase are obtained by replacing the p-nitrophenyl pound PC6. The synthesis of these compounds are depicted in Scheme 6 below.

Scheme 6
Synthesis of PC5 and PC6
Preparation of thiocarbamate portion.

-continued
Scheme 6
Synthesis of PC5 and PC6
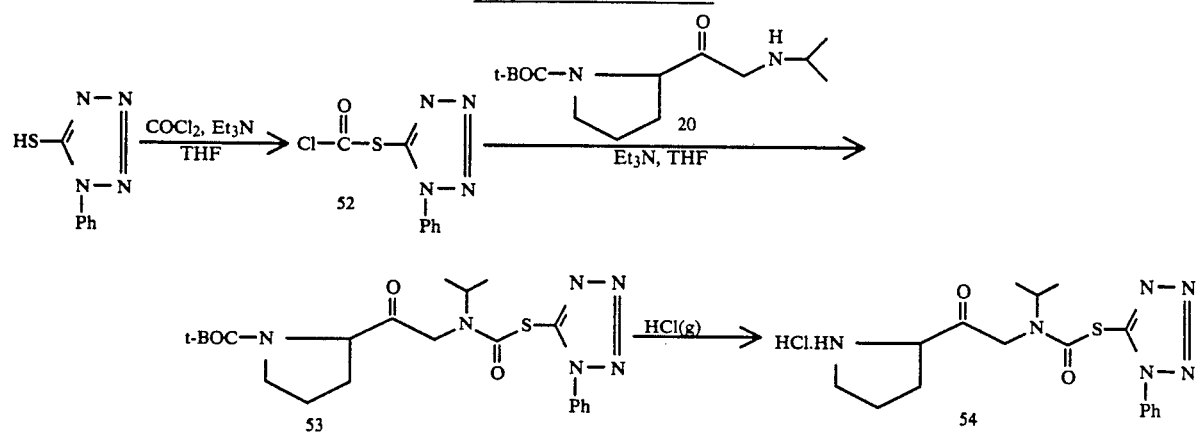
preparation of PC5
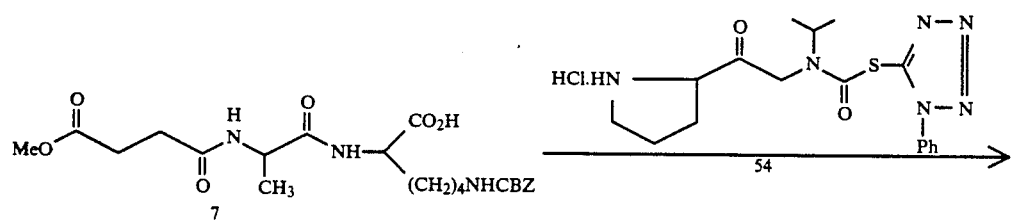
Preparation of PC6
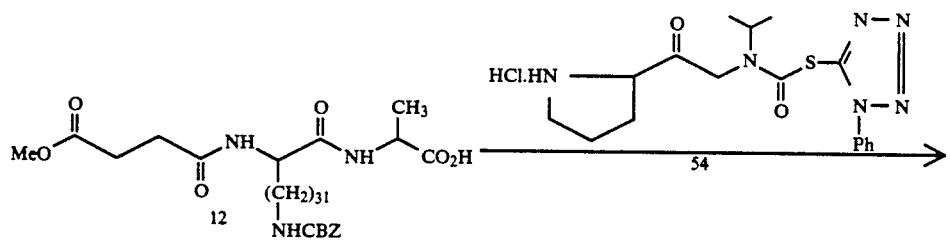
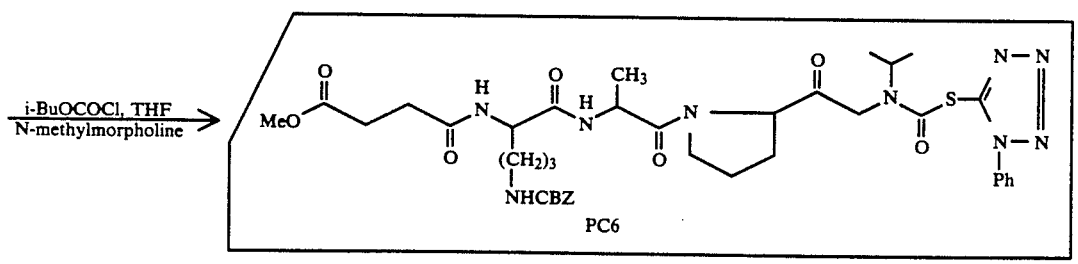
*CBZ: —C(=O)—O—CH₂Ph The conditions for conducting the various steps encompassed by these methods are known in the art and to an artisan in the field.

As pointed out above, the compounds of the invention may be employed as specific active site directed inhibitors of the enzyme, elastase. For this purpose, the compounds are preferably combined with a pharmaceutically acceptable carrier for administration by injection or in the oral form. Conventional adjuvant and carriers may be employed in combination with about 0.001 to 2.0 weight percent of the active compound. The compounds may be administered to animals or humans at about 10 mg/kg, preferably an average amount of about 6 mg/kg.

The following examples illustrate preferred embodiments of the invention but the invention is not considered to be limited thereto. In the examples and throughout this specification, parts are by weight unless otherwise indicated.

In synthesis of the compounds of the invention, melting points were determined on a Thomas-Hoover Uni-Melt apparatus and are uncorrected. $^1$H NMR spectra were obtained using a Varian EM-360 (60 MH$_2$O or EM-390) (90 MH$_2$) spectrometer. Infrared (IR) spectra were recorded on a Perkin-Elmer 567 spectrophotometer. Microanalyses were performed by Atlantic Microlab, Inc., Atlanta, Ga. or by Micro Analysis, Inc., Wilmington, Del.

Reactions were routinely followed by thin layer chromatography (TLC) using Whatman MK6F silica gel plates. Spots were detected by UV (254 nm), iodine or HBr-Ninhydrin spraying. Column chromatography was carried out using Silica Gel 60 from E. Merck, Darmstadt, Germany. All compounds were identified by spectral data and elemental analysis.

Having now generally described this invention, the same will be better understood by reference to certain specific examples, which are included herein for purposes of illustration only and are not intended to be limiting of the invention or any embodiment thereof, unless so specified.

EXPERIMENTAL

EX. 1

Methyl succinimide succinate (2)

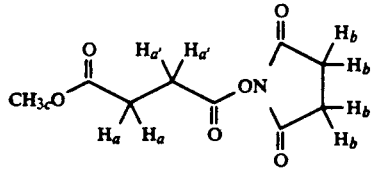

This compound was synthesized by a modified procedure of Digenis et al.[39]

A solution of 3-carbomethoxypropionyl chloride (5 g, 33.2 mmoles) and N-hydroxysuccinimide (3.8 g, 33.2 mmoles) in ethyl acetate (60 ml) was cooled to 5° C. While stirring, triethylamine (4.3 g, 33.2 mmoles) was slowly added to the cooled solution over a 15 min interval. The mixture was allowed to equilibrate to room temperature (22° C.) and react for an additional 3 h. The formed triethylamine salt was filtered, washed with ethyl acetate and the filtrate evaporated under vacuum. The powder was recrystallized from ethyl acetate/hexane to give 5.5 g (24.2 mmoles) (72% yield) of white needles mp 84°-86° C.). $^1$H-NMR (CDCl$_3$) δ 2.44(2H$_a$,app.t, J=8Hz); 2.64(2H$_{a'}$,app.t, J=8Hz); 2.86 (4H$_b$,s); 3.66(3H$_c$,s)ppm. IR (Nujol) 1840, 1800, 1775, 1725 cm$^{-1}$.

EX. 2 t-Butyl Methoxysuccinylalanine ester (3)

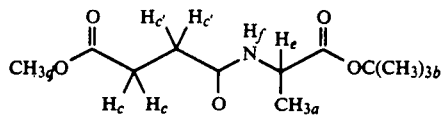

To an ice cooled suspension of the activated ester 2(3.6 g, 16 mmoles) and L-alanine t-butyl ester (2.3 g, 16 mmoles) in THF (50 mL), triethylamine (2.0 g, 16 mmoles) in THF (1 mL) was added dropwise. The progress of the reaction was monitored by TLC (10% methanol in chloroform) and stirred at 5° C. for 3.5 h. The precipitate was filtered under vacuum and washed with ethyl acetate. The residual oil, containing the product, was chromatographed using 40 g of silica gel column (2×50 cm). Impurities were eliminated by first passing 50 mL of methylene chloride and subsequently compound 3 was eluted with 2%. methanol in methylene chloride. Upon evaporation of the eluent solvent under reduced pressure the product was obtained. The latter was then crystallized from ethyl acetate/petroleum ether to give 2.9 g (11.3 mmoles) (71% yield) of a crystalline powder mp 91°-92° C. $^1$H-NMR (CDCl$_3$) δ 1.36(3H$_a$,d, J=8Hz); 1.46(9H$_b$,s); 2.44(2H$_c$,app.t, J=8Hz); 2.64(2H$_{c'}$,app.t, J=8Hz); 3.66(3H$_d$,s); 4.20–4.60(1H$_e$,m); 6.85(1H$_f$,m, rotamer of amide —NH)ppm. IR (CDCl$_3$) 3400, 1815, 1785, 1740 cm$^{-1}$.

EX. 3

Methoxysuccinylalanine (4)

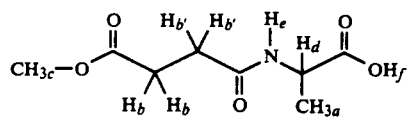

The t-butyl ester 3 was hydrolyzed by either of the following methods in good yield.

Procedure A:

Formic acid (98%)(1.5 mL) was added to an ice cooled solution of 3 (1.0 g, 3.9 mmoles) dissolved in ethyl acetate (10 mL). Hydrogen chloride gas was slowly bubbled through the cooled solution in two short (30 s) intervals 10 min apart. The solution was allowed to warm to room temperature and stirred for 2 h. The volatile liquids were evaporated in vacuo. The residue, containing the product, was chromatographed on 15 g of silica gel column (1×25 cm). The product 4 was eluted with 4% methanol in methylene chloride. Upon evaporation of the eluent solvent under reduced pressure 0.77 g (3.8 mmoles) (98% yield) of a transparent oil was obtained.

Procedure B:

A solution of 3 (1.0 g, 3.9 mmoles) in glacial acetic acid (5 mL) at room temperature was slowly diluted with 30% HBr in acetic acid (5 mL) and stirred for 30 min. The reaction was stopped by the addition of ice-water (15 mL) and the fine suspension was extracted with methylene chloride (5×25 mL). The organic layer was washed with brine, dried (5 g of MgSO$_4$), and the solvent was azeotropically removed under vacuum using n-heptane. The product was chromatographically purified as described in Procedure A, to give 0.77 g (3.8 mmoles) (98% yield) of a transparent oil. $^1$H-NMR (CDCl$_3$) δ 1.36(3H$_a$,d, J=8Hz); 2.56(4H$_{b,b'}$,app.t, J=8Hz); 3.66(3H$_c$,s);4.20–4.60(1H$_d$,m); 6.56(1H$_e$,m, rotamer of amide —NH); 9.50(1H$_f$,s)ppm IR (CHCl$_3$) 3280, 1735, 1690, 1630, 1540 cm$^{-1}$.

EX. 4

N$_α$-Methoxysuccinylalanyl-N$_ε$-benzoyllysine (5)

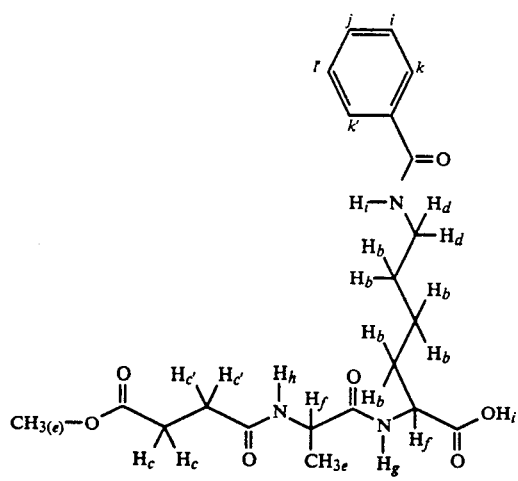

This compound was prepared from N$_ε$-benzoyl-L-lysine (not the phenacyl ester) according to an analogous procedure to that described for 6, with the following changes: the solvent was changed to DMF, the reaction time was extended to 24 h and the eluting solvent was changed to 8% methanol in chloroform. Upon evaporation of the eluent solvent under reduced pressure 0.37 g (0.85 mmoles) (47% yield) of a transparent oil was obtained. $^1$H-NMR (CDCl$_3$) δ 1.36(3H$_a$,d, J=8Hz); 1.50–1.86(6H$_b$,m); 2.56(4H$_{c,c'}$,app. t, J=8Hz); 3.23(2H$_d$,m); 3.66(3H$_e$,s); 4.00–4.70(2H$_f$,m); 5.80(1H$_g$,m, rotamer of amide —NH); 7.23(1H$_h$,m, rotamer of amide —NH); 7.34(2H$_{i,i'}$,app. dd, J$_{ik}$=8Hz, J$_{ii'}$=2Hz); 7.43(1H$_j$,app. dd, J$_{ji}$=8Hz, J$_{jk}$=2Hz); 7.86(2H$_{k,k'}$,app. dd,J$_{ki}$=8Hz,J$_{kj}$=2Hz); 8.10(1H$_l$,m, rotamer of amide —NH); 9.56(1H$_m$,s)ppm. IR (CHCl$_3$) 3330, 1730, 1645, 1600, 1540 cm$^{-1}$.

EX. 5

N$_α$-Methoxysuccinylalanyl-N$_ε$-carbobenzoxylysine phenacyl ester (6)

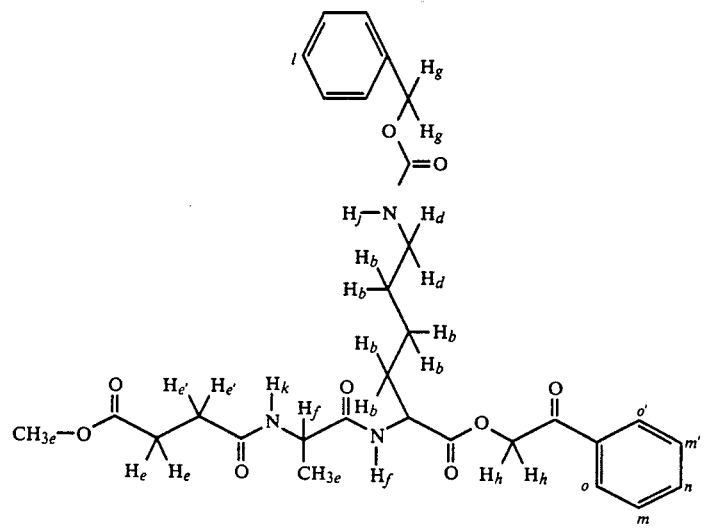

Methoxysuccinylalanine (4) (0.37 g, 1.8 mmoles) and N-hydroxysuccinimide (0.2 g, 1.8 mmoles) were mixed in THF (3 mL) and cooled to 5° C. A concentrated solution of N,N'-dicyclohexylcarbodiimide (0.4 g, 1.8 mmoles) in THF was added dropwise to the cooled solution. The suspension was stirred for 14 h at 5° C., and the precipitated urea formed was filtered under vacuum. The filtrate was cooled to 5° C. and used in the next reaction without further purification.

To a mixture of N$_ε$-carbobenzoxylysine phenacyl ester hydrochloride (35) (0.7 g, 1.7 mmoles) and the above N-hydroxysuccinimide ester in cooled THF (7 mL), triethylamine (0.17 g, 1.7 mmoles) in THF (0.5 mL) was added dropwise. A solution was observed for a short period of time before a precipitate was formed. The progress of the reaction was monitored by TLC (10% methanol in chloroform). Upon completion of the reaction (4 h), the formed triethylamine salt was filtered, washed with ethyl acetate and the filtrate evaporated under vacuum. The residue, containing the product, was chromatographed on 15 g of silica gel column (1×25 cm). Impurities were eliminated by first passing 50 mL of methylene chloride and subsequently the compound was eluted with 2% methanol in methylene chloride. Upon evaporation of the eluent solvent under reduced pressure a hygroscopic product was obtained. The latter was then recrystallized from ethyl acetate/diethylether to give 0.8 g (1.3 mmoles) (84% yield) of a crystalline powder, mp 114°–116° C. $^1$H-NMR (CDCl$_3$) δ 1.36(3H$_a$,d, J=8Hz); 1.50–2.20(6H$_b$,m); 2.44(2H$_c$,app. t, J=8Hz); 2.64(2H$_{c'}$,app.t, J=8Hz); 3.23(2H$_d$, m); 3.66(3H$_e$,s); 4.30–4.90(2H$_f$,m); 5.10(2H$_g$,s); 5.46(2H$_h$,s); 5.80(1H$_i$,m, rotamer of amide —NH); 6.56(1H$_j$,m, rotamer of amide —NH); 7.10(1H$_k$,m, rotamer of amide —NH); 7.40(5H$_l$,s); 7.63(3H$_{m,m',n}$,app. dd, J$_{mo}$=8Hz, J$_{mm'}$=2Hz); 8.06(2H$_{o,o'}$,app. dd, J$_{om}$=8Hz, J$_{on}$=2Hz)ppm. IR (CHCl$_3$) 3330, 1755, 1730, 1645, 1600, 1540 cm$^{-1}$.

EX. 6

$N_\alpha$-Methoxysuccinylalanyl-$N_\epsilon$-carbobenzoxylysine (7)

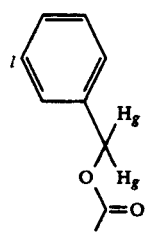

Small portions of zinc metal (total 2 g) were added over a 1 h period to a solution of phenacyl ester 6 (0.6 g, 1.1 mmoles) in glacial acetic acid (10 mL). The reaction was completed within one additional hour of stirring at room temperature. The suspension was diluted with 20% methanol in chloroform (50 mL), filtered under vacuum and the precipitate washed with 50 mL of 20% methanol in chloroform. The filtrate, containing the product, was evaporated under reduced pressure. The residue was partially dissolved in 5% methanol in chloroform and filtered to remove the zinc oxide. The second filtrate was evaporated under reduced vacuum to an impure oil. The latter was dissolved in methylene chloride and chromatographed on 10 g of silica gel column (1×25 cm). Impurities were eliminated by first passing 100 mL of 2% methanol in methylene chloride and subsequently compound 7 was eluted with 5% methanol in methylene chloride. Upon evaporation of the eluent solvent under reduced pressure an oil with a tendency to foam under vacuum was obtained. The product was crystallized from ethyl acetate/hexane to give 0.37 g (0.74 mmole)(74% yield) of a crystalline white powder, mp 116°–118° C. $^1$H-NMR (CDCl$_3$) δ 1.36(3H$_a$,d, J=8Hz); 1.40–2.20(6H$_b$,m); 2.56(4H$_{c,c'}$,app. t, J=8Hz); 3.23(2H$_d$,m); 3.66(3H$_e$,s); 4.30–4.90(2H$_f$,m); 5.10(2H$_g$,s); 5.60(1H$_h$,m, rotamer of amide —NH); 6.80–7.20(2H$_{i,i'}$,m, rotamer of amide —NH); 7.34(5H$_j$,s); 9.60(1H$_k$,s)ppm. IR (CHCl$_3$) 3330, 1730, 1710, 1590, 1540 cm$^{-1}$.

EX. 7

$N_\alpha$-Methoxysuccinylalanyl-$N_\delta$-carbobenzoxyornithine phenacyl ester (8)

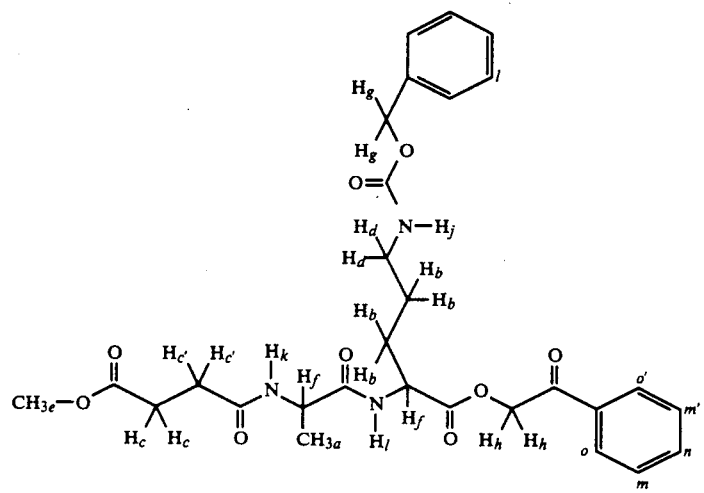

The title compound was prepared from $N_\delta$-carbobenzoxy-L-ornithine phenacyl ester hydrochloride following an analogous procedure to that described for 6. The product was crystallized from ethyl acetate/diethyl ether to give 0.46 g (0.8 mmole) (46% yield) of a crystalline powder mp 112°–113° C. $^1$H-NMR (CDCl$_3$) δ 1.36(3H$_a$,d,J=8Hz); 1.40–2.20(4H$_b$,m); 2.44(2H$_c$,app. t, J=8Hz); 2.64(2H$_{c'}$,app. t, J=8Hz); 3.18(2H$_d$,m); 3.66(3H$_e$,s); 4.36–5.00(2H$_f$,m); 5.10(2H$_g$,s); 5.46(2H$_h$,s); 5.80(1H$_i$,m, rotamer of amide —NH); 6.56(1H$_j$,m, rotamer of amide —NH); 7.10(1H$_k$,m, rotamer of amide —NH); 7.34(5H$_l$,s); 7.63(3H$_{m,m',n}$,app. dd, J$_{mo}$=8Hz, J$_{mm'}$=2Hz); 8.06(2H$_{o,o'}$,app. dd, J$_{om}$=8Hz, J$_{on}$=2Hz)ppm. IR (CHCl$_3$) 3330, 1755, 1730, 1645, 1600, 1540 cm$^{-1}$.

EX. 8

$N_\alpha$-Methoxysuccinylalanyl-$N_\delta$-carbobenzoxyornithine (9)

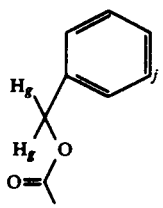

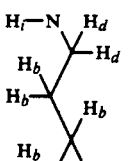
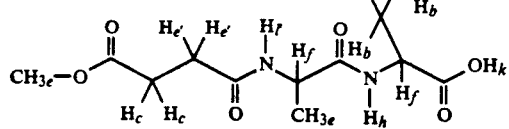

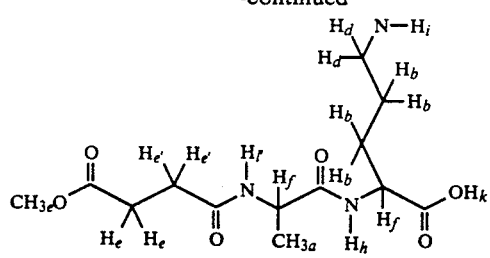

This compound was prepared from 8 according to an analogous procedure to that described for 7. Upon evaporation of the eluent solvent under reduced pressure 0.3 g (0.75 mmole)(68% yield) of a transparent oil was obtained. $^1$H-NMR (CDCl$_3$) δ 1.36(3H$_a$,d, J=8Hz); 1.40–1.90(4H$_b$,m); 2.56(4H$_{c,c'}$,app. t, J=8Hz); 3.23(2H$_d$,m); 3.66(3H$_e$,s); 4.40–4.80(2H$_f$,m); 5.10(2H$_g$,s); 6.80–7.10(2H$_i$,m, rotamer of amide —NH); 7.34(5H$_j$,s); 10.10(1H$_k$,s)ppm. IR (CHCl$_3$) 3330, 1730, 1710, 1590, 1540 cm$^{-1}$.

EX. 9

N$_\alpha$-Methoxysuccinyl-N$_\delta$-Carbobenzoxyornithine (10)

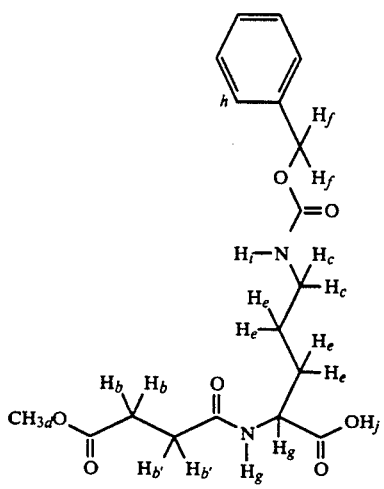

A suspension of 2(0.86 g, 3.8 mmoles) and N$_\delta$-carbobenzoxy-L-ornithine (1 g, 3.8 mmoles) in DMF were stirred during and after the addition of triethylamine (0.38 g, 3.8 mmoles) at room temperature. The progress of the reaction was monitored by TLC (10% acetic acid in ethyl acetate), upon completion of the reaction (24 h), the formed triethylamine salt was filtered and the filtrate coevaporated with toluene under vacuum. The residue, containing the product, was dissolved in a 50:50 mixture of ethyl acetate/0.001M aqueous HCl (30 mL). The organic layer was washed with water (30 mL) and brine (30 mL); dried (5 g of MgSO$_4$) and evaporated under reduced pressure. The residue was chromatographed on 30 g of silica gel column (2×50 cm). The desired product was eluted with 4% methanol in chloroform. Upon evaporation of the eluent solvent under reduced pressure, 1.4 g (3.6 mmoles) (96.7% yield) of an oil was obtained. The phenacyl ester derivative was recrystallized from ethyl acetate/hexane to give a crystalline powder mp 112°–113° C. $^1$H-NMR (CDCl$_3$) δ 1.50–2.00(4H$_a$,m); 2.44(2H$_b$,app. t, J=8Hz); 2.64(2H$_{b'}$,appt. t, J=8Hz); 3.23(2H$_c$,m); 3.66(3H$_d$,s); 4.30–4.80(1H$_e$,m); 5.10(2H$_f$,s); 7.20(1H$_g$,m, rotamer of amide —NH); 7.40(5H$_h$,s); 8.13(1H$_i$,m, rotamer of amide —NH); 9.46(1H$_j$,s)ppm. IR (CHCl$_3$) 3320, 1720, 1700, 1660, 1540 cm$^{-1}$.

EX. 10

N$_\alpha$-Methoxysuccinyl-N$_\delta$-carbobenzoxyornithylalanine t-butyl ester (11)

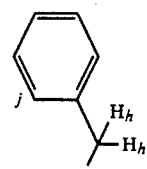

This compound was prepared from 10 according to an analogous procedure to that described for 14. The product (11) was crystallized from ethyl acetate/hexane to give 1.7 g (3.3 mmoles) (87% yield) of a white crystalline powder mp 133°–135° C. $^1$H-NMR (CDCl$_3$) δ 1.36(3H$_a$,dd, J=8Hz); 1.46(9H$_b$,s); 1.50–2.20(4H$_c$,m); 2.44(2H$_d$,app. t, J=8Hz); 2.64(2H$_{d'}$,app. t, J=8Hz); 3.23(2H$_e$,m); 3.66(3H$_f$,s); 4.00–4.52(2H$_g$,m); 5.10(2H$_h$,s); 6.80–7.20(3H$_i$,m, rotamer of amide —NH); 7.40(5H$_j$,s)ppm. IR (CHCl$_3$) 3330, 1735, 1725, 1590, 1540 cm$^{-1}$.

EX. 11

N$_\alpha$-Methoxysuccinyl-N$_\delta$-carbobenzoxyornithylalanine (12)

This compound was prepared from 11 according to an analogous procedure to that described for 15. The product (12) was crystallized from ethyl acetate/hexane to give 0.2 g (0.5 mmole) (48% yield) of a crystalline powder, mp 147°–148° C. $^1$H-NMR (CDCl$_3$)δ

1.36(3H$_a$,d, J=8Hz); 1.50–2.20(4H$_b$,m); 2.44(2H$_c$,app. t, J=8Hz); 2.64(2H$_c$,app. t, J=8Hz); 3.23(2H$_d$,m); 3.66(3H$_e$,s); 4.00–4.52(2H$_f$,m); 5.10(2H$_g$,s); 6.56(1H$_h$,m, rotamer of amide —NH); 6.80–7.20(2H$_i$,m, rotamer of amide —NH); 7.34(5H$_j$,s); 9.36(1H$_k$,s)ppm. IR(CHCl$_3$) 3330, 1730, 1645, 1590, 1540cm$^-$.

EX. 12

N$_\alpha$-Methoxysuccinyl-N$_\epsilon$-carbobenzoxylysine (13)

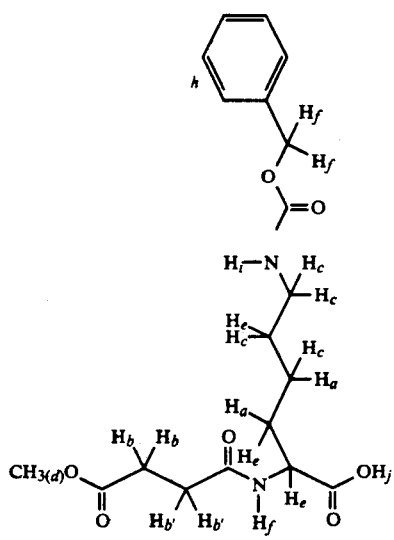

13

This compound was prepared from N$_\epsilon$-carbobenzoxy-L-lysine according to an analogous procedure to that described for 10. The product was crystallized from chloroform/hexane to give 1.35 g (3.42 mmoles) (90% yield) of a crystalline powder, mp 85°–86° C. $^1$H-NMR(CDCl$_3$)δ 1.50–2.00(6H$_a$,m); 2.44(2H$_b$,app. t, J=8Hz); 2.64(2H$_b$,app. t, J=8Hz); 3.23(2H$_c$,m); 3.66(3H$_d$,s); 4.30–4.80(1H$_e$,m); 5.10(2H$_f$,s); 7.20(1H$_g$,m, rotamer of amide —NH); 7.40(5H$_h$,s); 8.13(1H$_i$,m, rotamer of amide—NH); 9.46(1H$_j$,s)ppm. IR(CHCl$_3$) 3320, 1720, 1705, 1660, 1535 cm$^{-1}$. Elemental analysis cal'd for C$_{19}$H$_{26}$N$_2$O$_7$: C,57.87;H,6.64;N,7.10. Found: C,57.87;H,6.67;N,7.09.

EX. 13

N$_\alpha$-Methoxysuccinyl-N$_\epsilon$-carbobenzoxylysylalanine t-butyl ester (14)

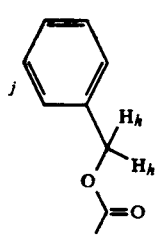

14

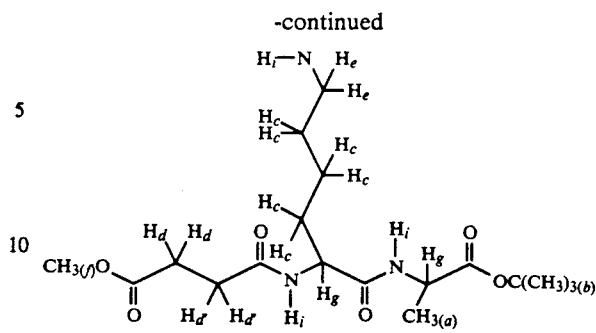

The carboxylic acid function of 13 (3.8 mmoles) was activated with N-hydroxysuccinimide (0.4 g, 3.8 mmoles) using N,N'-dicyclohexylcarbodiimide (0.8 g, 3.8 mmoles) in THF at 0° C. The cold reaction was stirred for one hour and stored in the refrigerator overnight (14 h). The precipitated urea was filtered under vacuum and washed with a small amount of THF.

L-Alanine t-butyl ester (0.7 g, 3.8 mmoles) was added as a solid to an ice-cooled THF (7 mL) solution of the activated ester (above). Triethylamine (0.38 g, 3.8 mmoles) in THF (0.5 mL) was added dropwise (10 min) to the fine suspension. The formed precipitate was filtered after 1 h and the filtrate evaporated under reduced pressure. The residue, containing the product, was chromatographed on 20 g of silica gel column (1×50 cm). Impurities were eliminated by first passing 50 mL of methylene chloride and subsequently the compound was eluted with 3% methanol in methylene chloride. Upon evaporation of the eluent solvent under reduced pressure an oil was obtained. The latter was crystallized from ethyl acetate/hexane to give 1.67 g (3.1 mmoles) (82% yield from 11 of white crystalline powder, mp 155°–157° C. $^1$H-NMR (CDCl$_3$) δ 1.36(3H$_a$,dd, J=8Hz); 1.46(9H$_b$,s); 1.50–2.20(6H$_c$,m); 2.44(2H$_d$,app. t, J=8Hz); 2.64(2H$_{d'}$,app. t, J=8Hz); 3.23(2H$_e$,m); 3.66(3H$_f$,s); 4.00–4.52(2H$_g$,m); 5.10(2H$_h$,s); 6.80–7.20(-3H$_i$,m, rotamer of amide —NH); 7.40(5H$_j$,s)ppm. IR(CHCl$_3$) 3330, 1735, 1725, 1590, 1540 cm$^{-1}$. Elemental analysis cal'd for C$_{25}$H$_{37}$N$_3$O$_9$: C,61.08;H,7.59;N,8.55. Found: C,61.08;H,7.60;N,8.53.

EX. 14

N$_\alpha$-Methoxysuccinyl-N$_\epsilon$-carbobenzoxylysylalanine (15)

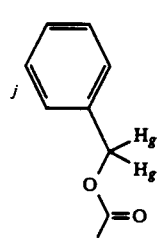

15

3.66(3H$_e$,s); 4.10–4.70(2H$_f$,m); 6.60–7.10(2H$_g$,m, rotamer of amide —NH); 7.34(2H$_{h,h'}$,app.dd, J$_{hi}$=8Hz, J$_{hh'}$=2Hz); 7.43(1H$_i$,app.dd, J$_{ih}$ =8Hz, J$_{ij}$ =2Hz); 7.83(2H$_{j,j'}$,app.dd, J$_{jh}$=8Hz, J$_{ji}$=2Hz); 8.10(1H$_k$,m, rotamer of amide —NH); 9.60(1H$_l$,s)ppm. IR (CHCl$_3$) 3330, 1730, 1630, 1590, 1540, 1460, 1380 cm$^{-1}$.

EX. 18

Preparation of an ether alcoholic solution of diazomethane, with a Diazald distillation kit Ethanol, 95% (8 mL) was added to a solution of potassium hydroxide (1.79 g) in water (2.7 mL) in a 50 mL distilling flask fitted with a dropping funnel and an efficient condenser set downward for distillation. The condenser was connected to two receiving flasks in series, the second containing 20 mL of diethyl ether. The inlet tube of the second receiver was dipped below the surface of the ether. Both receivers were cooled to 0° C. The flask containing the alkali solution was heated in a water bath to 65° C., and a solution of Diazald (N-methyl-N-nitroso-p-toluenesulfonamide) (7.2 g, 33.0 mmole) in ether (70 ml) was added through the dropping funnel over about 30 min. The rate of distillation was approximately equal to the rate of addition. When the dropping funnel was empty, another 20 mL of ether was added slowly and the distillation was continued until the distilling ether was colorless. The combined ethereal distillate contained about 1 g (33.0 mmoles) of diazomethane based on the amount of Diazald used. Extreme care is warranted during and after the preparation of diazomethane. Care must be taken to avoid possible explosions by thoroughly checking the glassware for cracks and scratches, heating the alkali solution with a water bath (not to exceed 75° C.) and keeping the generated diazomethane solutions at or below 5° C.

EX. 19

N-t-Boc-L-prolyl chloromethyl ketone (19)

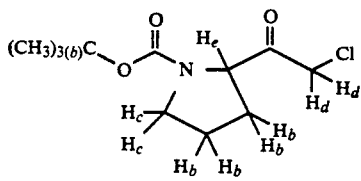

The procedure of Digenis et al.[39] was followed for the preparation of compound 19.

Isobutylchloroformate (2.1 g, 15.3 mmoles) was added to a solution of triethylamine (1.55 g, 15.3 mmoles) and t-Boc-L-proline (3.3 gm, 15.3 mmoles) in diethyl ether (30 mL) was cooled to −15° C. The reaction mixture was stirred at this temperature for 10 min, at which time a cooled solution (0° C.) of diazomethane (1 g, 32.4 mmoles) in diethyl ether (200 mL) was added. The vessel, equipped with a calcium sulfate drying tube, was stirred at 0° C. in the hood overnight (14 h). The organic layer was washed subsequently with saturated bicarbonate solution (30 mL), water (30 mL) and brine (30 mL). After drying with 15 g of MgSO$_4$, the solvent was evaporated under reduced pressure to yield of yellow oil.

Hydrogen chloride gas was bubbled through an ice cooled solution of the yellow oil (N-t-Boc-L-proyl azomethyl ketone) in diethyl ether (50 mL) for 60s. The reaction was stopped after 10 min by diluting with cooled diethyl ether (50 mL) and evaporated under vacuum. The residue, containing the product, was chromatographed on 50 g of silica gel column (3×75 cm) Impurities were eliminated by first passing 100 mL of 10% hexane in chloroform and subsequently the compound was eluted with chloroform. Upon evaporation of the eluent solvent under reduced pressure a transparent oil was obtained. The latter (19) was then crystallized from chloroform/hexane to give 3.1 g (12.5 mmoles) (82% yield) of colorless crystals m.p. 47°–49° C. $^1$H-NMR (CDCl$_3$) δ 1.46(9H$_a$,s); 1.86–2.16(4H$_b$,m); 3.33–3.76(2H$_c$,m); 4.36(2H$_d$,s); 4.40–4.80(1H$_c$,m)ppm. IR (Nujol) 1740, 1690 cm$^{-1}$. Elemental Analysis Cal'd. for C$_{11}$H$_{18}$ClNO$_3$: C,53.33;H,7.32;N,5.65. Found,C,53.46;H,7.35;N,5.56.

The NMR, IR and Elemental analysis were found to be identical to those reported by Digenis et al.[39].

EX. 20

N-[(N-t-Boc-L-propyl)methyl]isopropylamine (20)

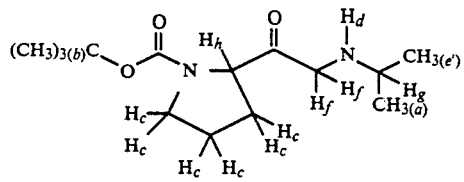

This compound was synthesized by a modified procedure of Digenis et al[39].

Isopropylamine (7.4 g, 125.0 mmoles) was slowly added to a cooled solution (0° C.) of 19 (3.1 g, 12.5 mmoles) in diethyl ether and stirred overnight at room temperature (14h). The salt formed was filtered and the filtrate evaporated under vacuum. The oil was chromatographed on 30 g of silica gel column (2×25 cm). Impurities were eliminated by first passing 50 mL of 1% methanol in chloroform and subsequently the compound was eluted with 5% methanol in chloroform. Upon evaporation of the eluent solvent under reduced pressure 3.1 gm (11.4 mmoles) (90.8% yield) of an oil was obtained. $^1$H-NMR(CDCl$_3$) δ 0.93–1.31(6H$_a$,app. d, J=7Hz); 1.46(9H$_b$,s); 1.86–2.16(4H$_c$,m); 2.83(1H$_d$,m); 3.30–3.73(5H$_{e,f,g}$,m); 4.30(1H$_h$,app.t,J=8Hz)ppm. I (CHCl$_3$)3330, 1695 cm$^{-1}$.

The NMR and IR of this compound were found to be identical to those reported by Digenis et al.[39].

EX. 21 p-Nitrophenyl-N-[(N-Boc-L-prolyl)methyl]-N-isopropyl-carbamate (21)

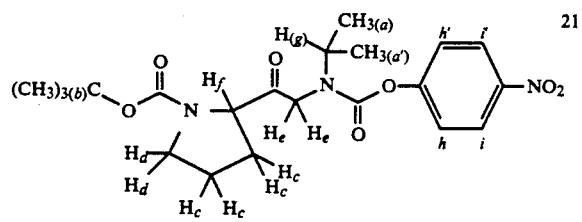

the procedure of Digenis et al.[39] was followed for the preparation of compound 21.

p-Nitrophenylchloroformate (2.75 g, 13.6 mmoles) was added as powder to an ice-cooled solution of 20 (3.1 g, 11.4 mmoles) in THF (10 mL) and triethylamine (1.15 g, 11.4 mmoles) at 5° C. The mixture was stirred at 5° C.

for 2 h, the formed triethylamine salt filtered and the filtrate evaporated under vacuum. The crude oil was dissolved in ethyl acetate and washed with water, 10% aqueous citric acid (30 mL), water (30 mL) and brine (30 mL); dried (10 g of MgSO$_4$) and evaporated under reduced pressure. The residue, containing the product, was dissolved in a small amount of chloroform and chromatographed on 40 g of silica gel column (2×50 cm). The impurities were eliminated by first passing chloroform and subsequently the compound was eluted with 50:1 chloroform in ethyl acetate. Upon evaporation of the eluent solvent under reduced pressure 4.6 g (10.7 mmoles) (94% yield) of a transparent oil was obtained. $^1$H-NMR (CDCl$_3$) δ 1.13(3H$_a$,app. d, J=8Hz); 1.20(3H$_{a'}$,add. d, J=8Hz); 1.46(9H$_b$,s); 1.86–2.16(4H$_c$,m); 3.56–3.84(2H$_d$,m); 4.20,4.32(2H$_e$, center of a set of dd, overlapping with another set, J=20Hz, rotamers of the CH$_{2(e)}$ geminal system); 4.50(2H$_f$, app. t, J=8Hz); 4.53–4.80(4H$_g$,m); 7.22(1H$_h$,app. d, J=10Hz); 7.26(1H$_{h'}$,app. d, J=10Hz); 8.22(1H$_i$,app. d, J=10Hz); 8.24(1H$_{i'}$,app. d, J=10Hz). IR (CHCl$_3$) 1740, 1710, 1690, 1595, 1520 cm$^{-1}$.

The NMR and IR for this compound were found to be identical to those reported by Digenis et al.[39]

EX. 22 p-Nitrophenyl-N-(L-Prolylmethyl)-N-isopropylcarbamate Hydrochloride (22)

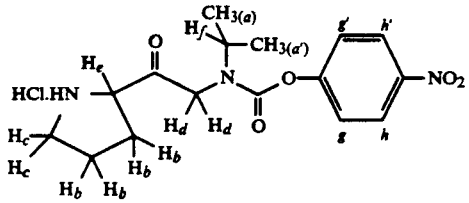

The procedure of Digenis et al. was followed for the preparation of compound 22.

Three additions of hydrogen chloride gas (30s each) were introduced at 10 min intervals to an ice-cooled ethyl acetate (20 mL) solution of 21 (1.6 g, 5.6 mmoles) and formic acid (98%) (2.4 mL). The solution was stirred at 5° C. for 1 h, then allowed to equilibrate to room temperature (1 h). The product was collected by vacuum filtration and washed with ethyl acetate. A second crop was collected after concentrating the solution. The latter was crystallized from ethanol/diethyl ether to give 1.46 g (3.8 mmoles) (68% yield) of a tan powder, mp 179°–182° C. (lit.[39] mp 190°–193° C.). $^1$H-NMR (DMSO-d$_6$) δ 1.13(3H$_a$,app. d, J=8Hz); 1.20(3H$_{a'}$,app. d, J=8Hz); 1.70–2.30(4H$_b$,m); 3.20–3.56(2H$_c$,m); 4.20(2H$_d$,m); 4.50(2H$_{e,f}$,m); 7.22(1H$_g$,app. d, J=10Hz); 7.26(1H$_{g'}$,app. d, J=10Hz); 8.22(1H$_h$,app. d, J=10Hz); 8.24(1H$_{h'}$,app. d, J=10Hz)ppm. IR (Nujol) 1740, 1720, 1610, 1595, 1520 cm$^{-1}$.

EX. 23 p-Nitrophenyl N-[Methoxysuccinyl-(N$_\epsilon$-carbobenzoxy)lysylalanyl-prolylmethyl]-N-isopropylcarbamate (44b, the LLD diastereomer)

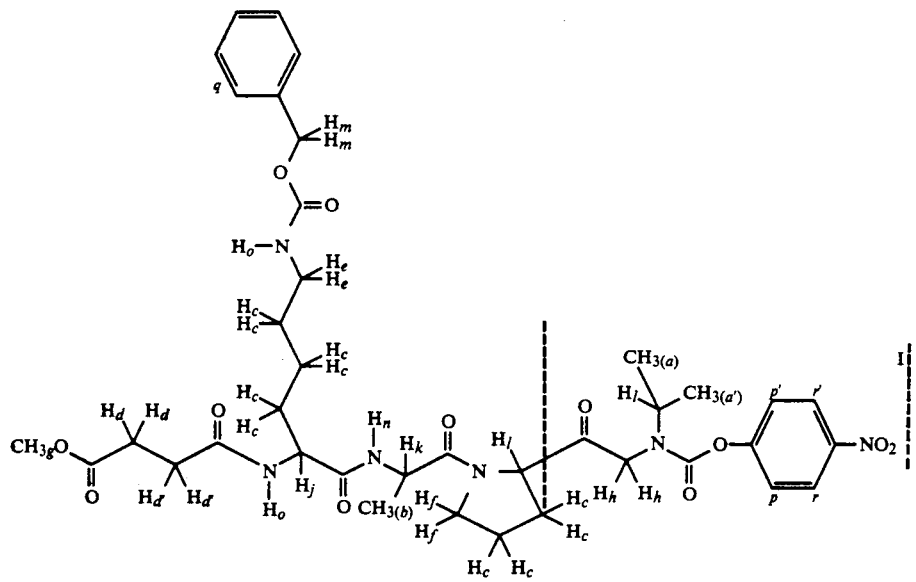

To a cooled solution (−15° C.) of 15 (0.85 mmoles) and N-methylmorpholine (0.85 mmoles) in THF (5 mL) isobutylchloroformate (0.13 g, 0.94 mmoles) in acetonitrile (3 mL) was added. After 10 min, 22 (0.4 g, 1 mmole) was added as a solid and N-methylmorpholine (0.1 g, 1 mmole) as an acetonitrile solution (2 mL). The reaction mixture was allowed to warm to 5° C. in 30 min and stirred (3 h). The reaction mixture was filtered, the filtrate was evaporated under vacuum and the residue was redissolved in methylene chloride (25 mL). The organic solvent was subsequently washed with water (25 mL), 10% aqueous citric acid (25 mL), water (25 mL) and brine (25 mL); dried (5 g of MgSO$_4$) and evaporated under reduced pressure. The residue, containing the product, was chromatographed on 10 g silica gel column (1×25 cm). The impurities were eliminated by first passing 25 mL of methylene chloride and 25 mL 2% methanol in methylene chloride. Upon evaporation of the eluent solvent under reduced pressure an amorphous powder was obtained. The amorphous powder containing 44a and 44b was dissolved in chloroform and applied to a preparaative TLC plate (100 mg/plate) and developed two to three times with 4% methanol in ethyl acetate. The two bands were separately scraped from the plate and extracted with 20% methanol in chloroform (3×25 mL). The eluent solvent was evaporated under reduced pressure to give an amorphous powder. The lower band was pure 44a. The desired product (44b) isolated as 0.23 g (0.3 mmoles)(35% yield) of a white amorphous powder, mp 46°–47° C., was obtained from the upper TLC band. $^1$H-NMR (CDCl$_3$) δ 1.13(3H$_a$,app.d, J=7Hz, rotamer of l); 1.20(3H$_{a'}$,app.d, J=7Hz, rotamer of l); 1.36(3H$_b$,d, J=8Hz); 1.40–2.22(10H$_c$,m); 2.44(2H$_d$,app.t, J=8Hz); 2.64(2H$_{d'}$,app.t, J=8Hz); 3.18(2H$_e$,m); 3.33(2H$_f$,app.t, J=8Hz); 3.66(2H$_g$,s); 4.30(2H$_h$, center of 2 sets of dd, J=20Hz, rotamer of the CH$_{2(h)}$ geminal system); 4.53(1H$_i$,app.t, J=8Hz); 4.63(1H$_j$,app.t, J=8Hz); 4.80(2H$_{k,l}$,m); 5.10(2H$_m$,s); 5.42(1H$_n$,m); 6.70–7.10(-2H$_o$,m, rotamer of amide —NH); 7.24(1H$_p$,app.d, J=10Hz, rotamer of l); 7.28(1H$_{p'}$,app.d, J=10Hz, rotamers of l); 7.34(5H$_q$,app.s); 8.20(1H$_r$,app.d, J=10Hz, rotamer of l); 8.25(1H$_{r'}$,app.d, J=10Hz, rotamer of l)ppm. IR (CHCl$_3$) 3310, 1730, 1650, 1520, 735, 700 cm$^{-1}$. Elemental analysis cal'd for C$_{38}$H$_{50}$N$_6$O$_{12}$: C,58.30;H,6.44;N,10.74. Found: C,58.19;H,6.50;N,10.64.

EX. 24 p-Nitrophenyl N-[Methoxysuccinyl-(N$_{68}$-carbobenzoxy)lysylalanyl-prolylmethyl]-N-isopropylcarbamate (44a, the LLL diastereomer)

44b. Tha amorphous powder containing 44a and 44b was dissolved in chloroform and applied to a preparative TLC plate (100 mg/plate) and developed two or three times with 4% methanol in ethyl acetate. The lower band contained 44a while the upper band contained 44b. The two bands were separately scraped from the plate, extracted with 20% methanol in chloroform (3×25 mL) and eluent solvent evaporated under reduced pressure. The desired product (44a) isolated as 0.33 g (0.43 mmoles) (50% yield) of a white amorphous powder, mp 50°–51° C., was obtained from the lower TLC band. $^1$H-NMR (CDCl$_3$) δ 1.06–1.28(6H$_{a,a'}$,m, rotamer of l); 1.32(3H$_b$,d, J=8Hz); 1.38–2.32(10H$_c$,m); 2.46(2H$_d$,app.t, J=8Hz); 2.64(2H$_{d'}$,app.t, J=8Hz); 3.20(2H$_e$,m); 3.36(2H$_f$,m); 3.66(3H$_g$,s); 4.20,432(2H$_h$, center of a set of dd, overlapping with another set, J=20Hz, rotamers of the CH$_{2(h)}$ geminal system); 4.53(1H$_i$,app.t, J=8Hz); 4.63(1H$_j$,app. t, J=8Hz); 4.80(2H$_{k,l}$,m); 5.10(2H$_l$,s); 5.42(1H$_m$,m); 6.36–7.08(2H$_n$,m, rotamers of amide —NH); 7.35(5H$_p$,app.s); 8.20(1H$_q$,app.d, J=10Hz, rotamers of l); 8.25(1H$_{q'}$,app.d,J=10Hz, rotamers of l)ppm. IR (CHCl$_3$) 3310, 1730, 1650, 1520, 735, 700 cm$^{-1}$. Elemental Analysis cal'd for C$_{38}$H$_{50}$N$_6$O$_{12}$: C,58.30; H,6.44; N,10.74. Found: C,58.47; H,6.48; N,10.67.

EX. 25 p-Nitrophenyl N-[Methoxysuccinyl-(N$_\epsilon$-benzoyl)lysylalanylprolylmethyl]-N-isopropylcarbamate (45b, the LLD diastereomer)

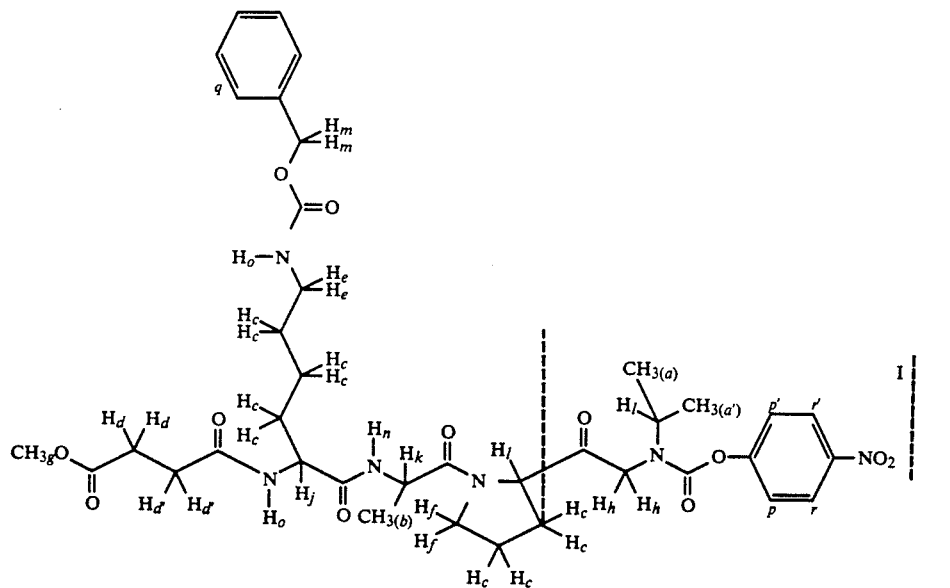

44a

The title compound was prepared from 15 and 22 following a procedure analogous to that described for

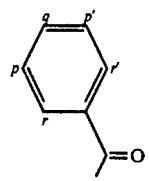

45b

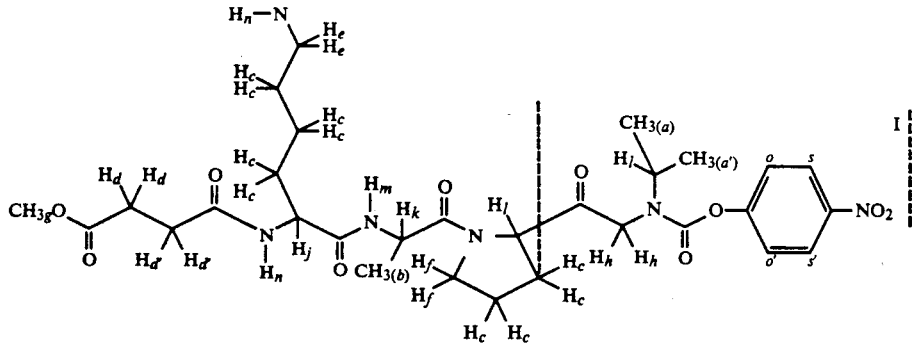

The title compound was prepared from 18 and 22 following a procedure analogous to that described for 44b. The amorphous powder containing 45a and 45b was dissolved in chloroform and applied to a preparative TLC plate (100 mg/ml) and developed two or three times with 15% isopropanol in chloroform. The lower band contained 45a while the upper band contained 45b. The two bands were separately scraped from the plate, extracted with 20% methanol in chloroform (3×25 mL) and eluent solvent evaporated under reduced pressure. The desired product (45b) isolated as 0.26 g (0.34 mmoles) (40% yield) of a white amorphous powder mp 63°-64° C. was obtained from the upper TLC band. $^1$H-NMR(CDCl$_3$) δ 1.13(3H$_a$,app.d,J=7Hz, rotamers of l); 1.20(3H$_{a'}$,app.d, J=7 Hz, rotamers of l); 1.36(3H$_b$,d,J=8Hz); 1.40-2.22(10H$_c$,m); 2.44(2H$_d$,app.t, J=8 Hz); 2.64(2H$_{d'}$,app.t, J=8 Hz); 3.18(2H$_e$,m); 3.33(2H$_f$,app.t , J=8Hz); 3.66(2H$_g$,s); 4.30(2H$_h$, center of 2 sets of dd, J=20Hz, rotamers of the CH$_{2(h)}$ geminal system); 4.53(1H$_i$,app.t, J=8Hz); 4.63(1H$_j$,app.t, J=8Hz); 4.80(2H$_{k,l}$,m); 5.42(1H$_m$,m); 6.70-7.10(2H$_n$,m, rotamers of amide —NH); 7.24(1H$_o$,app.d, J=10Hz, rotamers of l); 7.28(1H$_{o'}$,app.d, J=10Hz, rotamers of l); 7.34(2H$_{p,p'}$,app.dd, J$_{qp}$=8Hz, J$_{qr}$=2Hz); 7.43(1H$_q$,app.dd, J$_{qp}$=8Hz, J$_{qr}$=2Hz); 7.83(2H$_{r,r'}$,app.dd, J$_{rp}$=8Hz, J$_{rq}$=2Hz); 8.20(1H$_s$,app.d, J=10Hz, rotamers of l); 8.25(1H$_{s'}$,app.d, J=10Hz, rotamers of l)ppm. IR (CHCl$_3$) 3400, 1730, 1645, 1525, 1440, 1345, 1215, 750, 665 cm$^{-1}$. Elemental Analysis cal'd for C$_{37}$H$_{48}$N$_6$O$_{11}$: C,58.90;H,6.37;N,11.14. Found: C,58.59;H,6.76;N,10.24.

EX. 26 p-Nitrophenyl N-[Methoxysuccinyl-(N$_ε$-benzoyl)lysylalanylprolylmethyl]-N-isopropylcarbamate (45a, the LLL diastereomer)

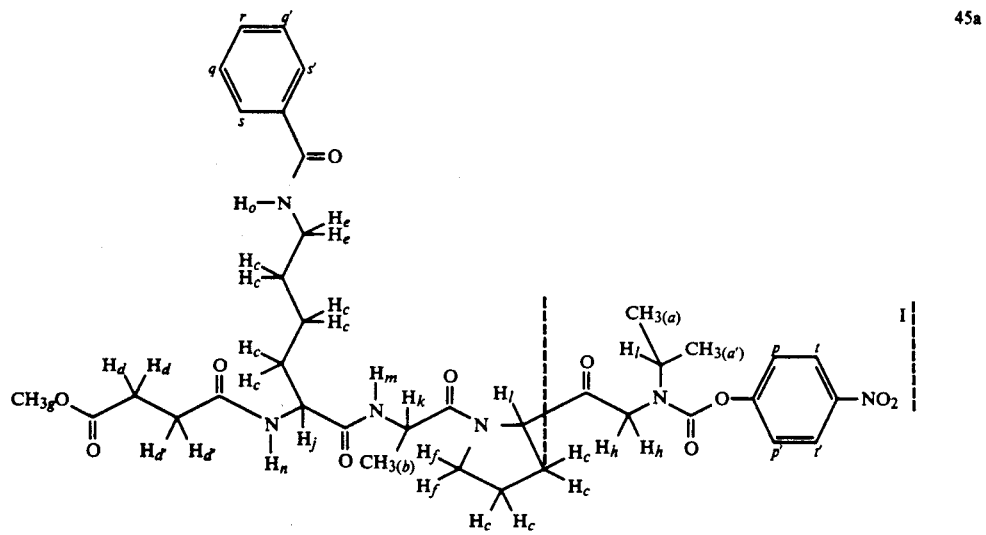

45a

The title compound was prepared from 18 and 22 followed a procedure analogous to that described for 44b. The amorphous powder containing 45a and 45b was dissolved in chloroform and applied to a preparative TLC plate (100 mg/plate) and developed two or three times with 15% isopropanol in chloroform. The lower band contained 45a while the upper band contained 45b. The two bands were separately scraped from the plate, extracted with 20% methanol in chloroform (3×25 mL) and eluent solvent evaporated under reduced pressure. The desired product (45a) isolated as 0.26 g (0.35 mmoles) (41% yield) of a white powder, mp 45°-46° C., was obtained from the lower TLC band. $^1$H-NMR (CDCl$_3$) δ 1.06-1.28(6H$_{a,a'}$,m, rotamers of l); 1.32(3H$_b$,d, J=8Hz); 1.38-2.32(10H$_c$,m); 2.46(2H$_d$,app.t, J=8Hz); 2.64(2H$_{d'}$,app.t,J=8Hz); 3.20(2H$_e$,m); 3.53-3.88(2H$_f$,m); 3.66(3H$_g$,s); 4.20,4.32(2H$_h$, center of a set of dd, overlapping with an other set, J=20Hz, rotamers of CH$_{2(h)}$ geminal system); 4.53(1H$_i$,app.t, J=8Hz); 4.63(1H$_j$,app.t, J=8Hz); 4.80(2H$_{k,l}$,m); 5.42(1H$_m$,m); 6.70-7.10(2H$_{n,o}$, m, rotamers of amide —NH); 7.24(1H$_p$,app.d, J=10Hz, rotamers of 1); 7.28(1H$_{p'}$,app.d, J=10Hz, rotamers of 1); 7.34(2H$_{q,q'}$,app.dd, J$_{qr}$=8Hz, J$_{qq'}$=2Hz); 7.43(1H$_r$,app.dd, J$_{rq}$=8Hz, J$_{rs}$=2Hz); 7.83(2H$_{s,s'}$,app.dd, J$_{sq}$=8Hz, J$_{sr}$=2Hz); 8.20(1H$_t$,app.d, J=10Hz, rotamers of 1); 8.25(1H$_{t'}$,app.d, J=10Hz, rotamers of 1). IR (CHCl$_3$) 3400, 1730, 1645, 1525, 1440, 1345, 1215, 750, 665 cm$^{-1}$. Elemental Analysis cal'd for C$_{37}$H$_{48}$N$_6$O$_{11}$: C,58.90;H,6.37;N,11.14. Found: C,59.18;H,6.76;N,11.24.

EX. 27 p-Nitrophenyl N-[Methoxysuccinyl-(N$_\delta$-carbobenzoxy) ornithylalanylprolylmethyl]-N-isopropylcarbamate (46b, the LLD diastereomer)

The title compound was prepared from 12 and 22 following a procedure analogous to that described for 44b. The amorphous powder containing 46a and 46b was dissolved in chloroform and applied to a preparative TLC plate (100 mg/plate) and developed two or three times with 10% isopropanol in chloroform. The lower band contained 46a while the upper band contained 46b. The two bands were separately scraped from the plate, extracted with 20% methanol in chloroform (3×25 mL) and eluent solvent evaporated under reduced pressure. The desired product (46b) isolated as 0.08 g (0.13 mmoles) (15% yield) of a white amorphous powder, mp 50°-51° C., was obtained from the upper TLC band. $^1$H-NMR (CDCl$_3$) δ 1.13(3H$_a$,app.d, J=7Hz, rotamers of 1); 1.20(3H$_{a'}$,app.d, J=7Hz, rotamers of 1); 1.36(3H$_b$,d, J=8Hz); 1.40-2.22(8H$_c$,m); 2.44(2H$_d$,app.t, J=8Hz); 2.64(2H$_{d'}$,app.t, J=8Hz); 3.18(2H$_e$,m); 3.33(2H$_f$,app.t, J=8Hz); 3.66(2H$_g$,s); 4.30(2H$_h$, center of 2 sets of dd, J=20Hz, rotamers of the CH$_{2(h)}$ geminal system); 4.53(1H$_i$,app.t, J=8Hz); 4.63(1H$_j$,app.t, J=8Hz); 4.80(2H$_{k,l}$,m); 5.10(2H$_m$,s); 5.42(1H$_n$,m); 6.70–7.10(2H$_o$,m, rotamers of amide -NH); 7.24(1H$_p$,app.d, J=10Hz, rotamers of 1); 7.28(1H$_{p'}$, app.d, J=10Hz, rotamers of 1); 7.34(5H$_q$,app.s); 8.20(1H$_r$,app.d, J=10Hz, rotamers of 1);

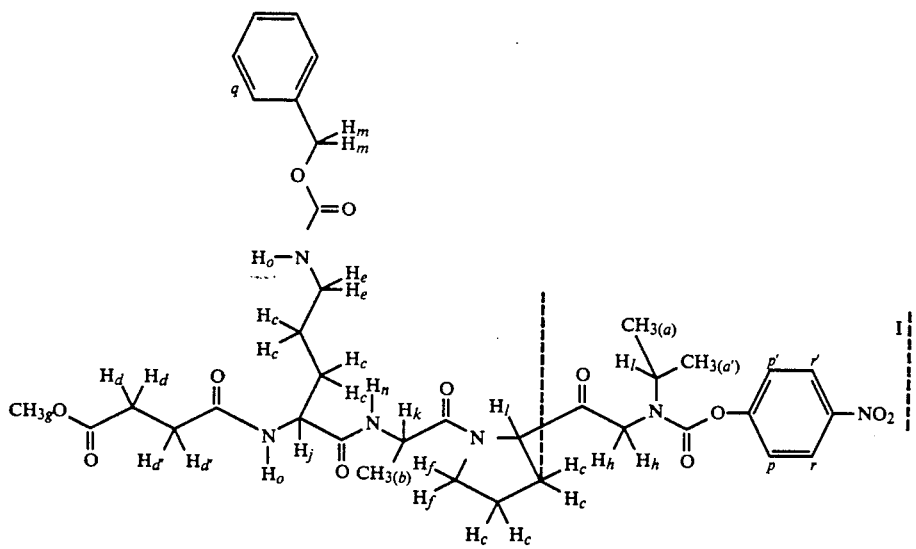

46b 8.25(1H$_{r'}$,app.d, J=10Hz, rotamers of 1)ppm. IR (CHCl$_3$) 3310, 1730, 1650, 1520, 735, 700 cm$^{-1}$. Elemental Analysis cal'd for C$_{37}$H$_{48}$N$_6$O$_{12}$: C,57.80; H,6.25; N,10.94. Found: C,57.42; H,6.36; N,11.82.

EX. 28 p-Nitrophenyl N-[Methoxysuccinyl-(N$_\delta$-carbobenzoxy)ornithylalanylprolylmethyl]-N-isopropylcarbamate (46a, the LLL diastereomer)

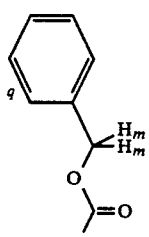

46a

-continued

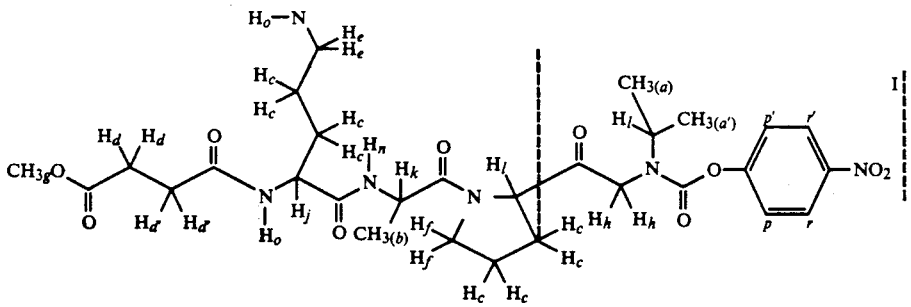

The title compound was prepared from 12 and 22 following a procedure analogous to that described for 44b. The amorphous powder containing 46a and 46b was dissolved in chloroform and applied to a preparative TLC plate (100 mg/plate) and developed two or three times with 10% isopropanol in chloroform. The lower band contained 46a while the upper band contained 46b. The two bands were separately scraped from the plate, extracted with 20% methanol in chloroform (3×25 mL) and eluent solvent evaporated under reduced pressure. The desired product (46a) isolated as 0.31 g (0.41 mmoles) (48% yield) of a white amorphous powder, mp 55°–56° C., was obtained from the lower TLC band. $^1$H-NMR (CDCl$_3$) δ 1.13(3H$_a$,app. d, J=7Hz, rotamer of l); 1.20(3H$_{a'}$,app. d, J=7Hz, rotamer of l); 1.36(3H$_b$,d, J=8Hz); 1.40–2.22(8H$_c$,M); 2.44(2H$_d$,app. t, J=8Hz); 2.64(2H$_{d'}$,app. t, J=8Hz); 3.18(2H$_e$,m); 3.33(2H$_f$,app.t, J=8 Hz); 3.66(2H$_g$,s); 4.30(2H$_h$, center of 2 sets of dd, J=20Hz, rotamers of the CH$_{2(h)}$ geminal system); 4.53(1H$_j$,app.t, J=8Hz); 4.63(1H$_j$, app.t, J=8Hz); 4.80(2H$_{k,l}$,m); 5.10(2H$_m$,s); 5.42(1H$_n$,m); 6.70–7.10(2H$_o$,m, rotamers of amide —NH); 7.24(1H$_p$, app. d, J=10 Hz, rotamers of l); 7.28(1H$_{p'}$,app.d, J=10Hz, rotamers of l); 7.34(5H$_q$,app. s); 8.20(1H$_r$,app.d, J=10Hz, rotamers of l); 8.25(1H$_{r'}$,app. d, J=10Hz, rotamers of l)ppm. IR (CHCl$_3$) 3310, 1730, 1650, 1520, 735, 700 cm$^{-1}$. Elemental Analysis cal'd for C$_{37}$H$_{48}$N$_6$O$_{12}$: C,57.80; H,6.25; N,10.94. Found: C,57.81; H,6.36; N,10.68.

EX. 29 p-Nitrophenyl N-[Methoxysuccinyl-(N$_δ$-benzoyl)ornithylalanylprolyl-methyl]-N-isopropylcarbamate (47, the LLD diastereomer)

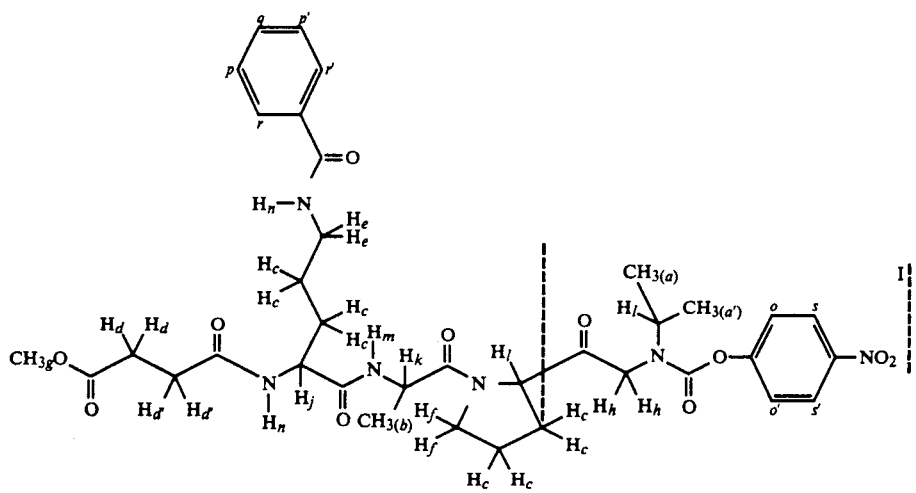

A solution of the diastereomers 46a and 46b (0.16 g, 0.2 mmole) in glacial acetic acid (0.3 mL) was diluted with 30% hydrogen bromide in acetic acid (0.3 mL) and stirred at room temperature for 90 min. The reaction was stopped by the addition of dry diethyl ether (10 mL) and the suspension decanted 4 times to produce a hygroscopic brown powder. The brown powder was dried under a flow of nitrogen and dissolved in acetonitrile (2 mL).

Carbonyldiimidazole (0.09 g, 0.6 mmole) was added to a stirred solution of benzoic acid (0.07 g, 0.6 mmole) in acetonitrile (1 mL), and stirring continued for 10 min at room temperature. This solution was then added dropwise to a solution N-methylmorpholine (0.08 g, 0.8 mmole) and the hydrobromide salt described above. The mixture was stirred for 24 h at room temperature. The reaction mixture was evaporated under vacuum and the residue was dissolved in methylene chloride (20 mL). The solution was washed with water (20 mL), 10% aqueous citric acid solution (20 mL), water (20 mL), brine (20 mL), dried (2 g of MgSO$_4$) and evaporated under reduced pressure. The residue, containing 47a and 47b, was applied to a preparative TLC plate and developed two or three times with 15% isopropanol in chloroform. The lower band contained 47a while the upper band contained 47b. The two bands were separately scraped from the plate, extracted with 20% methanol in chloroform (3×25 mL) and eluent solvent evaporated under reduced pressure. The desired product (47b) isolated as 0.04 g (0.05 mmoles) (25% yield) of a white amorphous powder, mp 65°–66° C., was obtained from the upper TLC band. $^1$H-NMR (CDCl$_3$) δ 1.13(3H$_a$,app.d, J=7Hz, rotamers of l); 1.20(3H$_{a'}$,app.d, J=7Hz, rotamers of l); 1.36(3H$_b$,d, J=8Hz); 1.40–2.22(8H$_c$,m); 2.44(2H$_d$,app.t, J=8Hz); 2.64(2H$_{d'}$,app.t, J=8Hz); 3.18(2H$_e$,m); 3.33(2H$_f$,app.t, J=8Hz); 3.66(2H$_g$,s); 4.30(2H$_h$, center of 2 sets of dd, J=20Hz, rotamers of the CH$_{2(h)}$ geminal system); 4.53(1H$_i$,app.t, J=8Hz); 4.63(1H$_j$,app.t, J=8Hz); 4.80(2H$_{k,l}$,m); 5.42(1H$_m$,m); 6.70–7.10(2H$_n$,m, rotamers of amide —NH); 7.24(1H$_o$,app.d, J=10Hz, rotamers of l); 7.28(1H$_{o'}$,app.d, J=10Hz, rotamers of l); 7.34(2H$_{p,p'}$,app.dd, J$_{qp}$=8Hz, J$_{qr}$=2Hz); 7.43(1H$_q$,app.dd, J$_{qp}$=8Hz, J$_{qr}$=2Hz); 7.83(2H$_{r,r'}$,app.dd, J$_{rp}$=8Hz, J$_{rq}$=2Hz); 8.20(1H$_s$,app.d, J=10Hz, rotamers of l); 8.25(1H$_{s'}$,app.d, J=10Hz, rotamers of l)ppm. IR (CHCl$_3$) 3400, 1730, 1645, 1525, 1440, 1345, 1215, 750, 665 cm$^{-1}$. Elemental Analysis cal'd for C$_{36}$H$_{46}$N$_6$O$_{11}$: C,58.50;H,6.20;N,11.38. Found: C,58.53;H,6.37;N,11.31.

EX. 30 p-Nitrophenyl N-[Methoxysuccinyl-(N$_\delta$-benzoyl)ornithylalanylprolylmethyl]-N-isopropylcarbamate (47a, the LLL diastereomer)

times with 15% isopropanol in chloroform. The lower band contained 47a while the upper band contained 47b. The two bands were separately scraped from the plate, extracted with 20% methanol in chloroform (3×25 mL) and eluent solvent evaporated under reduced pressure. The desired product (47a) isolated as 0.06 g (0.09 mmoles) (43% yield) of a white amorphous powder, mp 55°–56° C., was obtained from the lower TLC band. $^1$H-NMR (CDCl$_3$) δ 1.06–1.28(6H$_{a,a'}$,m, rotamer of l); 1.32(3H$_b$,d, J=8Hz); 1.38–2.32(8H$_c$,m); 2.46(2H$_d$,app.t, J=8Hz); 2.64(2H$_{d'}$,app.t, J=8Hz); 3.20(2H$_e$,m); 3.53–3.88(2H$_f$,m); 3.66(3H$_g$,s); 4.20,4.32(2H$_h$, center of a set of dd, overlapping with an other set, J=20Hz, rotamers of CH$_{2(h)}$ geminal system); 4.53(1H$_i$,app.t, J=8Hz); 4.63(1H$_j$,app.t, J=8Hz); 4.80(2H$_{k,l}$,m); 5.42(1H$_m$,m); 6.70–7.10(2H$_{n,o}$m, rotamers of amide —NH); 7.24(1H$_p$,app.d, J=10Hz, rotamers of l); 7.28(1H$_{p'}$,app.d, J=10Hz, rotamers of l); 7.34(2H$_{q,q'}$,app.dd, J$_{qr}$=8Hz, J$_{qq'}$=2Hz); 7.43(1H$_r$,app.dd, J$_{rq}$=8Hz, J$_{rs}$=2Hz); 7.83(2H$_{s,s'}$,app.dd, J$_{sq}$=8Hz, J$_{sr}$=2Hz); 8.20(1H$_t$,app.d, J=10Hz, rotamers of l); 8.25(1H$_{t'}$,app.d, J=10Hz, rotamers of l)ppm. IR (CHCl$_3$) 3400, 1730, 1645, 1525, 1440, 1345, 1215, 750, 665 cm$^{-1}$. Elemental Analysis cal'd for C$_{36}$H$_{46}$N$_6$O$_{11}$: C,58.50;H,6.20;N,11.38. Found: C,58.54; H,6.36;N,11.18.

EX. 31 p-Nitrophenyl N-[Methoxysuccinylalanyl-(N$_\epsilon$-carbobenzoxy)lysylprolylmethyl]-N-isopropylcarbamate (48b, the LLD diastereomer)

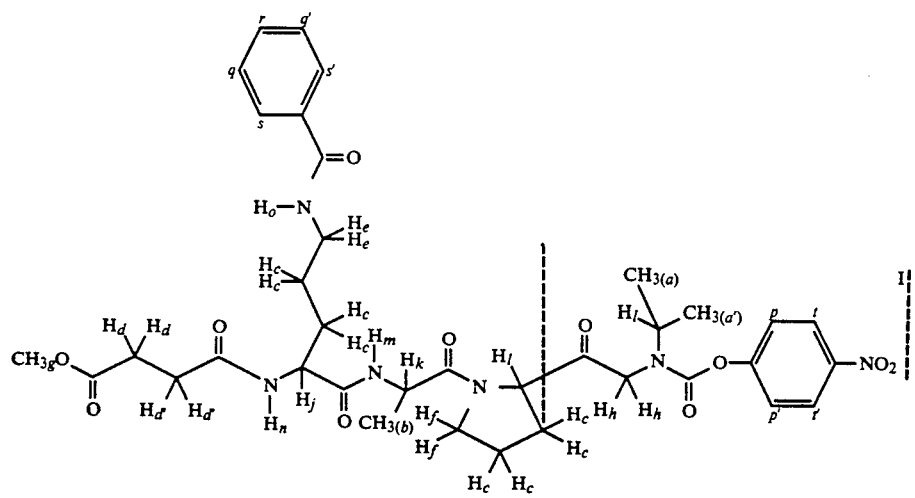

47a

The title compound was prepared from 46a and 46b following a procedure analogous to that described for 47b. The residue, containing 47a and 47b, was applied to a preparative TLC plate and developed two or three

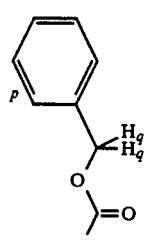

48b

-continued

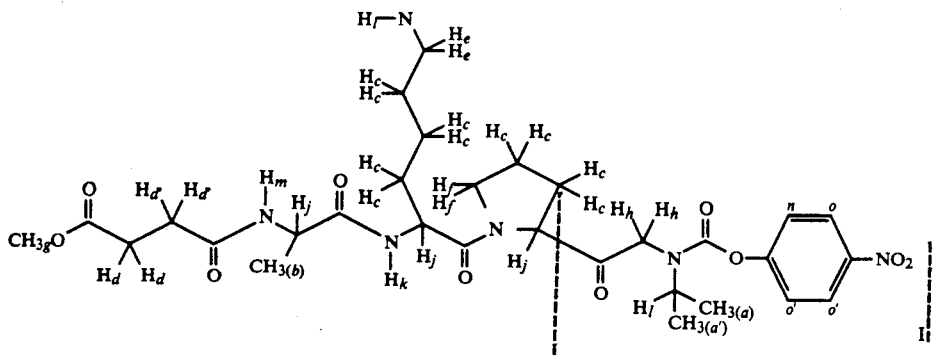

The title compound was prepared from 7 and 22 following a procedure analogous to that described for 44b. The amorphous powder contining 48a and 48b was dissolved in chloroform and applied to a preparative TLC plate (100 mg/plate) and developed two or three times with 4% methanol in ethyl acetate. The upper band contained 48a while the lower band contained 48b.

mental Analysis cal'd for $C_{38}H_{50}N_6O_{12}$: C,58.30;H,6.40; N,10.70. Found: C,58.49;H,6.47;N,10.63.

EX. 32
p-Nitrophenyl N-[Methoxysuccinyl-($N_\delta$-carbobenzoxy) lysylprolylmethyl]-N-isopropylcarbamate (48a, the LLL diastereomer)

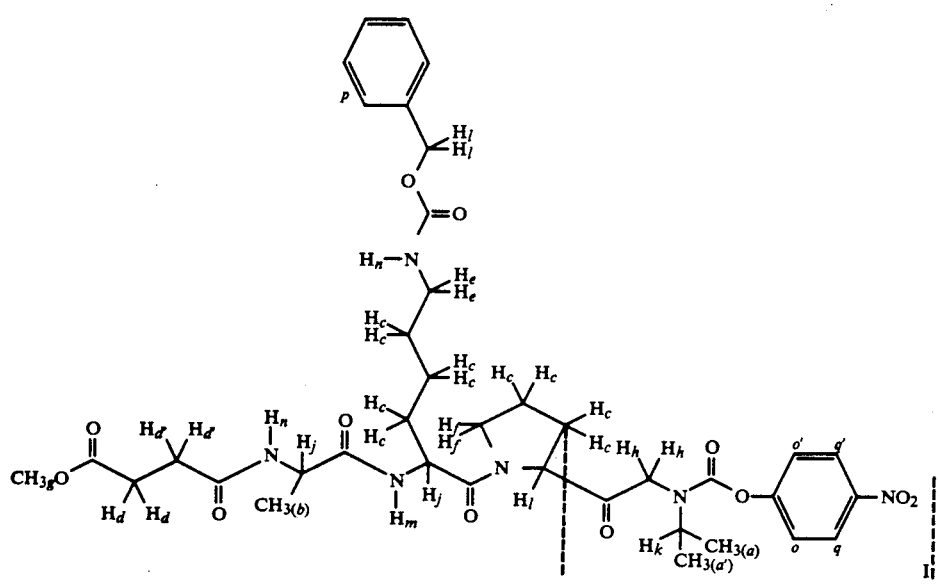

The two bands were separately scraped from the plate, extracted with 20% methanol in chloroform (3×25 mL) and eluent solvent evaporated under reduced pressure. The desired product (48b) isolated as 0.24 g (0.31 mmoles) (36% yield) of a white amorphous powder, mp 44°–45° C., was obtained from the upper TLC band. $^1$H-NMR (CDCl$_3$) δ 1.13(3H$_{a'}$,app.d, J=7Hz, rotamer of l); 1.20(3H$_{a'}$,app.d, J=7Hz, rotamer of l); 1.36(3H$_b$,d, J=8Hz); 1.40–2.22(10H$_c$,m); 2.44(2H$_d$,app.t, J=8Hz); 2.64(2H$_{d'}$,app.t, J=8Hz); 3.18(2H$_e$,m); 3.56–3.84(2H$_f$,m); 3.66(3H$_g$,s); 4,23(2H$_h$, center of 2 sets of dd, J=20Hz, rotamers of the CH$_{2(h)}$ geminal system); 4,34–4.58(4H$_{i,j}$,m); 4.60–4.64(1H$_k$,m); 5.10(2H$_q$,s); 6.34–7.16(2H$_{l,m}$,m, rotamer of amide —NH); 7.22(1H$_n$,app.d, J=10Hz, rotamers of l); 7.26(1H$_{n'}$,app.d, J=10Hz, rotamers of l); 8.22(1H$_o$,app.d, J=10Hz, rotamers of l); 8.24(1H$_{o'}$,app.d, J=10Hz, rotamers of l); 7.34(5H$_p$,app.s) ppm. IR (CHCl$_3$) 3305, 1720, 1645, 1520, 735, 700 cm$^{-1}$. Ele- The title compound was prepared from 7 and 22 following a procedure analogous to that described for 44b. The amorphous powder containing 48a and 48b was dissolved in chloroform and applied to a preparative TLC plate (100 mg/plate) and developed two or three times with 4% methanol in chloroform. The upper band contained 48a while the lower band contained 48b. The two bands were separately scraped from the plate, extracted with 20% methanol in chloroform (3×25 mL) and eluent solvent evaporated under reduced pressure. The desired product (48a) isolated as 0.36 g (0.46 mmoles) (54% yield) of a white amorphous powder, mp56°–57° C., was obtained from the upper TLC band. $^1$H-NMR (CDCl$_3$) δ 1.06–1.28(6H$_{a,a'}$,m, rotamers of l); 1.32(3H$_b$,d, J=8Hz); 1.38–2.32(10H$_c$,m); 2.46(2H$_d$,app.t, J=8Hz); 2.64(2H$_{d'}$,app.t, J=8Hz); 3.20(2H$_e$,m); 3.52–3.88(2H$_f$,m); 3.66(3H$_g$s); 4.20,4.34(2H$_h$, center of a set of dd, overlapping with another set, J=20 Hz, rotamers of the CH$_{2(h)}$ geminal system); 4.50(2H$_j$,app.t,J=8Hz); 4.50–4.80(2H$_{j,k}$,m);

5.10(2H$_j$,s); 5.42(1H$_m$,m); 6.36-7.08(2H$_n$,m, rotamers of amide —NH); 7.24(1H$_o$,app.d, J=10Hz, rotamers of l); 7.28(1H$_{o'}$,app.d, J=10Hz, rotamers of l); 7.35(5H$_p$,app.s); 8.20(1H$_q$,app. d, J=10Hz, rotamers of l); 8.25(1H$_{q'}$,app.d, J=10 Hz, rotamers rotamers of l)ppm. IR (CHCl$_3$) 3305, 1720, 1645; 1520, 735, 700 cm$^{-1}$. Elemental Analysis cal'd for C$_{38}$H$_{50}$N$_6$O$_{12}$: C,58.30; H,6.40;N,10.70. Found: C,58.12; H,6.55; N,10.64.

EX. 33 p-Nitrophenyl N-[Methoxysuccinyl)alanyl-(N$_\epsilon$-benzoyl)lysylprolyl-methyl]-N-isopropylcarbamate (49b, the LLD diastereomer)

0.29 g (0.39 mmoles) (46% yield) of a white amorphous powder, mp 54°-55° C., was obtained from the lower TLC band. $^1$H-NMR (CDCl$_3$) δ 1.13(3H$_{a'}$,app.d, J=7Hz, rotamer of l); 1.20(3H$_{a'}$,app.d, J=7Hz, rotamer of l); 1.36(3H$_b$,d, J=8Hz); 1.40-2.22(10H$_c$,m); 2.44(2H$_d$,app.t, J=8Hz); 2.64(2H$_{d'}$,app.t, J=8Hz); 3.18(2H$_e$,m); 3.56-3.84(2H$_f$,m); 3.66(3H$_g$,s); 4,23(2H$_h$, center of 2 sets of dd, J=20Hz, rotamers of the CH$_{2(h)}$ geminal system); 4,34-4.58(4H$_{i,j}$,m); 4.60-4.64(1H$_k$,m); 6.34-7.16(2H$_{l,m}$,m, rotamer of amide —NH); 7.22(1H$_n$,app.d, J=10Hz, rotamers of l); 7.26(1H$_{n'}$,app.d, J=10Hz, rotamers of l); 7.34(2H$_{o,o'}$,app.dd, J$_{oq}$=8Hz, J$_{oo'}$=2Hz); 7.43(1H$_p$,app.d, J$_{po}$=8Hz); 7.83(2H$_{q,q'}$,app.dd, J$_{qo}$=8Hz, J$_{qp}$=2Hz); 8.22(1H$_r$,app.d, J=10Hz, rotamers of l); 8.24(1H$_{r'}$,app.d, J=10Hz, rotamers of l) ppm. IR (CHCl$_3$) 3340, 1735, 1645, 1520, 1435, 1345, 1260, 735, 700 cm$^{-1}$. Elemental Analysis cal'd for C$_{37}$H$_{48}$N$_6$O$_{11}$: C,58.92;H,6.37; N,11.14. Found: C,58.56; H,6.47; N,11.30.

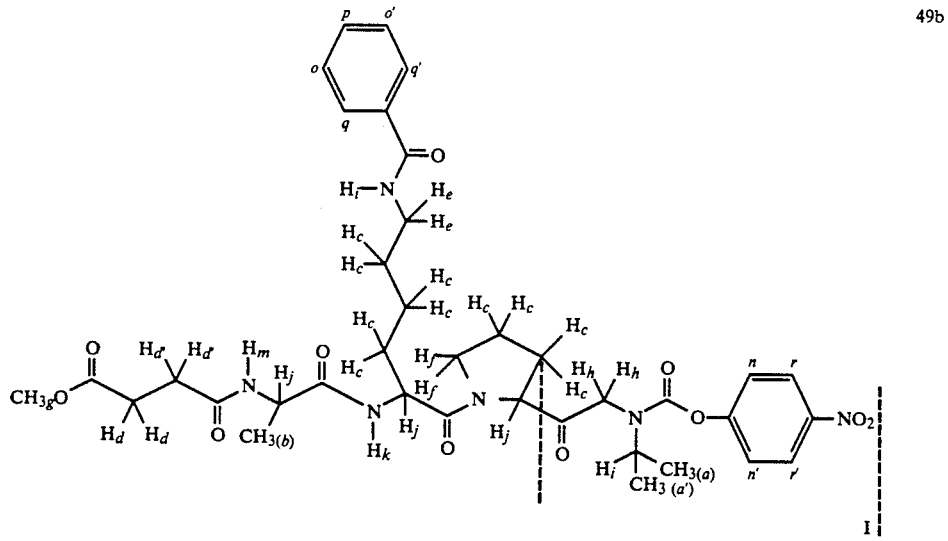

49b

The title compound was prepared from 5 and 22 following a procedure analogous to that described for 44b. The amorphous powder containing 49a and 49b was dissolved in chloroform and applied to a preparative TLC plate (100 mg/plate) and developed two or three times with 15% isopropanol in chloroform. The upper band contained 49a while the lower band contained 49b. The two bands were separately scraped from the plate, extracted with 20% methanol in chloroform (3×25 mL) and eluent solvent evaporated under reduced pressure. The desired product (49b) isolated as

EX. 34 p-Nitrophenyl N-[Methoxysuccinyl)alanyl-(N$_\epsilon$-benzoyl)lysylprolymethyl]-N-isopropylcarbamate (49a, the LLL diastereomer)

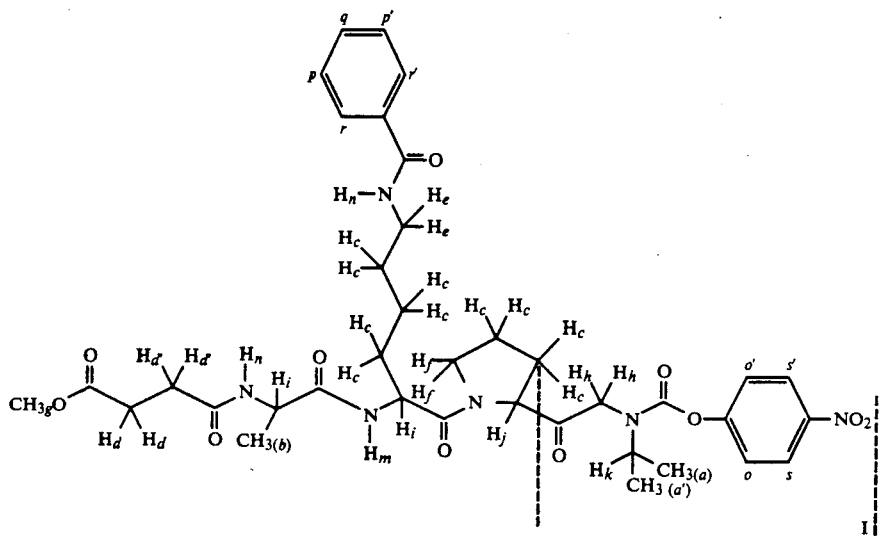

The title compound was prepared from 5 and 22 following a procedure analogous to that described for 44b. The amorphous powder containing 49a and 49b was dissolved in chloroform and applied to a preparative TLC plate (100 mg/plate) and developed two or three times with 15% isopropanol in chloroform. The upper band contained 49a while the lower band contained 49b. The two bands were separately scraped from the plate, extracted with 20% methanol in chloroform (3×25 mL) and eluent solvent evaporated under reduced pressure. The desired product (49a) isolated as 0.29 g (0.38 mmoles) (45% yield) of a white amorphous powder, mp 61°-62° C., was obtained from the upper TLC band. $^1$H-NMR (CDCl$_3$) δ 1.06–1.28(6H$_{a,a'}$,m, rotamers of l); 1.32(3H$_b$,d, J=8Hz); 1.38–2.32(10H$_c$,m); 2.46(2H$_d$,app.t, J=8Hz); 2.64(2H$_{d'}$,app.t, J=8Hz); 3.20(2H$_e$,m); 3.52–3.88(2H$_f$,m); 3.66(3H$_g$,s); 4.20,4.32(2H$_h$, center of a set of dd, overlapping with another set, J=20Hz, rotamer of the CH$_{2(h)}$ geminal system); 4.50(2H$_{i,j}$,app.t, J=8Hz); 4.50–4.80(2H$_{k,l}$,m); 5.42(1H$_m$,m); 6.36–7.08(2H$_n$,m, rotamers of amide —NH); 7.24(1H$_o$,app.d, J=10Hz, rotamers of l); 7.28(1H$_{o'}$,app.d, J=10Hz, rotamers of l); 7.34(2H$_{p,p'}$,app.dd, J$_{pr}$=8Hz,J$_{pp'}$=2Hz); 7.43(1H$_q$,app.d, J$_{qp}$=8Hz, J$_{qr}$=2Hz); 7.83(2H$_{r,r'}$,app.dd, J$_{rp}$=8Hz, J$_{rq}$=2Hz); 8.20(1H$_s$,app.d, J=10Hz, rotamers of l); 8.25(1H$_{s'}$,app.d, J=10Hz, rotamers of l)ppm. IR (CHCl$_3$) 3340, 1730, 1645, 1520, 1435, 1345, 1260, 735, 700 cm$^{-1}$. Elemental Analysis cal'd for C$_{37}$H$_{48}$N$_6$O$_{11}$: C,58.92; H,6.37; N,11.14. Found: C,58.80; H,6.46; N,11.28.

EX. 35 p-Nitrophenyl N-[Methoxysuccinylalanyl-(N$_\delta$-carbobenzoxy)ornithylprolymethyl]-N-isopropylcarbamate (50b, the LLD diastereomer)

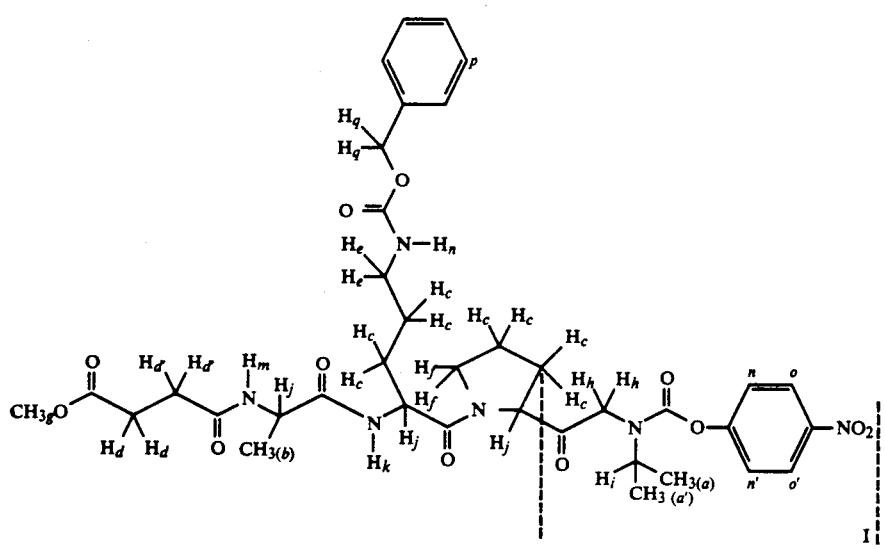

The title compound was prepared from 9 and 22 following a procedure analogous to that described for 44b. The amorphous powder containing 50a and 50b was dissolved in chloroform and applied to a preparative TLC plate (100 mg/plate) and developed two or three times with 4% methanol in ethyl acetate. The upper band contained 50a while the lower band contained 50b. The two bands were separately scraped from the plate, extrcted with 20% methanol in chloroform (3×25 mL) and eluent solvent evaporated under reduced pressure. The desired product (50b) isolated as 0.1 g (0.13 mmoles) (15% yield) of a white amorphous powder, mp 65°-66° C., was obtained from the lower TLC band. $^1$H-NMR (CDCl$_3$) δ 1.13(3H$_{a'}$,app.d, J=7Hz, rotamer of l); 1.20(3H$_{a'}$,app.d, J=7Hz, rotamer of l); 1.36(3H$_b$,d, J=8Hz); 1.40-2.22(8H$_c$,m); 2.44(2H$_d$,app.t, J=8Hz); 2.64(2H$_{d'}$,app.t, J=8Hz); 3.18(2H$_e$,m); 3.56-3.84(2H$_f$,m); 3.66(3H$_g$,s); 4,23(2H$_h$, center of 2 sets of dd, J=20Hz, rotamers of the CH$_{2(h)}$ geminal system); 4,34-4.58(4H$_{i,j}$,m); 4.60-4.64(1H$_k$,m); 5.10(2H$_q$s); 6.34-7.16(2H$_{l,m}$,m, rotamer of amide —NH); 7.22(1H$_n$,app.d, J=10Hz, rotamers of l); 7.26(1H$_{n'}$,app.d, J=10Hz, rotamers of l); 8.22(1H$_o$,app.d, J=10Hz, rotamers of l); 8.24(1H$_{o'}$,app.d, J=10Hz, rotamers of l); 7.34(5H$_p$,app.s) ppm. IR (CHCl$_3$) 3305, 1720, 1645, 1520, 735, 700 cm$^{-1}$. Elemental Analysis cal'd for C$_{37}$H$_{48}$N$_6$O$_{12}$: C,57.80; H,6.25; N,10.94. Found: C,58.12; H,6.55; N,10.64.

EX. 36 p-Nitrophenyl N-[Methoxysuccinylalanyl-N$_\delta$-carbobenzoxy)ornithylprolylmethyl]-N-isopropylcarbamate (50a, the LLL diastereomer)

The title compound was prepared from 9 and 22 following a procedure analogous to that described for 44b. The amorphous powder containing 50a and 50b was dissolved in chloroform and applied to a preparative TLC plate (100 mg/plate) and developed two or three times with 4% methanol in ethyl acetate. The upper band contained 50a while the lower band contained 50b. The two bands were separately scraped from the plate, extracted with 20% methanol in chloroform (3×25 mL) and eluent solvent evaporated under reduced pressure. The desired product (50a) isolated as 0.11 g (0.14 mmoles) (16% yield) of a white amorphous powder, mp 55°-56 ° C., was obtained from the upper TLC band. $^1$H-NMR (CDCl$_3$) δ 1.06-1.28(6H$_{a,a'}$,m, rotamers of l); 1.32(3H$_b$,d, J=8Hz); 1.38-2.32(8H$_c$,m); 2.46(2H$_d$,app.t, J=8Hz); 2.64(2H$_{d'}$,app.t, J=8Hz); 3.20(2H$_e$,m); 3.52-3.88(2H$_f$,m); 3.66(3H$_g$,s); 4.20,4.32(2H$_h$, center of a set of dd, overlapping with another set, J=20Hz, rotamers of the CH$_{2(h)}$ geminal system); 4.50(2H$_i$,app.t, J=8Hz); 4.50-4.80(2H$_{j,k}$,m); 5.10(2H$_l$,s); 5.42(1H$_m$,m); 6.36-7.08(2H$_n$,m, rotamers of amide —NH); 7.24(1H$_o$,app.d, J=10Hz, rotamers of l); 7.28(1H$_{o'}$,app.d, J=10Hz, rotamers of l); 7.35(5H$_p$,app.s) 8.20(1H$_q$,app. d, J=10Hz, rotamers of l); 8.25(1H$_{q'}$,app.d, J=10Hz, rotamers of l)ppm. IR (CHCl$_3$) 3305, 1720, 1645, 1520, 735, 700. Elemental Analysis cal'd for C$_{37}$H$_{48}$N$_8$O$_{12}$: C,57.80; H,6.25; N,10.94. Found: C,57.68; H,6.39; N,10.89.

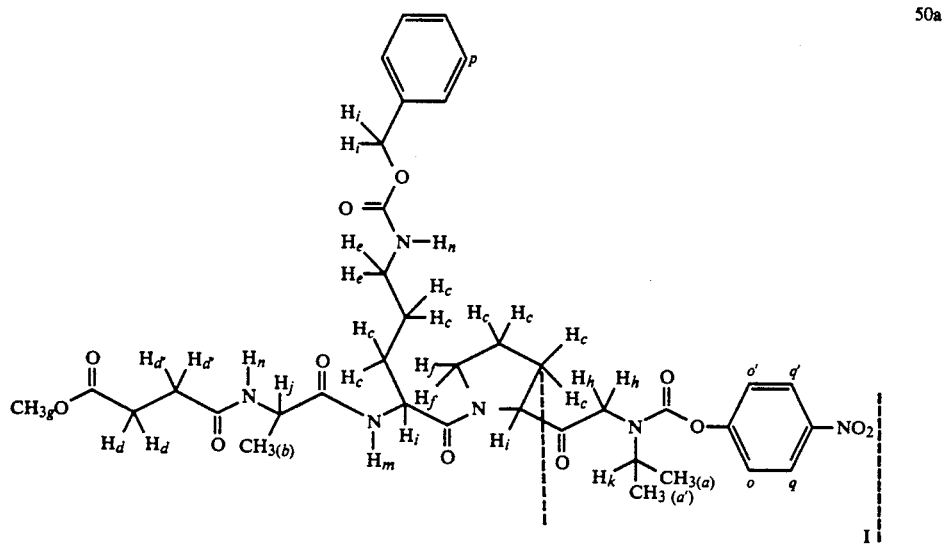

EX. 37 p-Nitrophenyl N-[Methoxysuccinylalanyl-(N$_\delta$-benzoyl)ornithylprolyl-methyl]-N-isopropylcarbamate (51b, the LLD diastereomer)

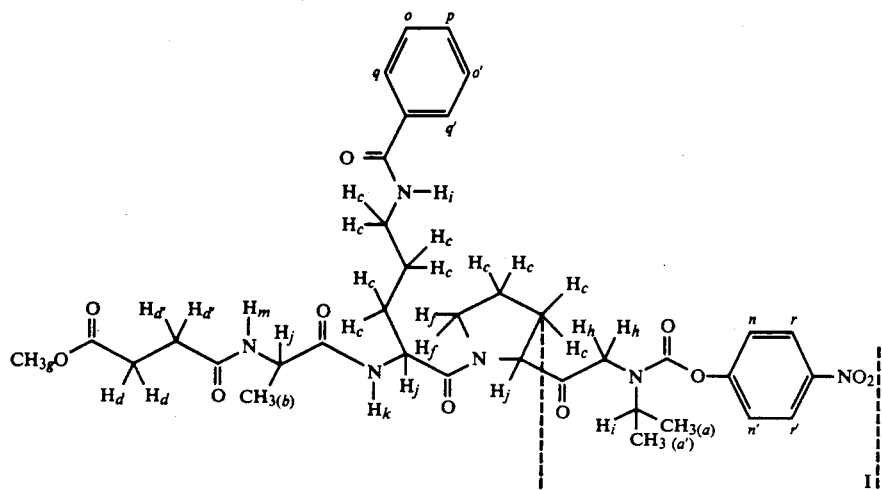

The title compound was prepared from 50a and 50b following a procedure analogous to that described for 47b. The residue, containing 51a and 51b, was applied to a preparative TLC plate and developed two or three times with 4% methanol in ethyl acetate. The upper band contained 51a while the lower band contained 51b. The two bands were separately scraped from the plate, extracted with 20% methanol in chloroform (3×25 mL) and eluent solvent evaporated under reduced pressure. The desired product (51b) isolated as 0.04 g (0.05 mmoles) (26% yield) of a white amorphous powder, mp 54°-55° C., was obtained from the lower TLC band. $^1$H-NMR (CDCl$_3$) δ 1.13(3H$_{a'}$,app.d, J=7Hz, rotamer of 1); 1.20(3H$_{a'}$,app.d, J=7Hz, rotamer of 1); 1.36(3H$_b$,d, J=8Hz); 1.40–2.22(8H$_c$,m); 2.44(2H$_d$,app.t, J=8Hz); 2.64(2H$_{d'}$,app.t, J=8Hz); 3.18(2H$_e$,m); 3.56–3.84(2H$_f$,m); 3.66(3H$_g$,s); 4,23(2H$_h$, center of 2 sets of dd, J=20Hz, rotamers of the CH$_{2(h)}$ geminal system); 4,34–4.58(4H$_{i,j}$,m); 4.60–4.64(1H$_k$,m); 6.34–7.16(2H$_{l,m}$,m, rotamer of amide —NH); 7.22(1H$_n$,app.d, J=10Hz, rotamers of 1); 7.26(1H$_{n'}$,app.d, J=10Hz, rotamers of 1); 7.34(2H$_{o,o'}$,app.dd, J$_{oq}$=8Hz, J$_{oo'}$=2Hz); 7.43(1H$_p$,app.d, J$_{po}$=8Hz); 7.83(2H$_{q,q'}$,app.dd, J$_{qo}$=8Hz, J$_{qp}$=2Hz); 8.22(1H$_r$,app.d, J=10Hz, rotamers of 1); 8.24(1H$_{r'}$,app.d, J=10Hz, rotamers of 1)ppm. IR (CHCl$_3$) 3340, 1730, 1645, 1520, 1435, 1345, 1260, 735, 700 cm$^{-1}$. Elemental Analysis cal'd for C$_{36}$H$_{46}$N$_6$O$_{11}$: C,58.50; H,6.20; N,11.38. Found: C,58.43; H,6.29; N,11.24.

EX. 38 p-Nitrophenyl N-[Methoxysuccinylalanyl-N$_\delta$-benzoyl)ornithylprolyl-methyl]-N-isopropylcarbamate (51a, the LLL diastereomer)

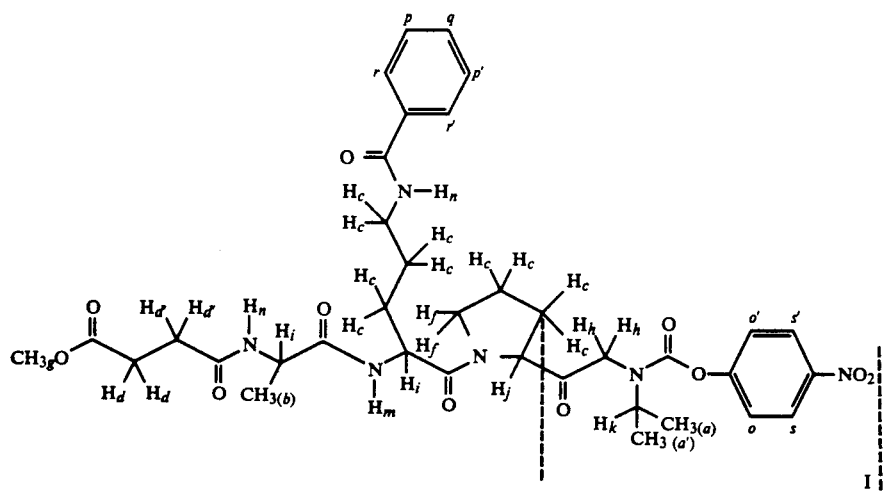

The title compound was prepared from 50a and 50b following a procedure analogous to that described for 47b. The residue, containing 51a and 51b, was applied to a preparative TLC plate and developed two or three times with 4% methanol in ethyl acetate. The upper band contained 51a while the lower band contained 51b. The two bands were separately scraped from the plate, extracted with 20% methanol in chloroform (3×25 mL) and eluent solvent evaporated under reduced pressure. The desired product (51a) isolated as 0.05 g (0.06 mmoles) (32% yield) of a white amorphous powder, mp 55°–56° C., was obtained from the upper TLC band. $^1$H-NMR (CDCl$_3$) δ 1.06–1.28(6H$_{a,a'}$,m, rotamers of l); 1.32(3H$_b$,d, J=8Hz); 1.38–2.32(8H$_c$,m); 2.46(2H$_d$,app.t, J=8Hz); 2.64(2H$_{d'}$,app.t, J=8Hz); 3.20(2H$_e$,m); 3.52–3.88(2H$_f$,m); 3.66(3H$_g$,s); 4.20,4.32(2H$_h$, center of a set of dd, overlapping with another set, J=20Hz, rotamers of the CH$_{2(h)}$ geminal system); 4.50(2H$_{i,j}$,app.t, J=8Hz); 4.50–4.80(2H$_{k,l}$,m); 5.42(1H$_m$,m); 6.36–7.08(2H$_n$,m, rotamers of amide —NH); 7.24(1H$_o$,app.d, J=10Hz, rotamers of l); 7.28(1H$_{o'}$,app.d, J=10Hz, rotamers of l); 7.34(2H$_{p,p'}$,app.dd, J$_{pr}$=8Hz, J$_{pp'}$=2Hz); 7.43(1H$_q$,app.d, J$_{qp}$=8Hz, J$_{qr}$=2Hz); 7.83(2H$_{r,r'}$,app.dd, J$_{rp}$=8Hz, J$_{rq}$=2Hz); 8.20(1H$_s$,app.d, J=10Hz, rotamers of l); 8.25(1H$_{s'}$,app.d, J=10Hz, rotamers of l)ppm. IR (CHCl$_3$) 3340, 1730, 1645, 1520, 1435, 1345, 1260, 735, 700 cm$^{-1}$. Elemental Analysis cal'd for C$_{36}$H$_{46}$H$_6$O$_{11}$: C,58.50; H,6.20; N,11.38. Found: C,58.38; H,6.36; N,11.38.

2. Stereospecific synthesis of desmosine-like peptidyl carbamate 48a and 48b

EX. 39

N$_α$-Methoxysuccinylalanyl-N$_ε$-carbobenzoxylysylproline phenacyl ester (23, the LLD diastereomer)

(1×50 cm). Impurities were eliminated by first passing methylene chloride and subsequently the compound was eluted with 4% methanol in methylene chloride. Upon evaporation of the eluant solvent under reduced pressure an oil was obtained. The latter was crystallized form ethyl acetate/hexane to give a white crystalline powder. Incorporation of 41 into the product gave 0.5 g (0.77 mmole) (96% yield) of crystalline powder, mp 114°–116° C.

Procedure 2

Isobutylchloroformate (0.43 g, 3.2 mmoles) in acetonitrile (4 mL) was added to a dry-ice/carbon tetrachloride cooled solution of 7 (1.3 g, 2.9 mmoles) and N-methylmorpholine (0.3 g, 2.9 mmoles) in THF (10 mL). After 10 min, D-proline phenacyl ester hydrochloride (41) (0.9 g, 1.5 mmoles) as a solid and N-methylmorpholine (0.35 g, 3.5 mmoles) in acetonitrile (6 mL) were added to the reaction mixture maintained at −15° C. The reaction mixture was allowed to warm to 5° C. in 30 min, was filtered after 90 min, and the filtrate was evaporated in vacuo. The residue was redissolved in methylene chloride (20 mL) and washed with water (20 mL), 10% aqueous citric acid (20 mL), water (20 mL) and brine (20 mL); dried (2 g of MgSO$_4$) and evaporated in vacuo. The residue, containing the product,

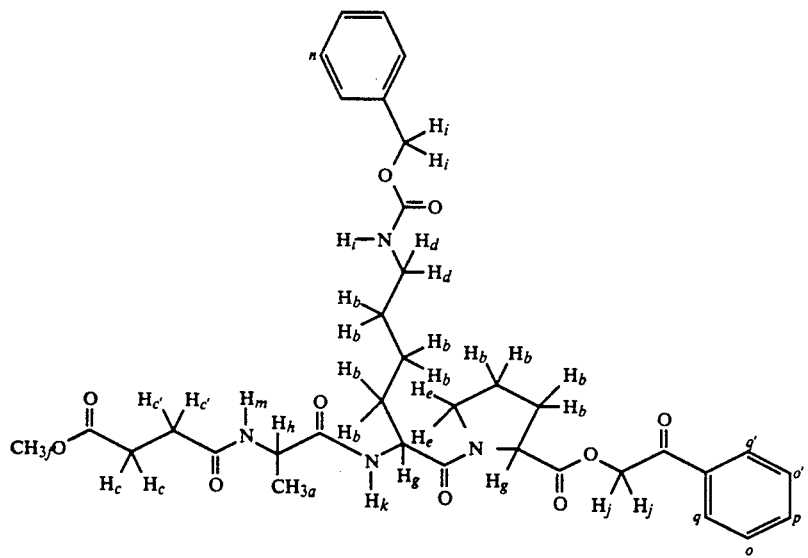

23

Procedure 1

A concentrated solution of N,N'-dicyclohexylcarbodiimide (0.17 g, 0.8 mmole) in THF was added dropwise to an ice cooled solution containing 7 (0.4 g, 0.8 mmole) and N-hydroxysuccinimide (0.1 g, 0.8 mmole) in THF (4 mL). The solution was stirred at 5° C. for 14 h and the precipitated urea formed was filtered under vacuum. The filtrate was immediately used in the next reaction without further work-up.

A mixture of the above cooled (0° C.) solution and D-proline phenacyl ester hydrochloride (41) (0.22 g, 0.8 mmole) was stirred and triethylamine (0.08 g, 0.8 mmole) in THF (0.5 mL) was added dropwise. Upon completion of the reaction (5 h), the precipitate was filtered, washed with ethyl acetate and the filtrate evaporated under vacuum. The residue, containing the product, was chromatographed on 20 g of silica gel column was purified similar to the methodology in procedure 1. The transparent oil was crystallized from ethyl acetate/hexane. The incorporation of 41 gave 0.85 g (1.25 mmoles) (43% yield) of white crystalline powder (23), mp 114°–116° C. $^1$H-NMR (CDCl$_3$) δ 1.36(3H$_a$,d,J=8Hz); 1.40–2.22(10H$_b$,m); 2.44(2H$_c$,app. t,J=8Hz); 2.64(2H$_{c'}$,app. t,J=8Hz); 3.18(2H$_d$,m); 3.56(2H$_e$,m); 3.66(3H$_f$,s); 4.50(2H$_g$,app. t,J=8Hz); 4.53–4.80(1H$_h$,m); 5.10(2H$_i$,s); 5.43(2H$_j$,s); 5.76(1H$_k$,m, rotamer of amide—NH); 6.70–7.30(2H$_{l,m}$,m, rotamer of amide—NH); 7.36(5H$_n$,s); 7.60(3H$_{o,o',p}$, app. dd, J$_{oq}$=8Hz,J$_{oo'}$=2Hz); 8.06(2H$_{qq'}$,app. dd, J$_{qo}$=8Hz,J$_{qp}$=2Hz)ppm. IR (CHCl$_3$) 3280, 1725, 1680, 1630, 725, 635 cm$^{-1}$.

EX. 40

N$_\alpha$-Methoxysuccinylalanyl-N$_\epsilon$-carbobenzoxylysylproline phenacyl ester (24, the LLL diastereomer)

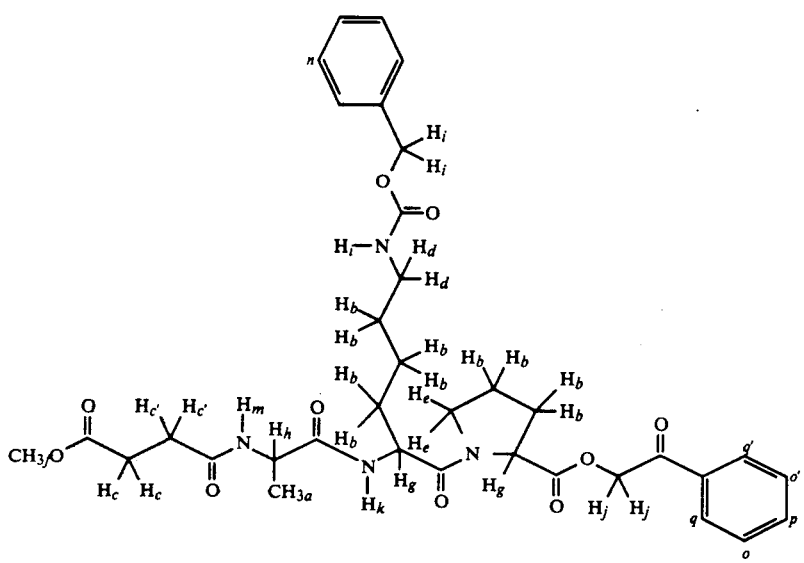

24

The title compound was prepared by an analogous procedure to that described in the preparation of compound 23. L-Proline phenacyl ester hydrochloride 42 was substituted in place of the D-enantiomer to form the LLL diastereomer product 24. Following procedure 1, the incorporation of 42 into 24 gave rise to 0.4 g (0.54 mmole) (74% yield) of crystalline powder mp 116°–118° C. The LLL diastereomer 24 demonstrated a lower Rf value than the LLD diastereomer 23 on silica gel TLC plates eluted with 4% ethyl acetate in methylene chloride and 5% methanol in methylene chloride. Procedure 2, produced 1.3 g (1.94 mmoles) (66.8% yield) of white crystalline powder (24), mp 116°–118° C., with similar Rf values. $^1$H-NMR (CDCl$_3$) $\delta$ 1.36(3H$_a$,d,J=8Hz); 1.40–2.22(10H$_b$,m); 2.44(2H$_c$,app. t,J=8Hz); 2.64(2H$_c$[6H$_{c'}$, app.t,J=8Hz); 3.18(2H$_d$,m); 3.66(3H$_f$,s); 4.34–4.58(3H$_{g,h}$,m); 4.60–4.64(1H$_k$,m); 5.10(2H$_i$,s); 5.43(2H$_j$,s); 6.70–7.30(2H$_{l,m}$,m, rotamer of amide —NH); 7.36(5H$_n$,s); 7.60(3H$_{o,o',p}$,app. dd, J$_{oq}$=8Hz,J$_{oo,}$=2Hz); J$_{qo}$=8Hz,J$_{qp}$=2Hz).

8.06(2H$_{qq'}$,app.dd,

EX. 41

N$_\alpha$-Methoxysuccinylalanyl-N$_\epsilon$-carbobenzoxylysylproline (25, the LLD diastereomer)

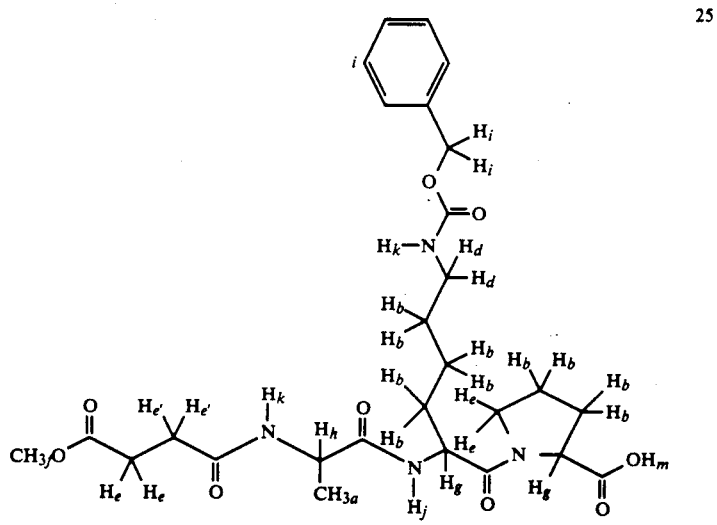

25

Small portions of zinc metal (total 2 g) were added over a 1 h period to the phenacyl ester (23) (0.5 g, 0.8 mmole) dissolved in glacial acetic acid (10 mL). After 3 h, the suspension was diluted with 20% methanol in chloroform (50 mL), filtered under vacuum and evaporated to a crude solid. Work-up was performed in a similar manner to that described in the preparation of 7. The chromatographically pure oil required two crystallizations from chloroform/petroleum ether to yield a white solid. Hydrolysis of the phenacyl ester of 23 produced 0.26 g (0.46 mmole) (57% yield) of a white powder (25) mp 119°–120° C. $^1$H-NMR (CDCl$_3$) $\delta$ 1.36(3H$_a$,d,J=8Hz); 1.40–2.22(10H$_b$,m); 2.44(2H$_c$,app. t,J=8Hz); 2.64(2H$_{c'}$,app. t,J=8Hz); 3.18(2H$_d$,m); 3.56(2H$_e$,m); 3.66(3H$_f$,s); 4.50(2H$_g$,app. t,J=8Hz); 4.83(1H$_h$,m); 5.10(2H$_i$,s); 5.60(1H$_j$,m, rotamer of amide —NH); 6.70–7.26(2H$_k$,m, rotamer of amide —NH);

7.36(5H$_l$,s); 10.20(1H$_m$,s)ppm. IR (CHCl$_3$) 3400, 1740, 1680, 1630 cm$^{-1}$.

EX. 42

N$_\alpha$-Methoxysuccinylalanyl-N$_\epsilon$-carbobenzoxylysylproline (26, the LLL diastereomer)

(see 25 for structure)

The title compound was prepared by an analogous procedure to that described in the preparation of compound 25. Hydrolysis of the phenacyl ester of 24 produced 0.44 g (0.78 mmole) (98% yield) of a white powder (26), mp 119°-120° C. The LLL diastereomer 26 demonstrated a lower Rf value than the LLD diastereomer 25 on silica gel TLC plates eluted with 4% methanol in ethyl acetate. $^1$H-NMR (CDCl$_3$) δ 1.36(3H$_a$,d,J=8Hz); 1.40–2.22(10H$_b$,m); 2.44(2H$_c$,app. t,J=8Hz); 2.64(2H$_{c'}$,app. t,J=8Hz); 3.18(2H$_d$,m); 3.56(2H$_e$,m); 3.66(3H$_f$,s); 4.34–4.58(3H$_{g,h}$,m); 4.60–4.64(1H$_j$,m, rotamer of amide —NH); 5.10(2H$_i$,s); 6.70–7.26(2H$_k$,m, rotamer of amide —NH); 7.36(5H$_l$,s); 10.20(1H$_m$,s).

EX. 43

N$_\alpha$-Methoxysuccinylalanyl-N$_\epsilon$-carbobenzoxylysylprolyl chloromethyl ketone (27, the LLD diastereomer)

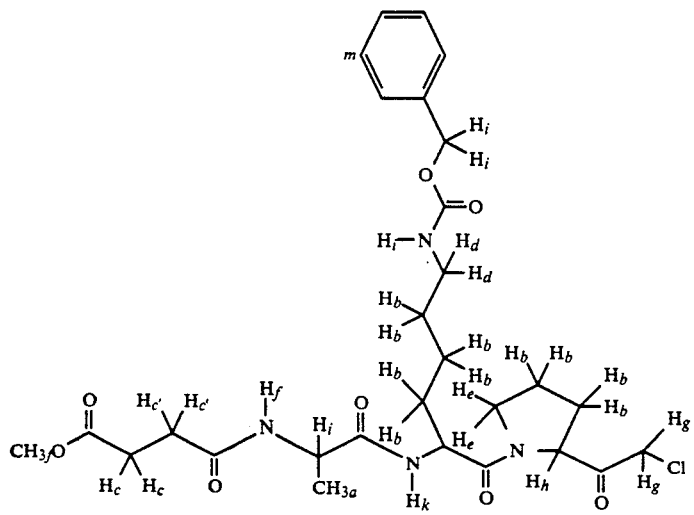

27

Isobutylchloroformate (0.11 g, 0.8 mmole) in THF (2 mL) was added to a cooled solution of 25 (0.45 g, 0.8 mmole) and N-methylmorpholine (0.08 g, 0.8 mmole) in THF (4.5 mL) and the mixture was stirred for 10 min at −15° C. A cold solution (0° C.) of diazomethane (cal'd. 0.13 gm, 3.2 mmoles) in diethyl ether was added and the mixture stirred at −10° C. for 30 min, then at 5° C. for 90 min. The reaction mixture was then diluted with ethyl acetate (40 mL), and washed with saturated aqueous sodium bicarbonate (2×30 mL), water (30 mL) and brine (30 mL); dried (5 g of MgSO$_4$) and evaporated in vacuo to give a yellow oil. $^1$H-NMR for the α-azomethyl ketone intermediate (CDCl$_3$) δ 0.86–2.23(13H,m), 2.56(4H,t,J=7Hz)m 3.03–3.40(2H,m), 3.46–4.00(5H,m), 4.40–4.83(3H,m), 5.13(2H,s), 5.40–5.80(2H,m), 6.53–7.20(2H,m), 7.40(5H,s). IR (CHCl$_3$) 3280,2215,1735,1635,1535 cm$^{-1}$.

Hydrogen chloride gas was bubbled through an ice-cooled solution of the α-azomethylketone intermediate (0.8 mmole) in ethyl acetate (10 mL) for 30s. Subsequent stirring for 10 min at 5° C., bubbling of nitrogen gas through the reaction mixture to remove excess hydrogen chloride, diluting with cold ethyl acetate, and evaporating in vacuo, gave rise to a yellow oil. The disappearance of the UV-bright TLC spot corresponding to the α-azomethylketone and appearance of the low UV absorbing TLC spot (with a lower RF value) corresponding to the α-chloromethylketone was followed using silica gel TLC plates eluted with 4% ethyl acetate in methylene chloride. The residue, containing the product, was chromatographed on 5 g of silica gel column (1×25 cm). Impurities were eliminated by first passing 25 mL of methylene chloride and subsequently the compound was eluted with 3% methanol in methylene chloride. Upon evaporation of the eluent solvent under reduced pressure a transparent oil was obtained. The latter was then crystallized from chloroform/petroleum ether to give 0.25 g (0.4 mmole) (54% yield) of crystalline powder, mp 46°–48° C. $^1$H-NMR (CDCl$_3$) δ 1.36(3H$_a$,d,J=8Hz); 1.40–2.22(10H$_b$,m); 2.44(2H$_c$,app. t,J=8Hz); 2.64(2H$_{c'}$,app. t,J=8Hz); 3.20(2H$_d$,m); 3.56(2H$_e$,m); 3.66(3H$_f$,s); 4.20,4.32(2H$_g$, center of a set of dd, overlapping with another set, J=20Hz, rotamers of the CH$_{2(g)}$geminal system); 4.50(2H$_h$,app. t,J=8Hz); 4.83(1H$_i$,m); 5.10(2H$_j$,s); 5.60(1H$_k$,m, rotamer of amide —NH); 6.70–7.26(2H$_l$,m, rotamers of amide —NH); 7.36(5H$_m$,s)ppm. IR (CHCl$_3$) 3300, 1725, 1625, 1635, 1535 cm$^{-1}$.

EX. 44

N$_\alpha$-Methoxysuccinylalanyl-N$_\epsilon$-carbobenzoxylysylprolyl chloromethyl ketone (28, the LLL diastereomer)

(see 27 for structure)

The title compound was prepared by an analogous procedure to that described in the preparation of compound 27. The presence of impurities in in the IR and NMR for the α-azomethylketone intermediate produced during the reaction did not demonstrate clear differences between the LLD and LLL diastereomers. The Rf value of the LLD and LLL diastereomers were significantly different when eluted twice on silica gel plates with 4% ethyl acetate in methylene chloride or methylene chloride. The α-chloromethylketone 28 was crystallized from chloroform/petroleum ether to give 0.25 g (0.4 mmole) (54% yield) of crystalline powder,

EX. 48 p-Nitrophenyl
N-[Methoxysuccinylalanyl-(N$_{6\delta}$-carbobenzoxy)lysyl-
prolylmethyl]-N-isopropylcarbamate (48a, the LLL
diastereomer)

(see page 46 for structure)

The title compound was prepared by an analogous procedure to that described in the preparation of compound 48b. The reaction pathway which incorporated L-proline into the final peptidyl carbamate 48a gave rise to 153.9 mg (196.0 moles) (39% yield) of amorphous solid (48a), mp 56°–57° C. $^1$H-NMR (CDCl$_3$) (see 48a above). Elemental analysis cal'd. for C$_{38}$H$_{50}$N$_6$O$_{12}$: C,58.30; H,6.44;N ,10.73. Found: C,58.12;H,6.55;N,10.64%.

3. Synthesis of protected amino acids

EX. 49

N$_\alpha$-t-Boc-N$_\epsilon$-carbobenzoxylysine (31)

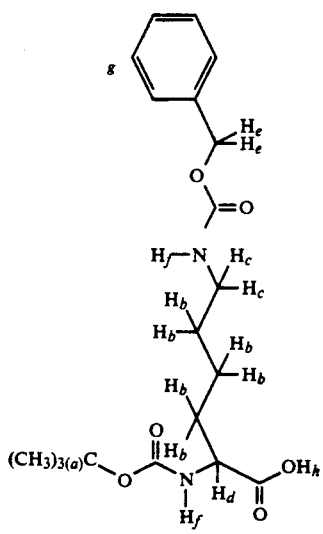

This compound was synthesized by a modified procedure of Itoh et al.[91]. t-BOC-ON (2.2 g, 8.9 mmoles) was added as a solid to a solution of triethylamine (0.9 g, 8.9 mmoles) and N$_\epsilon$-carbobenzoxy-L-lysine (2.5 g, 8.9 mmoles) in DMF (20 mL) at room temperature and the components allowed to react for 24 h. The resulting precipitate was filtered and the filtrate evaporated under vacuum. The crude oil was dissolved in methylene chloride and chromatographed on 50 g of silica gel column (3×50 cm). Impurities were eliminated by first passing 100 mL of methylene chloride and subsequently the compound was eluted with 10% methanol in methylene chloride. Upon evaporation of the eluent solvent under reduced pressure 3.25 g (8.6 mmoles) (96% yield) of an oil was obtained. $^1$H-NMR (CDCl$_3$) δ 1.46(9H$_a$,s); 1.50–2.20(6H$_b$,m); 3.23(2H$_c$, m); 4.00–4.30(1H$_d$,m); 5.10(2H$_e$,s); 6.56–7.10(2H$_f$,m, rotamers of carbamate-NH); 7.36(5H$_g$,s); 9.80(1H$_h$,s)ppm.

EX. 50

N$_\alpha$-t-Boc-N$_\epsilon$-carbobenzoxy-L-lysine phenacyl ester (32)

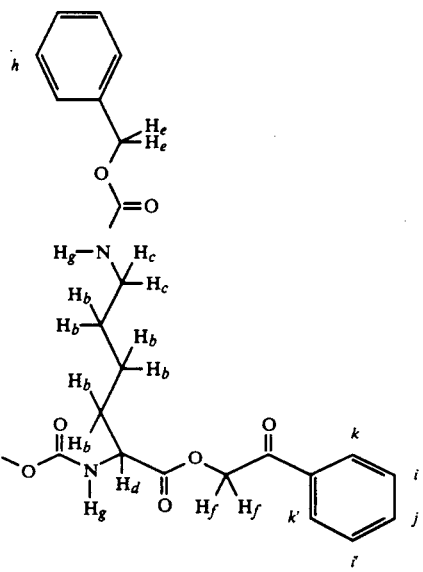

This compound was synthesized by a modified procedure of Hendrickson et al.[85]

2-Bromoacetophenone (1.8 g, 8.9 mmoles) was added as a solid to a solution of triethylamine (0.9 g, 8.9 mmoles) and 31 (3.4 g, 8.9 mmoles) in DMF (25 mL). The progress of the reaction was monitored by TLC (10% methanol in chloroform). Upon completion of the reaction (1.5 h), the reaction was stopped by the addition of water (30 mL) and decanted. The residue, containing the product, was dissolved in chloroform (40 mL) and washed with water (30 mL) and brine (30 mL); dried (10 g of MgSO$_4$) and evaporated under reduced pressure. The resulting oil was chromatographed on 30 g of silica gel column (2×50 cm). Impurities were eliminated by first passing 50 mL of methylene chloride and subsequently the compound was eluted with 3% methanol in methylene chloride. Upon evaporation of the eluent solvent under reduced pressure 3.6 g (7.2 mmoles) (81% yield) of a transparent oil was obtained. $^1$H-NMR (CDCl$_3$) δ 1.46(9H$_a$,s); 1.50–2.20(6H$_b$,m); 3.23(2H$_c$,m); 4.00–4.30(1H$_d$,m); 5.10(2H$_e$,s); 5.56(2H$_f$,s); 6.56–7.10(2H$_g$,m, rotamers of carbamate-NH); 7.36(5H$_h$,s); 7.63(3H$_{i,i',j}$,app. dd, J$_{ik}$=8Hz,J$_{ii'}$=2Hz); 8.06(2H$_{k,k'}$,app. dd,J$_{ki}$=8Hz,J$_{kj}$=2Hz)ppm.

EX. 51

N$_\epsilon$-Carbobenzoxy-L-lysine phenacyl ester
hydrochloride (33)

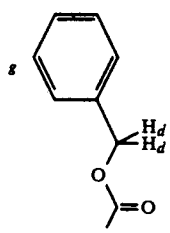

mp 58°–60° C. $^1$H-NMR (CDCl$_3$) δ 1.36(3H$_a$,d,J=8Hz); 3.20(2H$_d$,m); 3.56(2H$_e$,m);3.66(3H $_f$,s); 4.23(2H$_g$, center of 2 sets of dd,J=20Hz, rotamers of the CH$_{2(g)}$geminal system; 4.34–4.58(3H$_{h,i}$,m); 4.60–4.64(1H$_k$,m); 5.10(2H$_j$,s); 6.70–7.26(2H$_l$,m, rotamers of amide —NH); 7.36(5H$_m$,s)ppm.

EX. 45

N-[Methoxysuccinylalanyl-(N$_\epsilon$-carbobenzoxy)lysylprolylmethyl]-N-isopropylamine (29, the LLD diastereomer)

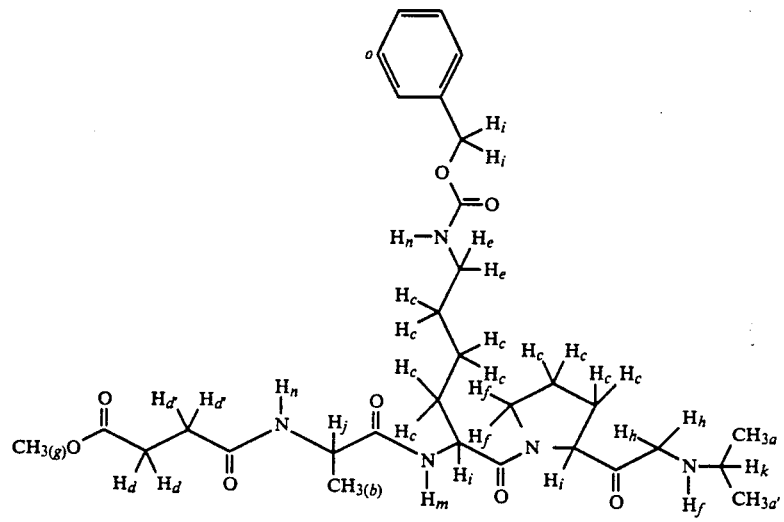

29

Isopropylamine (1.4 g, 24.4 mmoles) was added to a cold solution (0° C.) of 27 (1.45 g, 2.44 mmoles) in THF (5 ml). The reaction mixture was stirred at 0° C. for 12 h, filtered under vacuum and the filtrate evaporated to a crude oil. The residue, containing the product, was redissolved in a small amount of methylene chloride, and chromatographed on 25 g of silica gel column (1×50 cm). The product was eluted with 7% methanol in methylene chloride. The eluent solvent was evaporated under reduced pressure. The reaction produced 0.31 g (0.5 mmole) (21% yield) of a yellow oil. $^1$H-NMR (CDCl$_3$) δ 1.06–1.28(6H$_{a,a'}$,m, rotamers of isopropylamine); 1.32(3H$_b$,d,J=8Hz); 1.38–2.32(10H$_c$,m); 2.46(2H$_d$,app. t, J=8Hz); 2.64(2H$_{d'}$,app. t, J=8Hz); 3.20(2H$_e$,m); 3.52.3.88(3H$_f$,m); 3.66(3H$_g$,s); 4.20,4.32(2H$_h$,center of a set of dd, overlapping with another set, J=20Hz, rotamers of the CH$_{2(h)}$ geminal system); 4.50(2H$_i$,app.t, J=8Hz; 4.50–4.80(2H$_{j,k}$,m); 5.10(2H$_l$,s); 5.42(1H$_m$,m, rotamer of amide —NH); 6.36–7.08(2H$_n$,m, rotamer of amide —NH); 7.35(5H$_o$,s)ppm.

EX. 46

N-[Methoxysuccinylalanyl-(N$_\epsilon$-carbobenzoxy)lysylprolylmethyl]-N-isopropylamine (30, the LLL diastereomer)

(see 29 for structure)

The title compound was prepared by an analogous procedure to that described in the preparation of compound 29. The reaction produced 0.31 g (0.5 mmole) (21% yield) of a yellow oil. $^1$H-NMR (CDCl$_3$) δ 1.06–1.28(6H$_{a,a'}$,m, rotamers of isopropylamine); 1.32(3H$_b$,d, J=8Hz); 1.38–2.32(10H$_c$,m); 2.46(2H$_d$, app.t,J=8Hz); 2.64(2H$_{d'}$,app. t, J=8Hz); 3.20(2H$_e$,m); 3.52.3.88(3H$_f$,m); 3.66(3H$_g$,s); 4.23(2H$_h$, center of 2 sets of dd, J=20Hz, rotamers of the CH$_{2(h)}$ geminal system); 4.34–4.58(3H$_{h,i}$,m); 4.60–4.64(1H$_k$,m); 5.10(2H$_l$,s); 5,42(1H$_m$,m, rotamer of amide —NH); 6.36–7.08(2H$_n$,m, rotamers of amide —NH); 7.35(5H$_o$,s)ppm.

EX. 47 p-Nitrophenyl N-[Methoxylsuccinylalanyl-(N$_\epsilon$-carbobenzoxy)lysylprolylmethyl]-N-isopropylcarbamate (48b, the LLD diastereomer)

(see page 45 for structure)

An ice cooled solution of 29 (0.3 g, 0.5 mmole), N-methylmorpholine (0.07 g, 0.7 mmole) and 4-nitrophenyl chloroformate (0.15 g, 0.75 mmole) in THF (3 mL) was stirred for 2 h at 0° C. The reaction mixture was diluted with methylene chloride (15 mL) and washed subsequently with water (15 mL), 10% aqueous citric acid (15 mL), water (15 mL) and brine (15 mL); dried (2 g of MgSO$_4$) and evaporated in vacuo to an oil. The oil was chromatographed on 5 g of silica gel column (1×25 cm). The impurities were eliminated by first passing 10 mL of methylene chloride and 20 mL of 2% methanol in methylene chloride. Subsequently the compound was eluted with 4% methanol in methylene chloride. Upon evaporation of the eluent solvent under reduced pressure an amorphous solid was obtained. The product was further purified by preparative TLC (100 mg/plate). The TLC plates were developed twice using 4% methanol in ethyl acetate in order to see if two bands were present. The one band observed was scraped from the plate and the product was extracted with 20% methanol in chloroform. An amorphous white solid was obtained by evaporating the extraction solvent under reduced pressure. The incorporation of D-proline into the synthetic scheme gave rise to 89.9 mg (115.0 moles) (23% yield) of amorphous solid (48b), mp 44°–45° C. $^1$H-NMR (CDCl$_3$) (see 48b above). Elemental analysis cal'd. for C$_{38}$H$_{50}$N$_6$O$_{12}$: C,58.3;H,6.44;N,10.73. Found: C, 58.49; H,6.47; N,10.63.

-continued

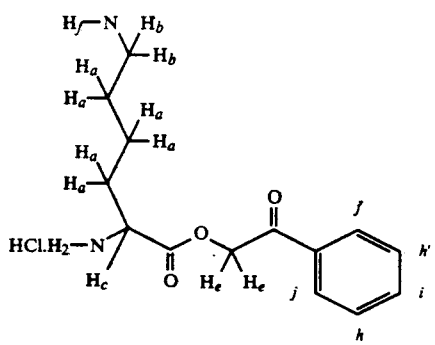

Formic acid (98%) (6 mL) was added to a 10% solution of 32 (3.3 g, 6.9 mmoles) in ethyl acetate (50 mL) cooled to 5° C. Hydrogen chloride gas was slowly bubbled through the cooled solution in three 30s intervals, 10 min apart. The solution was stirred at 5° C. for 30 min and was then allowed to equilibrate to room temperature. The progress of the reaction was monitored by TLC (10% methanol in chloroform). Upon completion of the reaction (3 h at 22° C.), the suspension was filtered. The latter was recrystallized from absolute ethanol/hexane to give 2.2 g (5.1 mmoles) (73% yield) of a crystalline powder, mp 149°–151° C. $^1$H-NMR (DMSO-d$_6$) δ 1.50–2.26(6H$_a$,m); 3.23(2H$_b$,m); 4.03–4.43(1H$_c$,m); 5.10(2H$_d$,s); 5.80(2H$_e$,s); 7.10(1H$_f$,m); 7.36(5H$_g$,s); 7.63(3H$_{h,h',i}$,app. dd,J$_{hj}$=8Hz, J$_{hi}$=2Hz); 8.06(2H$_{j,j'}$,app. dd,J$_{jh}$=8Hz,J$_{ji}$=2Hz); 8.86(2H$_k$,m)ppm. IR(Nujol) 3350, 1750, 1700, 1680, 1585, 1535 cm$^{-1}$.

EX. 52

N$_α$-t-Boc-N-$_δ$-carbobenzoxy-L-ornithine (34)

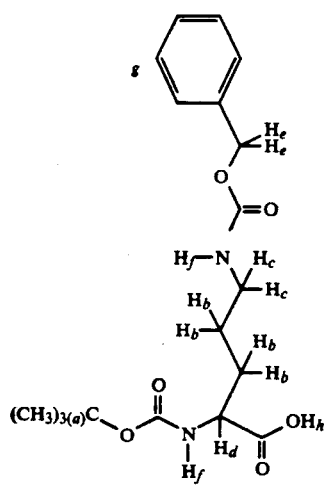

The title compound was synthesized and purified by an analogous procedure to that described in the preparation of compound 31. The residue, containing product, was chromatographed to give 1.34 g (3.6 mmoles) (97% yield) of a transparent oil. $^1$H-NMR (CDCl$_3$) δ 1.46(9H$_a$,s); 1.50–2.10(4H$_b$,m); 3.23(2H$_c$,m); 4.00–4.40(1H$_d$,m); 5.10(2H$_e$,s); 6.83–7.10(2H$_f$,m,rotamer of carbamate -NH); 7.40(5H$_g$,s); 9.80(1H$_h$,s)ppm.

EX. 53

N$_α$-t-Boc-N$_δ$-carbobenzoxy-L-ornithine phenacyl ester (35)

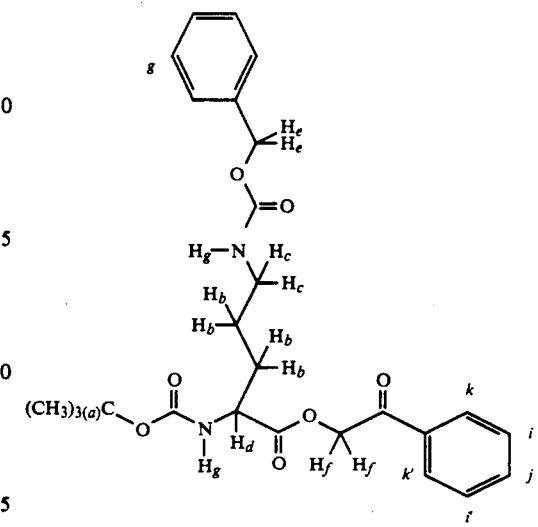

The title compound was synthesized and purified by an analogous procedure to that described in the preparation of compound 32. The reaction produced 3.7 g (7.7 mmoles) (86% yield) of a transparent oil. $^1$H-NMR (CDCl$_3$) δ 1.46(9H$_a$,s); 1.50–2.20(4H$_b$,m); 3.23(2H$_c$,m); 4.00–4.30(1H$_d$,m); 5.10(2H$_e$,s); 5.56(2H$_f$,s); 6.56–7.10(2H$_g$,m, rotamers of carbamate -NH); 7.36(5H$_h$,s); 7.63(3H$_{i,i',j}$,app. dd, J$_{ik}$=8Hz,J$_{ii'}$=2Hz); 8.06(2H$_{k,k'}$,app. dd,J$_{ki}$=8Hz,J$_{kj}$=2Hz)ppm.

EX. 54

N$_δ$-Carbobenzoxy-L-ornithine phenacyl ester hydrochloride (36)

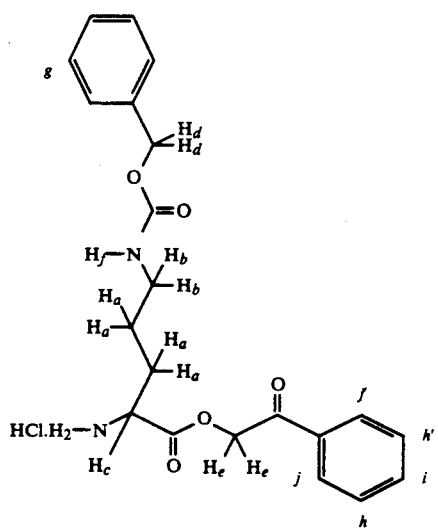

The title compound was prepared by an analogous procedure to that described in the preparation of compound 33. The resulting white powder was recrystallized from ethanol/hexane to give 2.4 g (5.7 mmoles) (76% yield) of a crystalline powder mp 166°–167° C. $^1$H-NMR (DMSO-d$_6$) δ 1.50–2.26(4H$_a$,m); 3.23(2H$_b$,m);

4.03–4.43(1H$_c$,m); 5.10(2H$_d$,s); 5.80(2H$_e$,s); 7.10(1H$_f$,m); 7.36(5H$_g$s); 7.63(3H$_{h,h',i}$,app. dd,J$_{hj}$=8Hz,J$_{hi}$=2Hz); 8.06(2H$_{j,j'}$,app. dd,J$_{jh}$=8Hz,J$_{ji}$=2Hz); 8.86(2H$_k$,m)ppm. IR (Nujol) 3370, 1770, 1700, 1530 cm$^{-1}$.

EX. 55

N-t-Boc-D-proline (37)

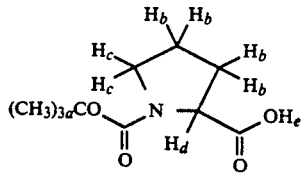

The procedure of Itoh et al.[91] was followed for the preparation of compound 37.

Triethylamine (0.2 g, 2 mmoles) was slowly added to a solution of (D-proline (0.23 g, 2 mmoles) and t-BOC-ON (0.5 g, 2 mmoles) in DMF (3 mL) at room temperature and the mixture stirred for 36 h. The DMF was coevaporated with toluene under vacuum. Aqueous hydrochloric acid (1×10$^{-4}$M) (20 mL) and ethyl acetate (20 mL) were added to the flask to dissolve the residue. The organic layer was washed with water (3×20 mL) and brine (2×20 mL); dried (5 g of MgSO$_4$) and evaporated under reduced pressure. The residue, containing the product, was chromatographed on 5 g of silica gel column (1×25 cm). Upon evaporation under reduced pressure a transparent oil was obtained. The oil was crystallized from ethyl acetate/diethyl ether to give 0.4 g (2 mmoles) (99% yield) of a crystalline powder, mp 133°–134° C. (lit.[91] mp 132°–133° C.). $^1$H-NMR (CDCl$_3$) δ 1.46(9H$_a$,s); 1.86–2.40(4H$_b$,m); 3.43–3.80(2H$_c$,m); 4.26–4.66(1H$_d$,m); 11.43(1H$_e$,s). IR (Nujol) 1740, 1635 cm$^{-1}$.

EX. 56

N-t-Boc-L-proline (38)

(see 37 for structure)

The title compound was prepared by an analogous procedure to that described in the preparation of compound 37. L-proline was substituted in place of the D-enantiomer to produce compound 38. The oil was crystallized from ethyl acetate/diethyl ether to give 0.4 g (2.0 mmoles) (99% yield) of a crystalline powder, mp 133°–134° C. (lit.[91] mp 132°–133° C.).

EX. 57

N-t-Boc-D-proline phenacyl ester (39)

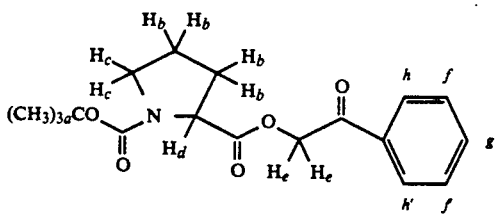

This compound was synthesized by a modified procedure of Hendrickson et al.[85].

2-Bromoacetophenone (0.4 g, 2 mmoles) was added slowly to an ice-cooled solution of t-Boc-D-proline (0.4 g, 2 mmoles) and triethylamine (0.2 g, 2 mmoles) in THF (4 mL). The progress of the reaction was monitored by TLC (5% methanol in chloroform). Upon completion of the reaction (1.5 h), the formed triethylamine salt was filtered, washed with ethyl acetate (10 mL) and the filtrate evaporated under vacuum. The residue, containing the product, was chromatographed on 5 g of silica gel column (1×25 cm). Impurities were eliminated by first passing 25 mL of methylene chloride and subsequently the compound was eluted with 3% methanol in methylene chloride. Upon evaporation of the eluent solvent under reduced pressure a white solid was obtained. The latter was recrystalized from ethyl acetate/hexane. The incorporation of 37 into the product gave 0.58 g (1.75 mmoles) (87.5% yield) of crystalline powder (39), mp 78°–79° C. $^1$H-NMR (CDCl$_3$) δ 1.46(9H$_a$, s); 1.86–2.40(4H$_b$, m); 3.20–3.60(2H$_c$, m); 4.30(1H$_d$, m); 5.80(2H$_e$, s); 7.63(3H$_{f,f',g}$, app. dd, J$_{fh}$=8Hz, J$_{ff}$, =2Hz); 8.06(2 H$_{h,h'}$, app. dd, J$_{hf}$=8Hz, J$_{hg}$=2Hz)ppm.

EX. 58

N-t-Boc-L-proline phenacyl ester (40)

(see 39 for structure)

The tilte compound was prepared by an analogous procedure to that described in the preparation of compound 39. t-Boc-L-proline (38) was substituted into the reaction to produce 0.59 g (1.78 mmoles) (88.8% yield) of crystalline powder (40), mp 76°–78° C.

EX. 59

D-Proline phenacyl ester hydrochloride (41)

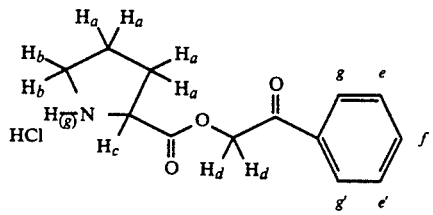

Formic acid (98%) (0.6mL) was added to a cooled solution (0° C.) of t-Boc-D-proline phenacyl ester (0.6 g, 1.75 mmoles) in ethyl acetate (10 mL). Hydrogen chloride gas was slowly bubbled through the above solution in two 30s intervals, 10 min apart. The reaction mixture was stirred for 30 min at 0°–5° C., then allowed to equilibrate to room temperature and stirred until the reaction was completed (approximately 1 h). The suspension was diluted with ethyl acetate and filtered under vacuum. The product was washed with ethyl acetate, air dried and recrystallized from absolute ethanol/diethyl ether. The use of 39 (the D isomer) in this reaction gave 0.3 g (1.1 mmoles) (63.5% yield) of crystalline powder (41), mp 154°–156° C. $^1$H-NMR (DMSO-d$_6$) δ 1.86–2.76(4H$_a$, m); 3.16–3.63(2H$_b$, m); 4.40–4.86(1H$_c$, m); 5.80(2H$_d$, s); 7.63(3H$_{e,e',f}$, app. dd, J$_{eg}$=8Hz, J$_{ee}$,=2Hz); 8.06(2H$_{g,g'}$, app. dd, J$_{ge}$=8Hz, J$_{gf}$=2Hz); 9.30(1H$_g$, m)ppm. IR (Nujol) 1755, 1600, 1500cm$^{-1}$.

EX. 60

L-Proline phenacyl ester hydrochloride (42)

(see 41 for structure)

The title compound was prepared by an analogous procedure to that described in the preparation of compound 41. t-Boc-L-proline phenacyl ester was substituted into the reaction to produce 0.4 g (1.54 mmoles) (88% yield) of crystalline powder (42), mp 144°–156° C.

EX. 61

$N_\epsilon$-Benzoyl-L-lysine (43)

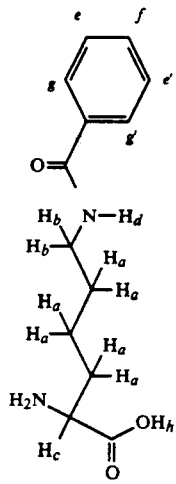

This compound was synthesized by a modified procedure of Kurtz et al.[93]. Copper (II) carbonate, basic (16.3 g, 74.0 mmoles) was added to a hot (80° C.) solution of L-lysine (15 g, 82.0 mmoles) in distilled water (250 mL). Excess copper carbonate was removed by gravity filtration while the mixture was still warm. The epsilon amino group of L-lysine was benzoylated by the dropwise addition of benzoyl chloride (14 g, 99.0 mmoles) in THF (35 mL) to the above solution after being cooled to 5° C. Sodium bicarbonate was added in small portions (total 14 g, 167.0 mmoles) to maintain the pH of the aqueous solution above 7 (pH was monitored with neutral litmus paper). The cold solution was maintained at 5° C. for 4 h and 2 d at room temperature. A hot (80° C.) solution (1 L) of EDTA (14.6 g, 0.25 moles) was added to the reaction mixture, stirred for 1 h and cooled to 10° C. The precipitate collected by vacuum filtration was washed with water and 30 mL of 95% ethanol. The powder, containing the product was purified by first adding the powder to $1\times10^{-1}$M hydrochloric acid (300 mL) and filtering off the sediment. The filtrate was slowly neutralized with 0.01N sodium hydroxide and the precipitate collected by gravity filtration. The latter was then air-dried to give 13 g (57 mmoles) (69.5% yield) of a white powder, mp 232°–234° C. (lit.[93] mp 230°–233° C.). $^1$H-NMR (DMSO-d$_6$) δ 1.36–1.90(-6H$_a$,m); 3.20(2H$_b$,m); 4.20–4.53(1H$_c$,m); 7.16(1H$_d$,m, rotamer of amide –NH); 7.43(2H$_{e,e'}$, app. dd, J$_{ef}$=8Hz, J$_{ee'}$=2Hz); 7.63(1H$_f$, app. dd, J$_{fe}$=8Hz, J$_{fg}$=2Hz); 8.03(2H$_{f,f'}$, app dd, J$_{ge}$=8Hz, J$_{gf}$=2Hz); 9.50(1H$_h$,s)ppm. IR (Nujol) 3330, 3030, 1687, 1270, 735, 695 cm$^{-1}$.

EX. 62

S-(1-Phenyl-5-tetrazolyl) chlorothioformate (52)

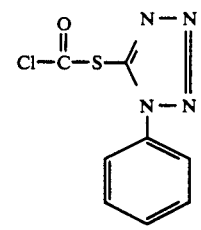

A 20% phosgene solution in toluene (14.4 ml, 25.2 mmole) was added to a mixture of triethylamine (2.58 ml, 18.5 mmol) and 1-phenyl-1H-tetrazol-5-thiol (3.00 g, 16.8 mmole) in THF (15 ml) at 5° C. over 10 min. The reaction mixture was stirred for an hour at 5° C. and filtered. The filtrate obtained was evaporated and the residue washed thoroughly with ethyl ether. It was then recrystallized by dissolving in THF and precipitating with ethyl ether to give white crystal (2.92 g, 72%) m.p. 112°–114° C. IR (Film) 1718, 1645, 1590, 1490 and 1395 cm$^{-1}$. $^1$H-NMR (CDCl$_3$) δ7.52 (s, aromatic H).

EX. 63

S-(1-Phenyl-5-tetrazolyl)-N-[(N-Boc-L-prolyl)methyl]-N-isopropylthio carbamate (53)

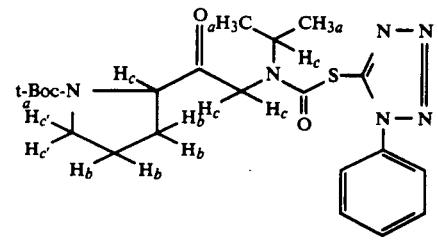

Compound 52 (1.30 g, 5.40 mmole) was added to a solution of compound 20 (0.8 g, 2.96 mmole) and triethylamine (0.6 ml, 4.30 mmol) 5° C. The mixture was stirred for 2 h at 5° C. The reaction mixture was diluted with chloroform. The organic layer was washed with water, dried over MgSO$_4$ and evaporated to give an oil. The oil obtained was purified by column chromatography (silica gel, CHCl$_3$ 1% MeOH in CHCl - 2% MeOH in CHCl$_3$) to give white crystals (0.6 g, 42.8%). $^1$H-NMR (CDCl$_3$) δ1.2 (6Ha',d), 1.4(9Ha,s), 1.95(4Hb,m), 3.45 (4Hc',t) 4.2 (4Hc,m), 7.55(5Hd,s). Anal. Calcd for C$_{22}$H$_{30}$N$_6$O$_4$S: C,55.69; H,6.37; N,17.71; S,6.74. Found: C55.50; H, 6.43; N,17.66; S,6.68.

EX. 64

S-(1-Phenyl-5-tetrazoyl)-N-prolylmethyl-N-isopropyl thiocarbamate hydrochloride 54

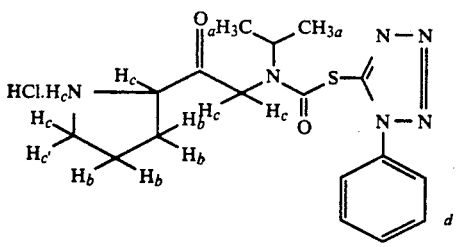

Hydrogen chloride gas was passed through a solution of 53 (0.6 g) in ethyl acetate (5 ml) at 5° C. for 3 min. The solution was allowed to stand at 5° C. for 10 min and then evaporated in vacuo. The residue was triturated with ethyl ether to give white powder (0.24 g, 46%). $^1$HNMR δ1.2(6Ha,d), 2.0(4H6,m), 3.4–4.9(7Hc,m), 7.5(5Hd,s).

EX. 65

S-(1-Phenyl-5-tetrazoyl)-N-[methoxysuccinyl-alanyl-(N6-carbonbenzoxyl)lysylprolylmethyl]-N-isopropyl thiocarbamate (PC5)

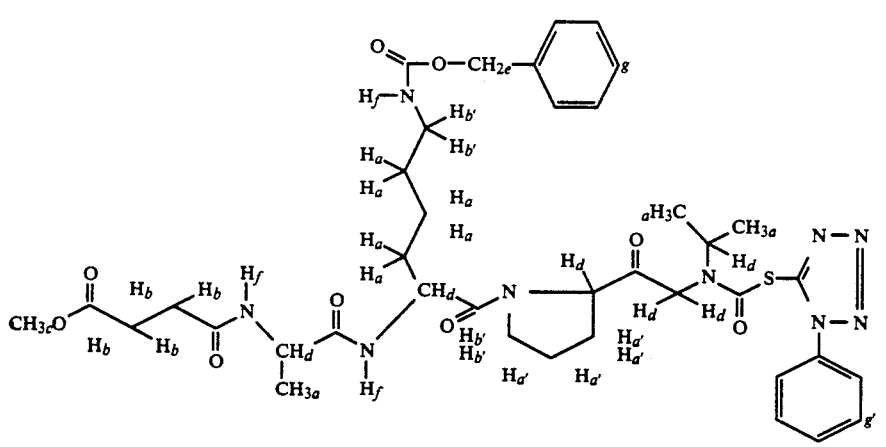

To a cooled solution (−20° C.) of compound 7 (232 mg, 0.498 mmole) and N-methylmorpholine (0.064 ml, 0.498 mmole) in THF (3 ml), isobutyl chloroformate (0.06 ml, 0.498 mmole) was added. The mixture was stirred for 15 min at −15° C. to −30° C. Compound 54 (226 mg, 0.550 mmole) was added as a solid followed by N-methyl morpholine (0.064 ml, 0.55 mmol). The reaction mixture was allowed to warm to room temperature and stirred overnight. The solution was diluted with methylene chloride, washed with 10% citric acid, brine and water. It was subsequently dried (MgSO$_4$) and the solvent evaporated. The residue was purified by column chromatography (silica gel, CH$_2$Cl$_2$ to 2% methanol in CH$_2$Cl$_2$). A white powder was obtained (200 mg, 48.8%) m.p. 60°–65° C. $^1$H-NMR(CDCl$_3$) δ1.35(15Ha,m), 1.95(4Ha',m), 2.5(4Hb,d), 3.15(4Hb',m), 3.62(3Hc,s), 3.7–4.9(6Hd,m), 5.1(2He,s), 5.2–6.8(3Hf,m); 7.25(5Hg,s), 7.45(5Hg',s). Anal. Cald for C$_{39}$H$_{51}$N$_9$O$_9$S. THF:C,57.77; H,6.65; N,14.10; S,3.57; found C,57.65; H,6.40; N,14.32; S,3.57.

EX. 66

S-(1-Phenyl-5-tetrazoyl)-N-[methoxysuccinyl-Nδ-carbobenzoxyl) ornithyl alanyl prolyl methyl]-N-isopropyl thiocarbamate (PC6)

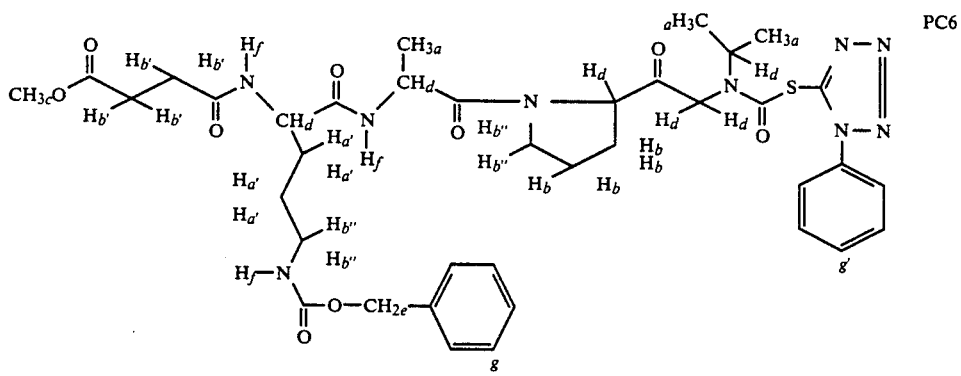

PC6 was prepared following a similar procedure as for the preparation of PC5 using compound 12 instead of 7. PC6 was obtained as a white powder (37.3%). m.p. 75° C. $^1$HNMR (CDCl$_3$) δ1.2 (9Ha, m), 1.6(4Ha,m), 2.0(4Hb,m), 2.55(4Hb',s), 2.9–3.2 (4H6'',m), 3.61(3Hc,s); 3.7–4.8(6Hd,m), 5.05(2He,s); 5.3–6.9(3Hf,m) 7.25(5Hg,s), 7.5(5Hg,s). Anal. calcd for C$_{38}$H$_{49}$N$_9$O$_9$S: C,56.50; H,6.11; N,15.60; S,3.96. Found: C,56.59; H,6.16; N,15.53; S,3.92.

EX. 67

Elastase Enzyme Inhibitory Studies

These studies are conducted to show the activities of some of the compounds of this invention as inhibitors of various forms of the enzyme elastase. The results are shown in the following Tables.

Inhibition of PPE and HLE by Novel Peptidyl Carbamates: Variations at $P_3$

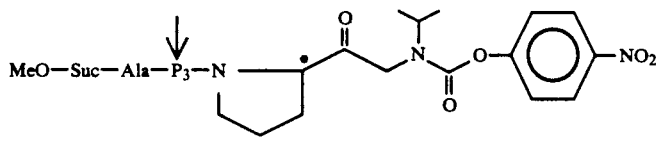

| Compound | $P_3{}^a$ | Isomer[b] | Ki (μM) PPE | HLE |
|---|---|---|---|---|
| 5 (a,b) | N-ε-Cbz—Lys | a (D) | N.I.[c] | 11.30 |
|  |  | b (L) | 3.40 | 0.22 |
| 6 (a,b) | N-ε-Bz—Lys | a (D) | N.I. | 38.50 |
|  |  | b (L) | 3.80 | 0.31 |
| 7 (a,b) | N-δ-Cbz—Orn | a (D) | N.I. | 19.25 |
|  |  | b (L) | 8.65 | 1.05 |
| 8 (a,b) | N-δ-Bz—Orn | a (D) | N.I. | 100.00 |
|  |  | b (L) | 14.30 | 2.14 |

[a]Cbz = COOCH$_2$Ph; Bz = COPh; Lys = lysine, Orn = ornithine
[b](L) and (D) refer to the configuration at the prolyl α-carbon
[c]N.I. refers to no inhibition at I/E = 100.

Inhibition of PPE and HLE by Novel Peptidyl Carbamates Variations at $P_4$

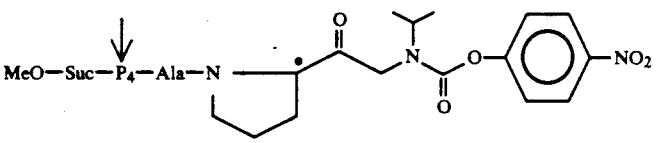

| Compound | $P_4{}^a$ | Isomer[b] | Ki (μM) PPE | HLE |
|---|---|---|---|---|
| 1 (a,b) | N-ε-Cbz—Lys | a (L) | N.I.[c] | 0.47 |
|  |  | b (D) | N.I. | 7.63 |
| 2 (a,b) | N-ε-Bz—Lys | a (L) | N.I. | 0.38 |
|  |  | b (D) | N.I. | 3.13 |
| 3 (a,b) | N-δ-Cbz—Orn | a (L) | N.I. | 0.65 |
|  |  | b (D) | N.I. | 7.95 |
| 4 (a,b) | N-δ-Bz—Orn | a (L) | N.I. | 0.19 |
|  |  | a (D) | N.I. | 17.70 |

[a]Cbz = COOCH$_2$Ph; Bz = COPh; Lys = lysine; Orn = ornithine
[b](L) and (D) refer to the configuration at the prolyl α-carbon
[c]N.I. refers to no inhibition at I/E = 100

The invention now being fully described, it will be apparent to one of ordinary skill in the art that many changes and modifications can be made thereto without departing from the spirit or scope of the invention as set forth herein.

What is claimed herein is:

1. A compound selected from the group consisting of a compound of the formula

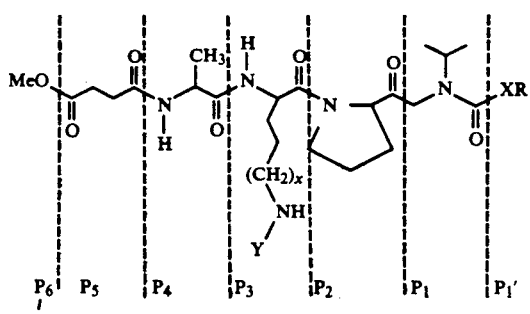

(I)

and a compound of the formula

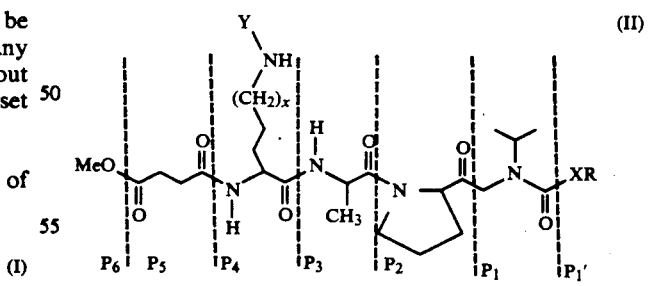

(II)

wherein
x is 1 or 2;
Y is carbobenzoxy or benzoyl; and XR is

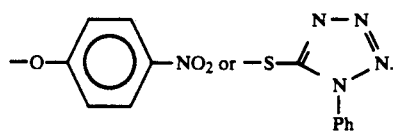

2. The compound of claim 1 having the formula

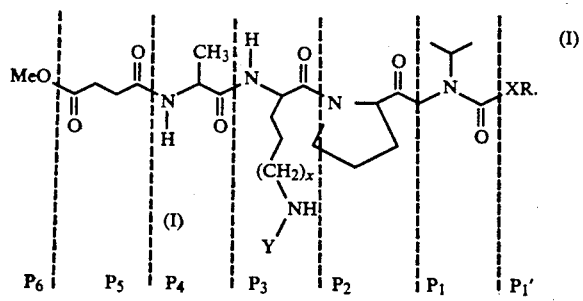

3. The compound of claim 1 having the formula

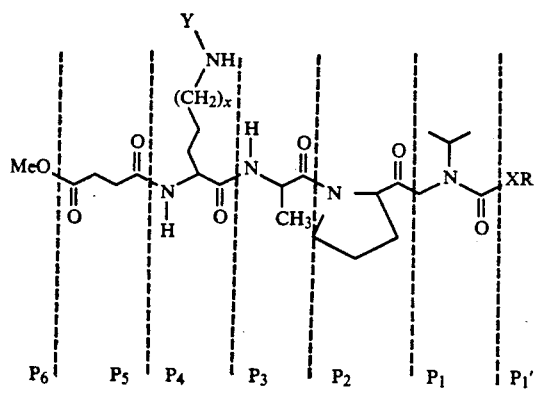

4. The compound of claim 1 being selected from the group consisting of
1. p-Nitrophenyl N-[(Methoxysuccinyl)-L-alanyl-L-alanyl-L-prclymethyl]-N-isopropylcarbamate,
2. Methyl succinimide succinate
3. t-Butyl Methoxysuccinyl-L-alanine ester,
4. Methoxysuccinyl-L-alanine,
5. $N_\alpha$-Methoxysuccinyl-L-alanyl-$N_\epsilon$-benzoyl-L-lysine,
6. $N_\alpha$-Methoxysuccinyl-L-alanyl-$N_\epsilon$-carbobenzoxy-L-lysine phenacyl ester,
7. $N_\alpha$-Methoxysuccinyl-L-alanyl-$N_\epsilon$-carbobenzoxy-L-lysine,
8. $N_\alpha$-Methoxysuccinyl-L-alanyl-$N_\delta$-carbobenzoxy-L-omithine phenacyl ester,
9. $N_\alpha$-Methoxysuccinyl-L-alanyl-$N_\delta$-carbobenzoxy-L-omithine,
10. $N_\alpha$-Methoxysuccinyl-$N_\delta$-carbobenzoxy-L-omithine,
11. $N_\alpha$-Methoxysuccinyl-$N_\delta$-carbobenzoxy-L-omithyl-L-alanine t-butyl ester,
12. $N_\alpha$-Methoxysuccinyl-$N_\delta$-carbobenzoyl-L-omithyl-L-alanine,
13. $N_\alpha$-Methoxysuccinyl-$N_\epsilon$-carbobenzoxy-L-lysine,
14. $N_\alpha$-Methoxysuccinyl-$N_\epsilon$-carbobenzoxy-L-lysyl-L-alanine t-butyl ester,
15. $N_\alpha$-Methoxysuccinyl-$N_\epsilon$-carbobenzoxy-L-lysyl-L-alanine,
16. $N_\alpha$-Methoxysuccinyl-$N_\epsilon$-benzoyl-L-lysine,
17. $N_\alpha$-Methoxysuccinyl-$N_\epsilon$-benzoyl-L-lysyl-L-alanine t-butyl ester,
18. $N_\alpha$-Methoxysuccinyl-$N_\epsilon$-benzoyl-L-lysyl-L-alanine,
19. N-Boc-L-prolyl chloromethyl ketone,
20. N-[(N-Boc-L-prolyl)methyl]isopropylamine,
21. N-[(N-Boc-L-prolyl)methyl]-N-isopropylcarbamate,
22. p-Nitrophenyl N-(L-prolylmethyl)-N-isopropyl-carbamate hydrochloride,
23. $N_\alpha$-Methoxysuccinyl-L-alanyl-$N_\epsilon$-carbobenzoxy-L-lysyl-D-proline phenacyl ester,
24. $N_\alpha$-Methoxysuccinyl-L-alanyl-$N_\epsilon$-carbobenzoxy-L-lysyl-L-proline phenacyl ester,
25. $N_\alpha$-Methoxysuccinyl-L-alanyl-$N_\epsilon$-carbobenzoxy-L-lysyl-D-proline,
26. $N_\alpha$-Methoxysuccinyl-L-alanyl-$N_\epsilon$-carbobenzoxy-L-lysyl-L-proline,
27. $N_\alpha$-Methoxysuccinyl-L-alanyl-$N_\epsilon$-carbobenzoxy-L-lysyl-D-prolyl chloromethyl ketone,
p-Nitrophenyl N-[Methoxysuccinyl-($N_\epsilon$-carbobenzoxy)-L-lysyl-L-alanyl-L-prolylmethyl]-N-isopropylcarbamate,
p-Nitrophenyl N-[Methoxysuccinyl-($N_\epsilon$-carbobenzoxy)-L-lysyl-L-alanyl-D-prolylmethyl]-N-isopropylcarbamate,
p-Nitrophenyl N-[Methoxysuccinyl-($N_\epsilon$-benzoyl)-L-lysyl-L-alanyl-L-prolylmethyl]-N-isopropylcarbamate,
p-Nitrophenyl N-[Methoxysuccinyl-($N_\epsilon$-benzoyl)-L-lysyl-L-alanyl-D-prolylmethyl]-N-isopropylcarbamate,
p-Nitrophenyl N-[Methoxysuccinyl-($N_\delta$-carbobenzoxy)-L-omithyl-L-alanyl-L-prolylmethyl]-N-isopropylcarbamate,
p-Nitrophenyl-($N_\delta$-carbobenzoxy)-L-omithyl-L-alanyl--D-prolylmethyl[-N--isopropylcarbamate,
p-Nitrophenyl N-[Methoxysuccinyl-($N_\delta$-benzoyl)-L-omithyl-L-alanyl-L-prolylmethyl]-N-isopropylcarbamate,
p-Nitrophenyl N-[Methoxysuccinyl-($N_\delta$-benzoyl)-L-omithyl-L-alanyl-D-prolylmethyl]-N-isopropylcarbamate,
p-Nitrophenyl N-[Methoxysuccinyl-L-alanyl-($N_\epsilon$-carbobenzoxy)-L-lysyl-L-prolylmethyl]-N-isopropylcarbamate,
p-Nitrophenyl N-[Methoxysuccinyl-L-alanyl-($N_\epsilon$-carbobenzoxy)-L-lysyl-D-prolylmethyl]-N-isopropylcarbamate,
p-Nitrophenyl N-[Methoxysuccinyl-L-alanyl-($N_\epsilon$-benzoyl)-L-lysyl-L-prolylmethyl]-N-isopropylcarbamate,
p-Nitrophenyl N-[Methoxysuccinyl-L-alanyl-($N_\epsilon$-benzoyl)-L-lysyl-D-prolylmethyl]-N-isopropylcarbamate,
p-Nitrophenyl N-[Methoxysuccinyl-L-alanyl-($N_\delta$-carbobenzoxy)-L-ornithyl-L-prolylmethyl]-N-isopropylcarbamate,
p-Nitrophenyl N-[Methoxysuccinyl-L-alanyl-($N_\delta$-carbobenzoxy)-L-ornithyl-D-prolylmethyl]-N-isopropylcarbamate,
p-Nitrophenyl N-[Methoxysuccinyl-L-alanyl-($N_\delta$-benzoyl)-L-ornithyl-L-prolylmethyl]-N-isopropylcarbamate,
p-Nitrophenyl N-[Methoxysuccinyl-L-alanyl-($N_\delta$-benzoyl)-L-ornithyl-D-prolylmethyl]-N-isopropylcarbamate,
S-(1-phenyl-5-tetrazoyl)-N-[methoxysuccinylalanyl($N_\epsilon$-Carbobenzoxyl) lysyl prolyl methyl]-N-isopropylthio carbamate, or
S-(1-phenyl-5-tetrazoyl)-N-[methoxysuccinyl-(N-carbobenzoyl)ornithylalanyl(prolylmethyl)-N-isopropylthio carbamate.
5. The compound of claim 1 selected from the group consisting of
p-Nitrophenyl N-[Methoxysuccinyl-($N_\epsilon$-carbobenzoxy)-L-lysyl-L-alanyl-L-prolylmethyl]-N-isopropylcarbamate, p-Nitrophenyl N-[Methoxysuccinyl-(N$_\epsilon$-carbobenzoxy)-L-lysyl-L-alanyl-D-prolylmethyl]-N-isopropylcarbamate, p-Nitrophenyl N-[Methoxysuccinyl-(N$_\epsilon$-benzoyl)-L-lysyl-L-alanyl-L-prolylmethyl]-N-isopropylcarbamate, p-Nitrophenyl N-[Methoxysuccinyl-(N$_\epsilon$-benzoyl)-L-lysyl-L-alanyl-D-prolylmethyl]-N-isopropylcarbamate, p-Nitrophenyl N-[Methoxysuccinyl-(N$_\delta$-carbobenzoxy)-L-ornithyl-L-alanyl-L-prolylmethyl]-N-isopropylcarbamate, p-Nitrophenyl-(N$_\delta$-carbobenzoxy)-L-ornithyl-L-alanyl-D-prolylmethyl]-N-isopropylcarbamate, p-Nitrophenyl N-[Methoxysuccinyl-(N$_\delta$-benzoyl)-L-ornithyl-L-alanyl-L-prolylmethyl]-N-isopropylcarbamate, p-Nitrophenyl N-[Methoxysuccinyl-(N$_\delta$-benzoyl)-L-ornithyl-L-alanyl-D-prolylmethyl]-N-isopropylcarbamate, and p-Nitrophenyl N-[Methoxysuccinyl-L-alanyl-(N$_\epsilon$-carbobenzoxy)-L-lysyl-L-prolylmethyl]-N-isopropylcarbamate.

6. The compound of claim 1 selected from the group consisting of p-Nitrophenyl N-[Methoxysuccinyl-L-alanyl-(N$_\epsilon$-carbobenzoxy)-L-lysyl-D-prolylmethyl]-N-isopropylcarbamate, p-Nitrophenyl N-[Methoxysuccinyl-L-alanyl-(N$_\epsilon$-benzoyl)-L-lysyl-L-prolylmethyl]-N-isopropylcarbamate, p-Nitrophenyl N-[Methoxysuccinyl-L-alanyl-(N$_\epsilon$-benzoyl)-L-lysyl-D-prolylmethyl]-N-isopropylcarbamate, p-Nitrophenyl N-[Methoxysuccinyl-L-alanyl-(N$_\delta$-carbobenzoxy)-L-ornithyl-L-prolylmethyl]-N-isopropylcarbamate, p-Nitrophenyl N-[Methoxysuccinyl-L-alanyl-(N$_\delta$-carbobenzoxy)-L-ornithyl-D-prolylmethyl]-N-isopropylcarbamate, p-Nitrophenyl N-[Methoxysuccinyl-L-alanyl-(N$_\delta$-benzoyl)-L-ornithyl-L-prolylmethyl]-N-isopropylcarbamate, p-Nitrophenyl N-[Methoxysuccinyl-L-alanyl-(N$_\delta$-benzoyl)-L-ornithyl-D-prolylmethyl]-N-isopropylcarbamate, S-(1-phenyl-5-tetrazoyl)-N-[methoxysuccinylalanyl(N$_\epsilon$-Carbobenzoxyl) lysyl prolyl methyl]-N-isopropylthio carbamate, or S-(1-phenyl-5-tetrazoyl)-N-[methoxysuccinyl(N-carbobenzoyl)ornithylalanyl(prolylmethyl)N-isopropylthio carbamate.

7. The compound of claim 1 having the formula

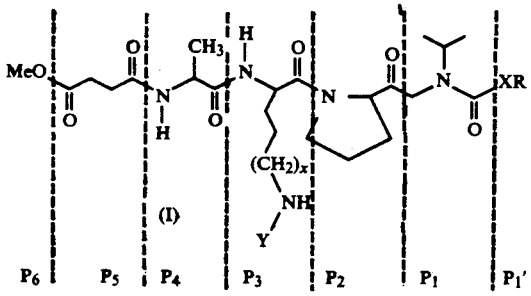

wherein
x is 1 or 2;
Y is carbobenzoxy; and
XR is

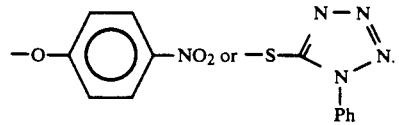

8. The compound of claim 1 having the formula

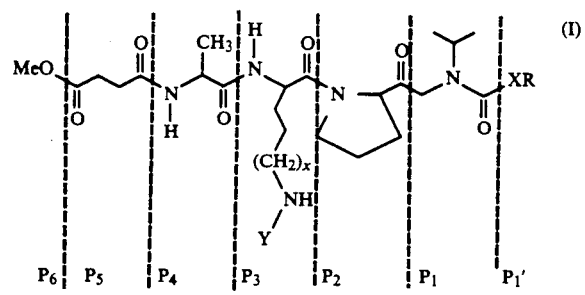

wherein
x is 1 or 2;
Y is benzoyl, and
XR is

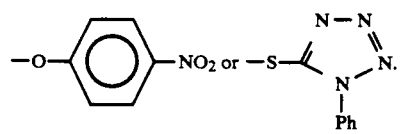

9. The compound of claim 1 having the formula

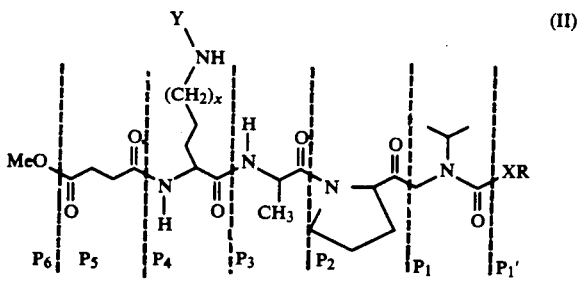

wherein
x is 1 or 2;
Y is carbobenzoxy; and
XR is

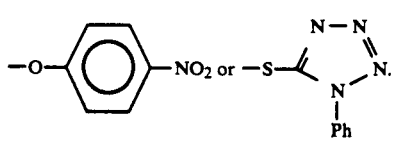

10. The compound of claim 1 having the formula

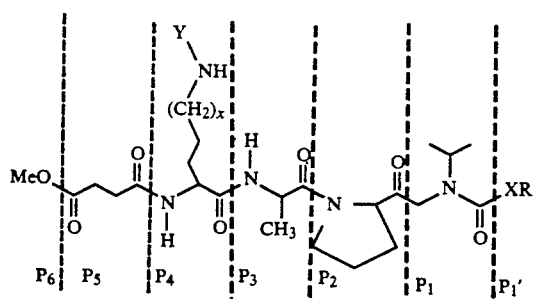

(II)

wherein
x is 1 or 2;
Y is benzoyl; and
XR is

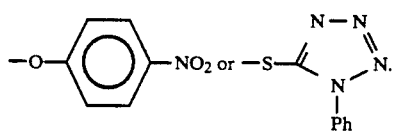

11. The compound of claim 1 having the formula

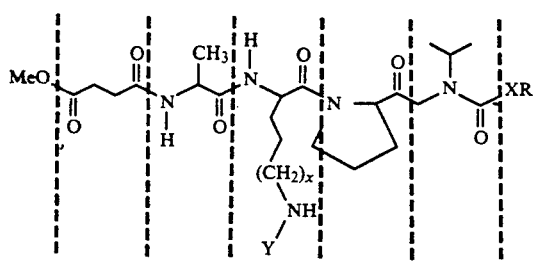

(I)

wherein
x=1 or 2;
Y is carbobenzoxy or benzoyl; nd
XR is

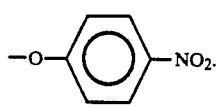

12. The compound of claim 1 having the formula

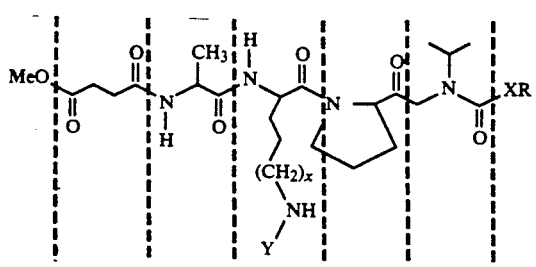

(I)

wherein
x=1 or 2;
Y is carbobenzoxy or benzoyl, and
XR is

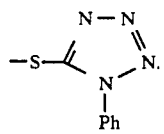

13. The compound of claim 1 having the formula

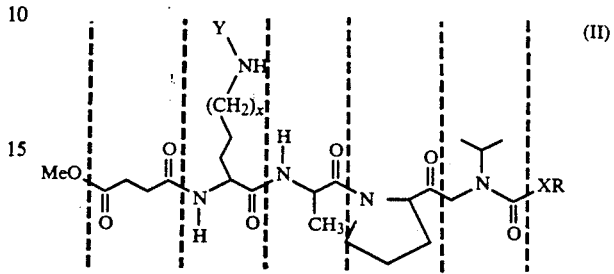

(II)

wherein
x is 1 or 2;
Y is carbobenzoxy or benzoyl, and
XR is

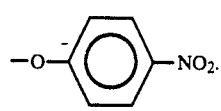

14. The compound of claim 1 having the formula

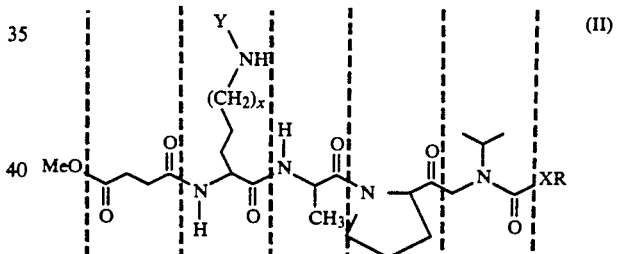

(II)

wherein
x is 1 or 2;
Y i carbobenzoxy or benzoyl; and
XR is

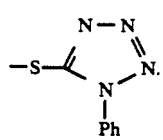

15. An enzyme elastase inhibitory composition, comprising
an enzyme elastase inhibitory amount of the compound of claim 1; and
a carrier.

16. The composition of claim 14, wherein
the carrier is a pharmaceutically-acceptable carrier.

17. A method of selectively inhibiting the enzyme elastase in an animal or a human in need of such treatment comprising administering to said animal or human an enzyme elastase inhibiting amount of the compound of claim 1.

18. A method of selectively inhibiting the enzyme elastase in an animal or a human in need of such treatment comprising administering to said animal or human an enzyme elastase inhibiting amount of the composition of claim 15.
19. The compound of claim 1 being selected from the group consisting of
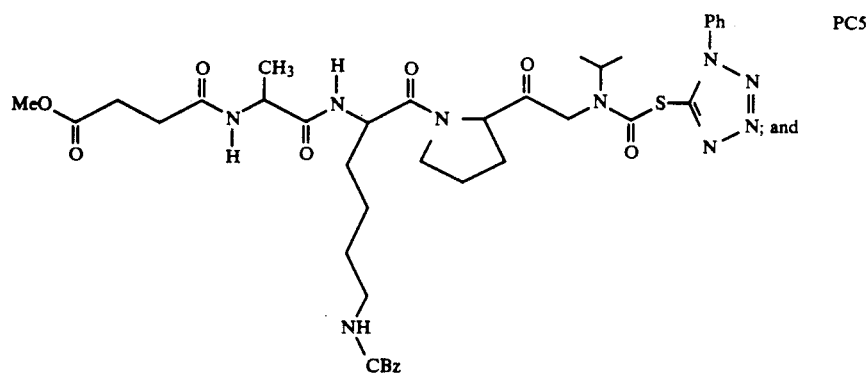
PC5
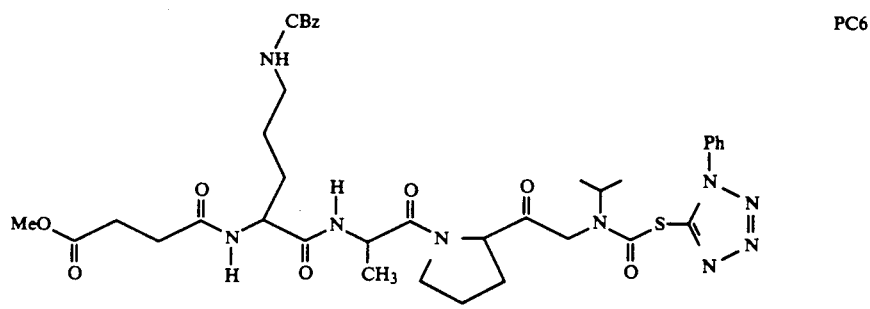
PC6
* * * * *